US012617838B2

(12) United States Patent
Mamonkin et al.

(10) Patent No.: US 12,617,838 B2
(45) Date of Patent: May 5, 2026

(54) AUTO/ALLO-IMMUNE DEFENSE RECEPTORS FOR THE SELECTIVE TARGETING OF ACTIVATED PATHOGENIC T CELLS AND NK CELLS

(71) Applicant: Baylor College of Medicine, Houston, TX (US)

(72) Inventors: Maksim Mamonkin, Houston, TX (US); Malcolm K. Brenner, Houston, TX (US); Feiyan Mo, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 1328 days.

(21) Appl. No.: 17/049,561

(22) PCT Filed: Apr. 25, 2019

(86) PCT No.: PCT/US2019/029163
§ 371 (c)(1),
(2) Date: Oct. 21, 2020

(87) PCT Pub. No.: WO2019/210081
PCT Pub. Date: Oct. 31, 2019

(65) Prior Publication Data
US 2021/0077530 A1 Mar. 18, 2021

Related U.S. Application Data

(60) Provisional application No. 62/662,817, filed on Apr. 26, 2018.

(51) Int. Cl.
| | |
|---|---|
| *A61K 38/00* | (2006.01) |
| *A61K 40/11* | (2025.01) |
| *A61K 40/22* | (2025.01) |
| *A61K 40/31* | (2025.01) |
| *A61K 40/41* | (2025.01) |
| *A61K 40/42* | (2025.01) |
| *A61P 37/06* | (2006.01) |
| *C07K 14/705* | (2006.01) |
| *C12N 5/0783* | (2010.01) |
| *A61K 40/50* | (2025.01) |

(52) U.S. Cl.
CPC ........ *C07K 14/70578* (2013.01); *A61K 40/11* (2025.01); *A61K 40/22* (2025.01); *A61K 40/31* (2025.01); *A61K 40/418* (2025.01); *A61K 40/4258* (2025.01); *A61P 37/06* (2018.01); *C07K 14/70575* (2013.01); *C12N 5/0636* (2013.01); *A61K 40/50* (2025.01); *A61K 2239/38* (2023.05); *A61K 2239/48* (2023.05); *C07K 2319/30* (2013.01)

(58) Field of Classification Search
None
See application file for complete search history.

(56) References Cited

U.S. PATENT DOCUMENTS

| | | | |
|---|---|---|---|
| 7,871,795 B2 * | 1/2011 | McGarrity | ......... C12N 15/1093 |
| | | | 435/325 |
| 2010/0178276 A1 | 7/2010 | Sadelain et al. | |
| 2015/0203560 A1 | 7/2015 | Grewal et al. | |
| 2016/0024176 A1 | 1/2016 | Damschroder et al. | |
| 2016/0311901 A1 | 10/2016 | Jarjour et al. | |

FOREIGN PATENT DOCUMENTS

| | | | |
|---|---|---|---|
| CA | 3007258 A1 | 6/2017 | |
| JP | 2021-521847 | 8/2021 | |
| JP | 7584127 | 11/2024 | |
| WO | 2014127261 A1 | 8/2014 | |
| WO | 2016/113395 A1 | 7/2016 | |
| WO | WO2016210447 A1 | 12/2016 | |
| WO | WO-2017011804 A1 | 1/2017 | |
| WO | PCT/US2016/068349 | * 12/2017 | |

OTHER PUBLICATIONS

Sadelain (Cancer Discov. Apr. 2013; 3(4):388-398) (Year: 2013).*
Geyer et al: "Review: Current clinical applications of chimeric antigen receptor (CAR) modified T cells", Cytotherapy, vol. 18, No. 11, Nov. 1, 2016 (Nov. 1, 2016), pp. 1393-1409.
Mo, Feiyan et al: "Engineered off-the-shelf therapeutic T cells resist host immune rejection", Nature Biotechnology, vol. 39, No. 1, Jan. 2021 (Jan. 2021), pp. 56-63.
Torikai et al: "A foundation for universal T-cell based immunotherapy : T cells engineered to express a GDI9-specific chimeric-antigen-receptor and eliminate expression of endogenous TCR", Blood, vol. 119, No. 24, Jun. 14, 2012 (Jun. 14, 2012), pp. 5697-5705, American Society of Hematology NLD, US.
Mo, F. et al., "Engineered off-the-shelf therapeutic T cells resist host immune rejection", Nature Biotechnology, Jul. 13, 2020, vol. 39, No. 1, pp. 56-63.
Moran et al. "The TNFRs OX40, 4-1BB, and CD40 as targets for cancer immunotherapy", Curr Opin Immunol, vol. 25, No. 2, 2013.

* cited by examiner

*Primary Examiner* — Meera Natarajan
(74) *Attorney, Agent, or Firm* — Norton Rose Fulbright US LLP

(57) ABSTRACT

Embodiments of the disclosure concern engineered auto/allo-immune defense receptor (ADR)-expressing T cells that selectively target activated T cells, including pathogenic T cells, to incapacitate them. The chimeric receptors comprise moieties for targeting 4-1BB, 0X40, and CD40L, for example, whose expression is indicative of activated T cells. In particular embodiments, there are methods of preventing or treating conditions associated with activated T cells using adoptive T-cell transfer of cells encoding the ADRs.

24 Claims, 38 Drawing Sheets

Specification includes a Sequence Listing.

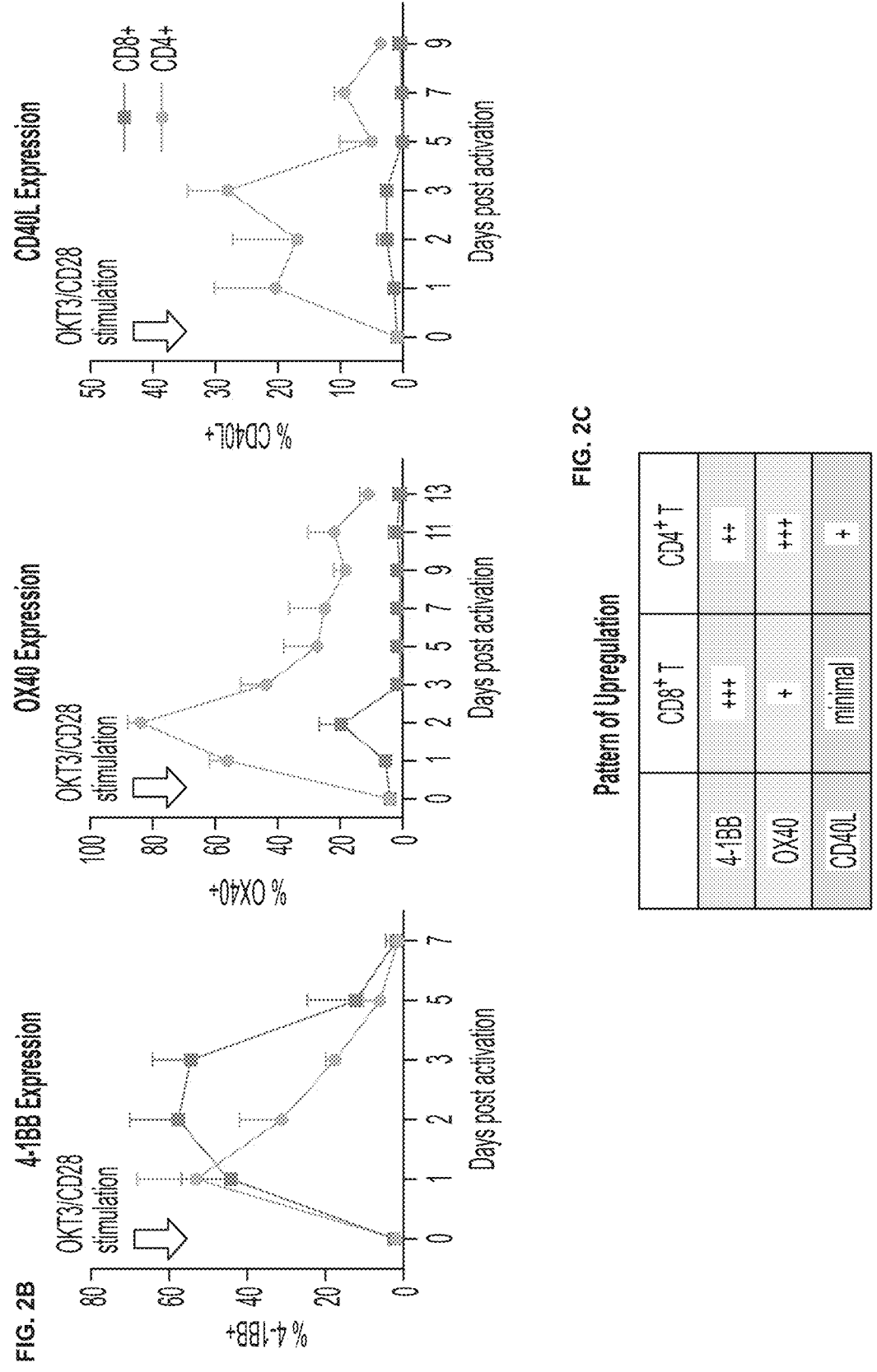

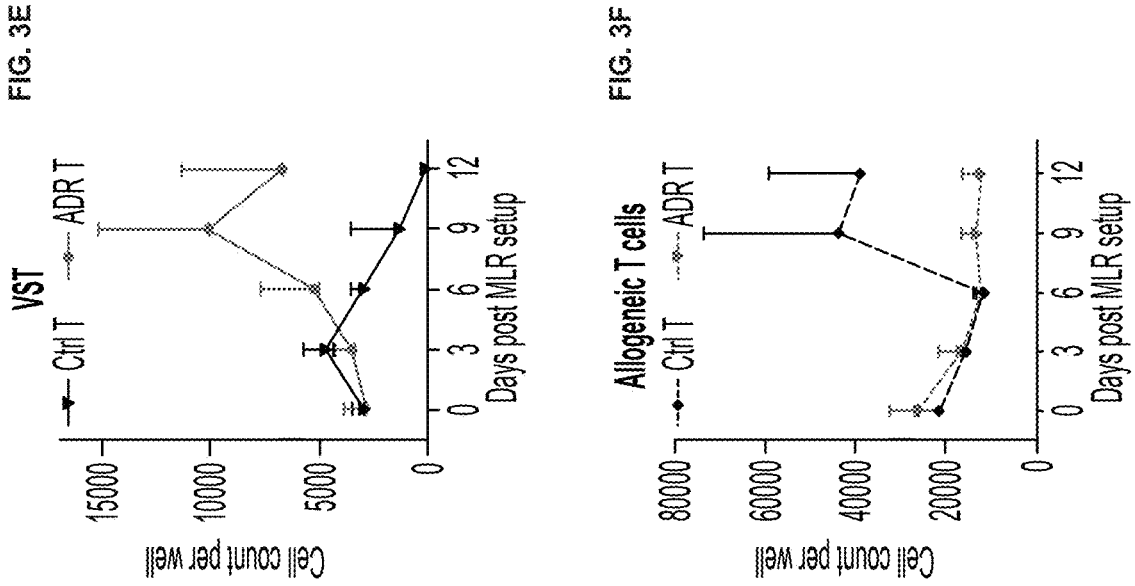
FIG. 3E
FIG. 3F
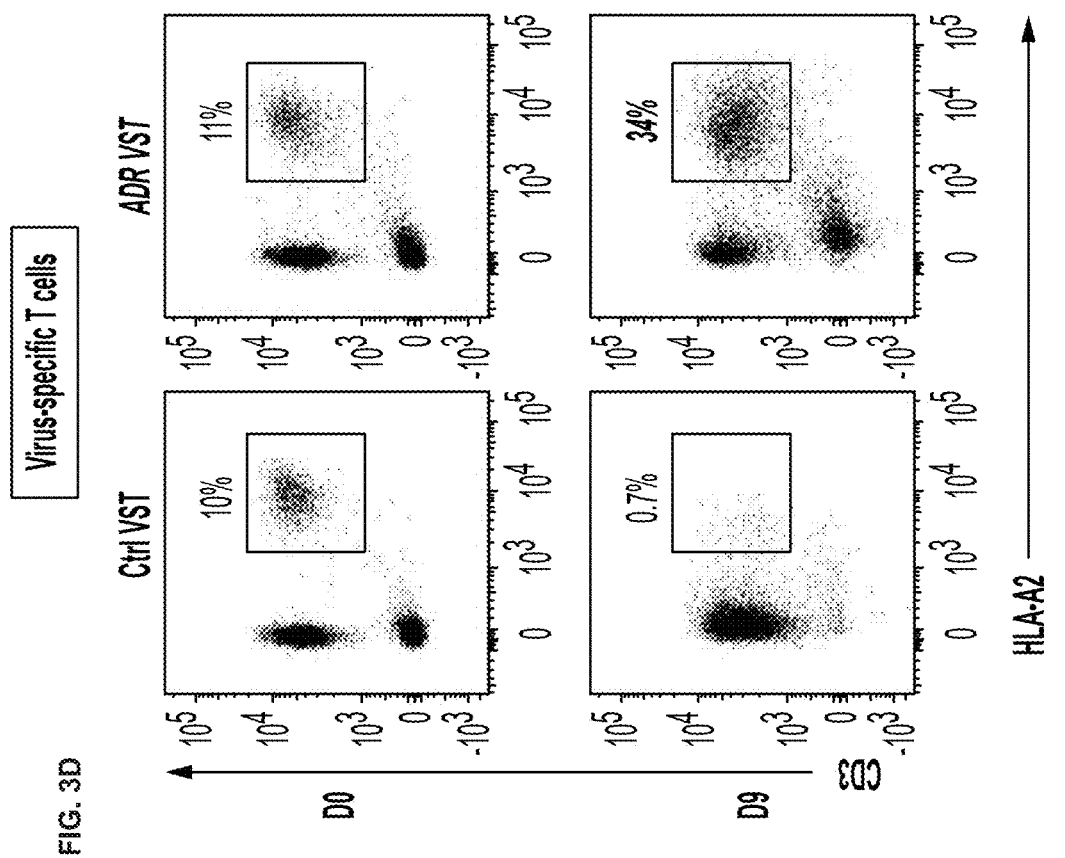
FIG. 3D

FIG. 6A NK cells 4-1BB expression

Resting NK cells

Activated NK cells

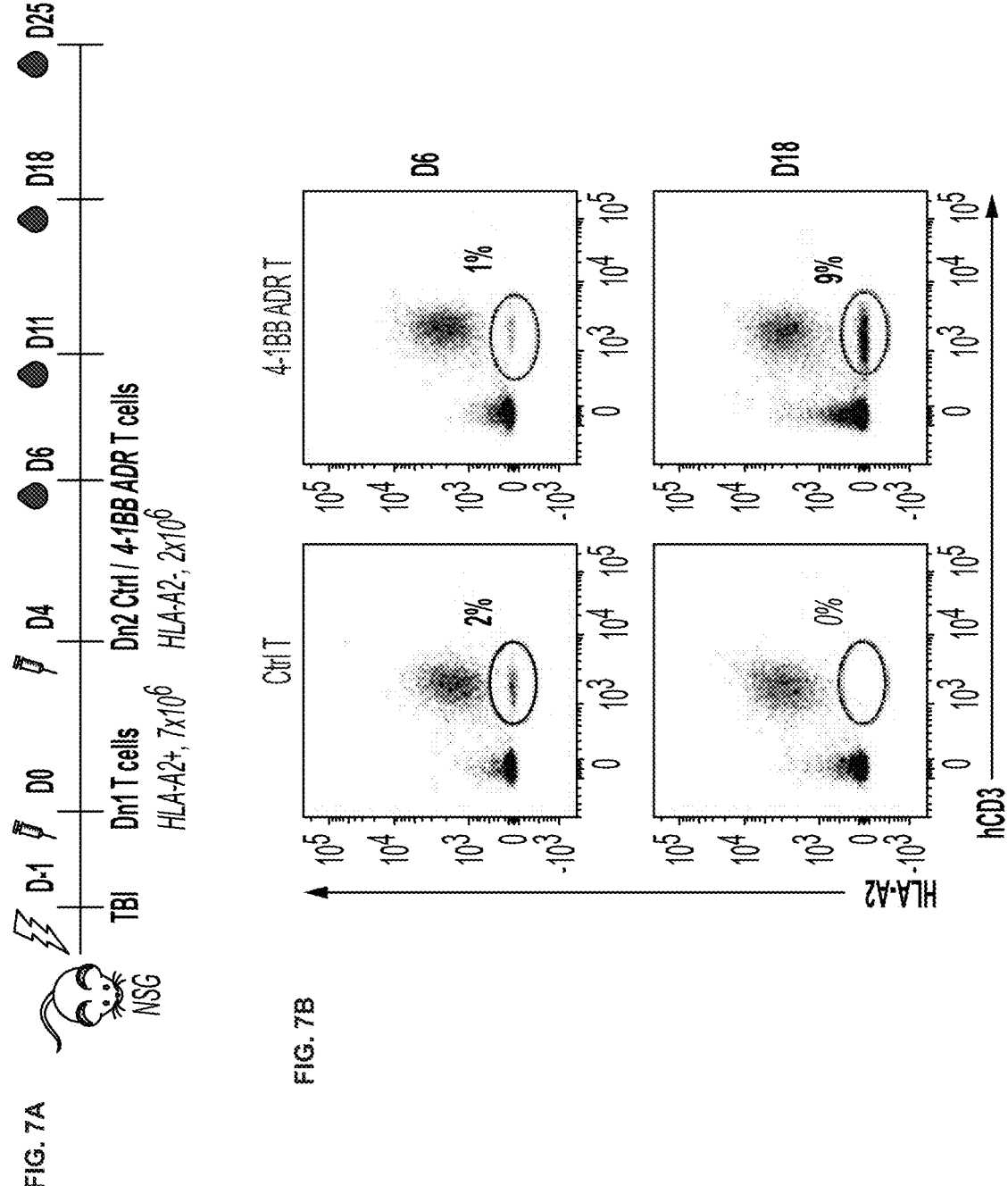

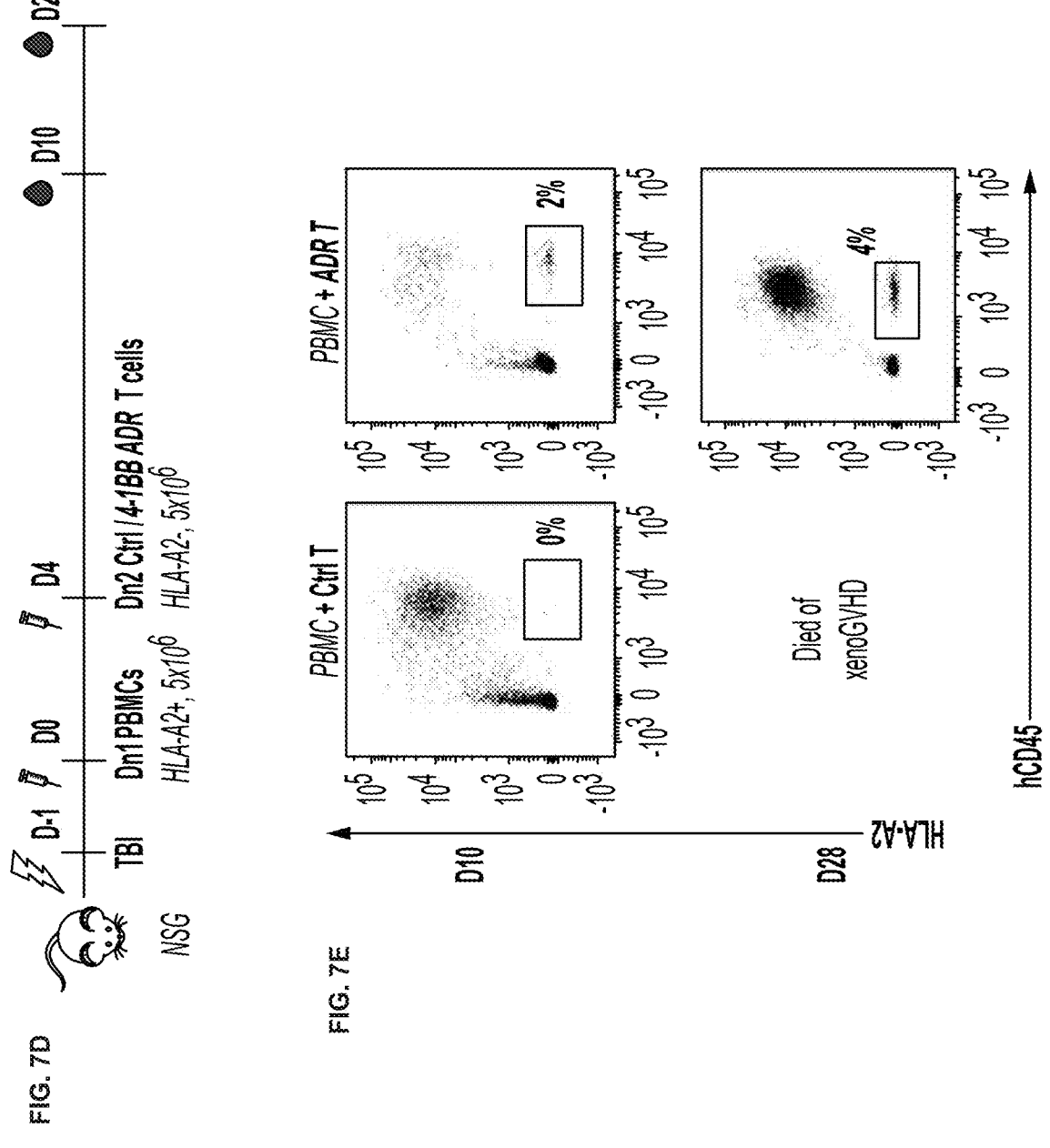

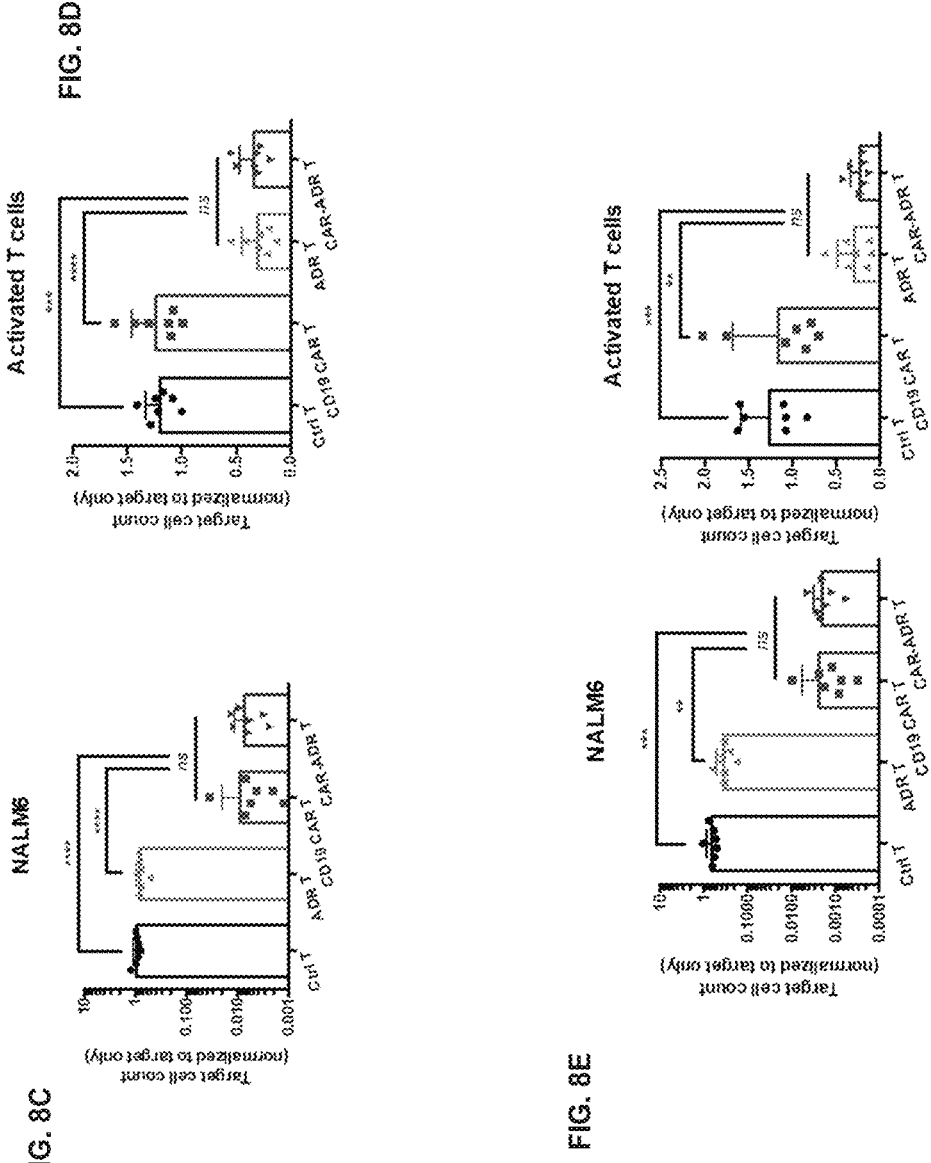

FROM

FROM

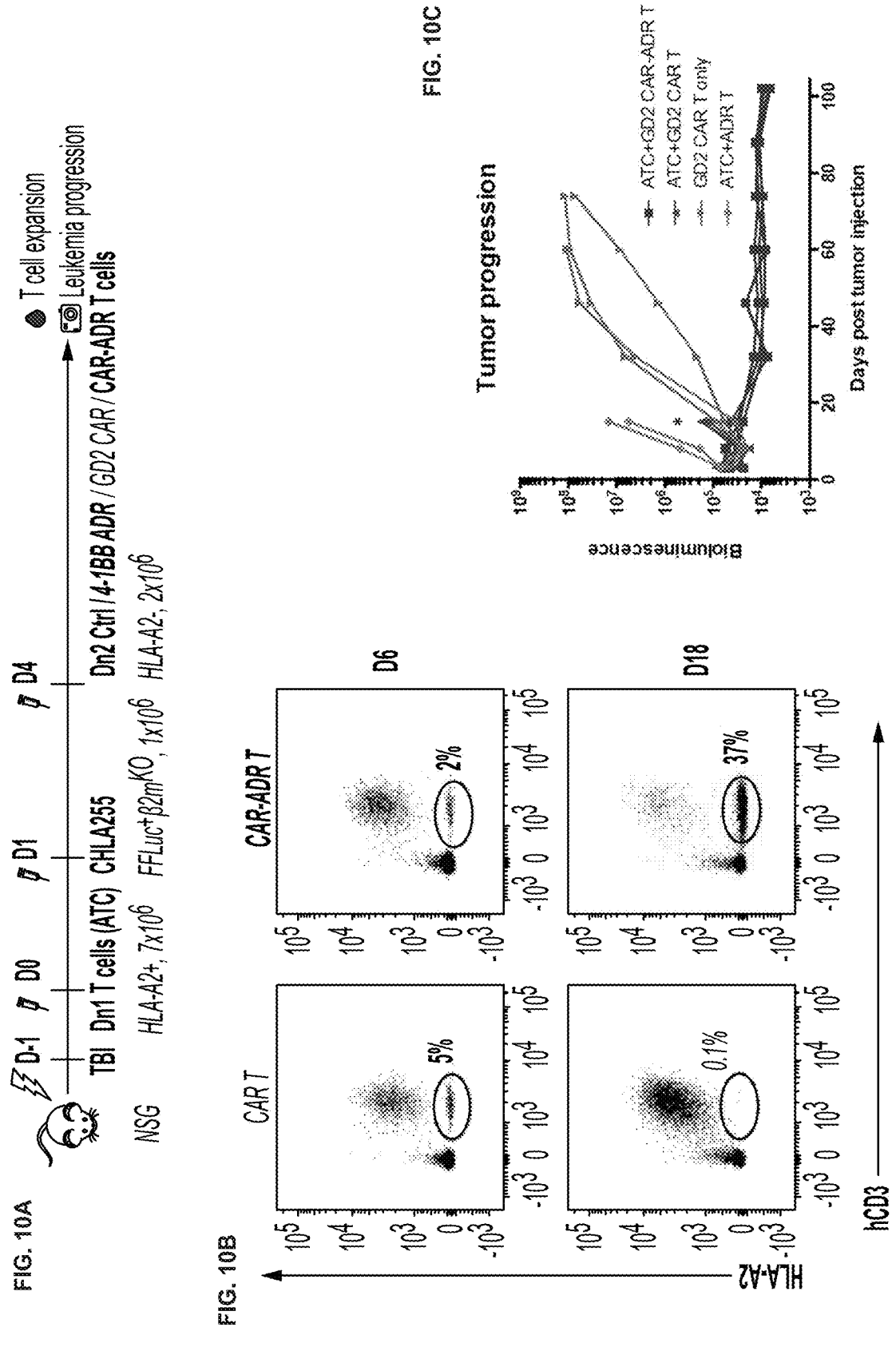

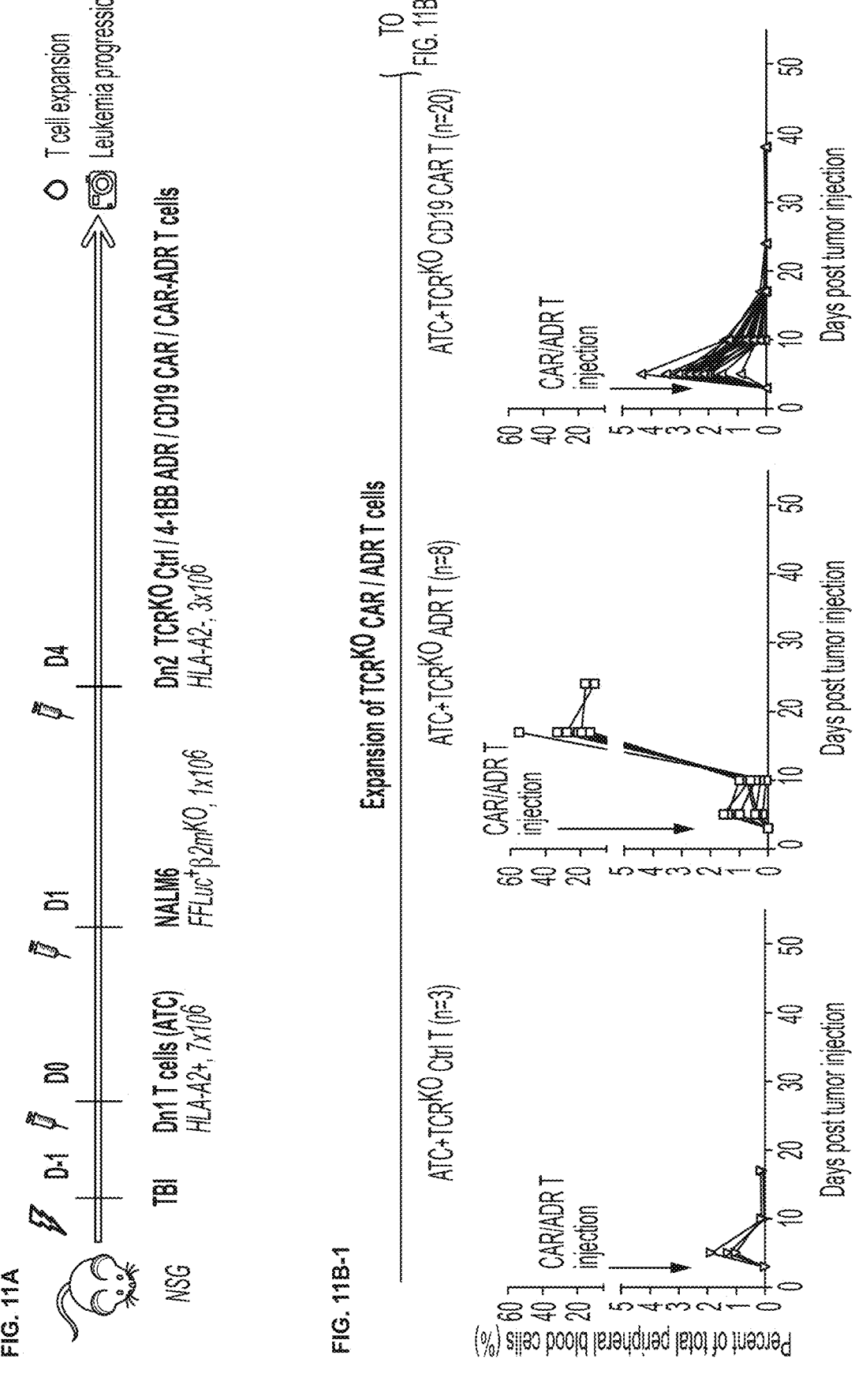

Expansion of Dn1 T cells

Leukemia progression

FROM

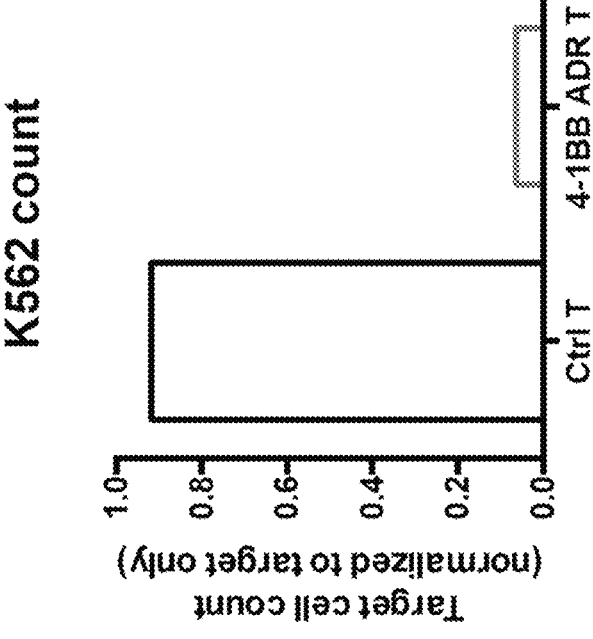
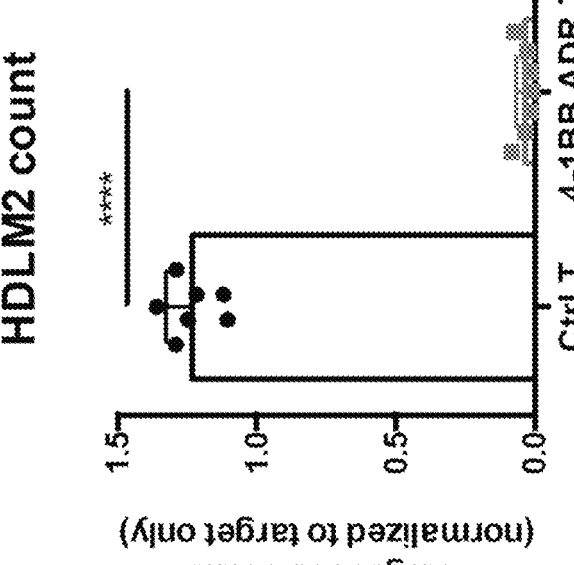
FIG. 14

SEQUENCE LISTING

```
<160> NUMBER OF SEQ ID NOS: 3

<210> SEQ ID NO 1
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Glu Phe Gly Leu Ser Trp Leu Phe Leu Val Ala Ile Leu Lys Gly
1               5                   10                  15

Val Gln Cys Gly Leu Leu Asp Leu Arg Gln Gly Met Phe Ala Gln Leu
            20                  25                  30

Val Ala Gln Asn Val Leu Leu Ile Asp Gly Pro Leu Ser Trp Tyr Ser
        35                  40                  45

Asp Pro Gly Leu Ala Gly Val Ser Leu Thr Gly Gly Leu Ser Tyr Lys
    50                  55                  60

Glu Asp Thr Lys Glu Leu Val Val Ala Lys Ala Gly Val Tyr Tyr Val
65                  70                  75                  80

Phe Phe Gln Leu Glu Leu Arg Arg Val Val Ala Gly Glu Gly Ser Gly
                85                  90                  95

Ser Val Ser Leu Ala Leu His Leu Gln Pro Leu Arg Ser Ala Ala Gly
            100                 105                 110

Ala Ala Ala Leu Ala Leu Thr Val Asp Leu Pro Pro Ala Ser Ser Glu
            115                 120                 125

Ala Arg Asn Ser Ala Phe Gly Phe Gln Gly Arg Leu Leu His Leu Ser
    130                 135                 140

Ala Gly Gln Arg Leu Gly Val His Leu His Thr Glu Ala Arg Ala Arg
145                 150                 155                 160

His Ala Trp Gln Leu Thr Gln Gly Ala Thr Val Leu Gly Leu Phe Arg
                165                 170                 175

Val Thr Pro Glu Ile Pro Ala Gly Leu Pro Ser Pro Arg Ser Glu Glu
                180                 185                 190

Ser Lys Tyr Gly Pro Pro Cys Pro Pro Cys Pro Gly Gln Pro Arg Glu
            195                 200                 205

Pro Gln Val Tyr Thr Leu Pro Pro Ser Arg Asp Glu Leu Thr Lys Asn
    210                 215                 220

Gln Val Ser Leu Thr Cys Leu Val Lys Gly Phe Tyr Pro Ser Asp Ile
225                 230                 235                 240

Ala Val Glu Trp Glu Ser Asn Gly Gln Pro Glu Asn Asn Tyr Lys Thr
                245                 250                 255

Thr Pro Pro Val Leu Asp Ser Asp Gly Ser Phe Phe Leu Tyr Ser Lys
```

-continued

```
                 260                  265                  270

Leu Thr Val Asp Lys Ser Arg Trp Gln Gln Gly Asn Val Phe Ser Cys
        275                  280                  285

Ser Val Met His Glu Ala Leu His Asn His Tyr Thr Gln Lys Ser Leu
        290                  295                  300

Ser Leu Ser Pro Gly Lys Lys Asp Pro Lys Phe Trp Val Leu Val Val
305                  310                  315                  320

Val Gly Gly Val Leu Ala Cys Tyr Ser Leu Leu Val Thr Val Ala Phe
                 325                  330                  335

Ile Ile Phe Trp Val Arg Ser Arg Val Lys Phe Ser Arg Ser Ala Asp
                 340                  345                  350

Ala Pro Ala Tyr Gln Gln Gly Gln Asn Gln Leu Tyr Asn Glu Leu Asn
        355                  360                  365

Leu Gly Arg Arg Glu Glu Tyr Asp Val Leu Asp Lys Arg Arg Gly Arg
        370                  375                  380

Asp Pro Glu Met Gly Gly Lys Pro Arg Arg Lys Asn Pro Gln Glu Gly
385                  390                  395                  400

Leu Tyr Asn Glu Leu Gln Lys Asp Lys Met Ala Glu Ala Tyr Ser Glu
                 405                  410                  415

Ile Gly Met Lys Gly Glu Arg Arg Arg Gly Lys Gly His Asp Gly Leu
                 420                  425                  430

Tyr Gln Gly Leu Ser Thr Ala Thr Lys Asp Thr Tyr Asp Ala Leu His
        435                  440                  445

Met Gln Ala Leu Pro Pro Arg Thr Ser Ala Ala Ala Gly Gly Gly Gly
        450                  455                  460

Ser Gly Gly Gly Gly Ser Gly Gly Gly Gly Ser Met Val Ser Lys Gly
465                  470                  475                  480

Glu Glu Leu Phe Thr Gly Val Val Pro Ile Leu Val Glu Leu Asp Gly
                 485                  490                  495

Asp Val Asn Gly His Lys Phe Ser Val Ser Gly Glu Gly Glu Gly Asp
                 500                  505                  510

Ala Thr Tyr Gly Lys Leu Thr Leu Lys Phe Ile Cys Thr Thr Gly Lys
        515                  520                  525

Leu Pro Val Pro Trp Pro Thr Leu Val Thr Thr Phe Thr Tyr Gly Val
        530                  535                  540

Gln Cys Phe Ala Arg Tyr Pro Asp His Met Lys Gln His Asp Phe Phe
545                  550                  555                  560

Lys Ser Ala Met Pro Glu Gly Tyr Val Gln Glu Arg Thr Ile Phe Phe
                 565                  570                  575

Lys Asp Asp Gly Asn Tyr Lys Thr Arg Ala Glu Val Lys Phe Glu Gly
                 580                  585                  590

Asp Thr Leu Val Asn Arg Ile Glu Leu Lys Gly Ile Asp Phe Lys Glu
                 595                  600                  605

Asp Gly Asn Ile Leu Gly His Lys Leu Glu Tyr Asn Tyr Asn Ser His
        610                  615                  620

Lys Val Tyr Ile Thr Ala Asp Lys Gln Lys Asn Gly Ile Lys Val Asn
625                  630                  635                  640

Phe Lys Thr Arg His Asn Ile Glu Asp Gly Ser Val Gln Leu Ala Asp
                 645                  650                  655

His Tyr Gln Gln Asn Thr Pro Ile Gly Asp Gly Pro Val Leu Leu Pro
                 660                  665                  670

Asp Asn His Tyr Leu Ser Thr Gln Ser Lys Leu Ser Lys Asp Pro Asn
        675                  680                  685
```

```
Glu Lys Arg Asp His Met Val Leu Leu Glu Phe Val Thr Ala Ala Gly
    690             695             700

Ile Thr Leu Gly Met Asp Glu Leu Tyr Lys
705             710

<210> SEQ ID NO 2
<211> LENGTH: 675
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Glu Phe Gly Leu Ser Trp Leu Phe Leu Val Ala Ile Leu Lys Gly
1               5               10              15

Val Gln Cys Gln Val Ser His Arg Tyr Pro Arg Ile Gln Ser Ile Lys
            20              25              30

Val Gln Phe Thr Glu Tyr Lys Lys Glu Lys Gly Phe Ile Leu Thr Ser
        35              40              45

Gln Lys Glu Asp Glu Ile Met Lys Val Gln Asn Asn Ser Val Ile Ile
    50              55              60

Asn Cys Asp Gly Phe Tyr Leu Ile Ser Leu Lys Gly Tyr Phe Ser Gln
65              70              75              80

Glu Val Asn Ile Ser Leu His Tyr Gln Lys Asp Glu Glu Pro Leu Phe
                85              90              95

Gln Leu Lys Lys Val Arg Ser Val Asn Ser Leu Met Val Ala Ser Leu
            100             105             110

Thr Tyr Lys Asp Lys Val Tyr Leu Asn Val Thr Thr Asp Asn Thr Ser
            115             120             125

Leu Asp Asp Phe His Val Asn Gly Gly Glu Leu Ile Leu Ile His Gln
    130             135             140

Asn Pro Gly Glu Phe Cys Val Leu Glu Ser Lys Tyr Gly Pro Pro Cys
145             150             155             160

Pro Pro Cys Pro Gly Gln Pro Arg Glu Pro Gln Val Tyr Thr Leu Pro
            165             170             175

Pro Ser Arg Asp Glu Leu Thr Lys Asn Gln Val Ser Leu Thr Cys Leu
            180             185             190

Val Lys Gly Phe Tyr Pro Ser Asp Ile Ala Val Glu Trp Glu Ser Asn
            195             200             205

Gly Gln Pro Glu Asn Asn Tyr Lys Thr Thr Pro Pro Val Leu Asp Ser
    210             215             220

Asp Gly Ser Phe Phe Leu Tyr Ser Lys Leu Thr Val Asp Lys Ser Arg
225             230             235             240

Trp Gln Gln Gly Asn Val Phe Ser Cys Ser Val Met His Glu Ala Leu
                245             250             255

His Asn His Tyr Thr Gln Lys Ser Leu Ser Leu Ser Pro Gly Lys Lys
            260             265             270

Asp Pro Lys Phe Trp Val Leu Val Val Val Gly Gly Val Leu Ala Cys
            275             280             285

Tyr Ser Leu Leu Val Thr Val Ala Phe Ile Ile Phe Trp Val Arg Ser
    290             295             300

Arg Val Lys Phe Ser Arg Ser Ala Asp Ala Pro Ala Tyr Gln Gln Gly
305             310             315             320

Gln Asn Gln Leu Tyr Asn Glu Leu Asn Leu Gly Arg Arg Glu Glu Tyr
```

```
                     325                 330                 335

Asp Val Leu Asp Lys Arg Arg Gly Arg Asp Pro Glu Met Gly Gly Lys
             340                 345                 350

Pro Arg Arg Lys Asn Pro Gln Glu Gly Leu Tyr Asn Glu Leu Gln Lys
             355                 360                 365

Asp Lys Met Ala Glu Ala Tyr Ser Glu Ile Gly Met Lys Gly Glu Arg
             370                 375                 380

Arg Arg Gly Lys Gly His Asp Gly Leu Tyr Gln Gly Leu Ser Thr Ala
385                 390                 395                 400

Thr Lys Asp Thr Tyr Asp Ala Leu His Met Gln Ala Leu Pro Pro Arg
                 405                 410                 415

Thr Ser Ala Ala Ala Gly Gly Gly Gly Ser Gly Gly Gly Gly Ser Gly
                 420                 425                 430

Gly Gly Gly Ser Met Val Ser Lys Gly Glu Glu Leu Phe Thr Gly Val
                 435                 440                 445

Val Pro Ile Leu Val Glu Leu Asp Gly Asp Val Asn Gly His Lys Phe
             450                 455                 460

Ser Val Ser Gly Glu Gly Glu Gly Asp Ala Thr Tyr Gly Lys Leu Thr
465                 470                 475                 480

Leu Lys Phe Ile Cys Thr Thr Gly Lys Leu Pro Val Pro Trp Pro Thr
                 485                 490                 495

Leu Val Thr Thr Phe Thr Tyr Gly Val Gln Cys Phe Ala Arg Tyr Pro
                 500                 505                 510

Asp His Met Lys Gln His Asp Phe Phe Lys Ser Ala Met Pro Glu Gly
                 515                 520                 525

Tyr Val Gln Glu Arg Thr Ile Phe Phe Lys Asp Asp Gly Asn Tyr Lys
             530                 535                 540

Thr Arg Ala Glu Val Lys Phe Glu Gly Asp Thr Leu Val Asn Arg Ile
545                 550                 555                 560

Glu Leu Lys Gly Ile Asp Phe Lys Glu Asp Gly Asn Ile Leu Gly His
                 565                 570                 575

Lys Leu Glu Tyr Asn Tyr Asn Ser His Lys Val Tyr Ile Thr Ala Asp
                 580                 585                 590

Lys Gln Lys Asn Gly Ile Lys Val Asn Phe Lys Thr Arg His Asn Ile
             595                 600                 605

Glu Asp Gly Ser Val Gln Leu Ala Asp His Tyr Gln Gln Asn Thr Pro
             610                 615                 620

Ile Gly Asp Gly Pro Val Leu Leu Pro Asp Asn His Tyr Leu Ser Thr
625                 630                 635                 640

Gln Ser Lys Leu Ser Lys Asp Pro Asn Glu Lys Arg Asp His Met Val
                 645                 650                 655

Leu Leu Glu Phe Val Thr Ala Ala Gly Ile Thr Leu Gly Met Asp Glu
                 660                 665                 670

Leu Tyr Lys
         675
```

```
<210> SEQ ID NO 3
<211> LENGTH: 716
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3
```

-continued

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
                35                  40                  45

Ser Asp Cys Thr Glu Phe Thr Glu Thr Glu Cys Leu Pro Cys Gly Glu
        50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
                100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
        130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
                180                 185                 190

Arg Glu Ser Lys Tyr Gly Pro Pro Cys Pro Pro Cys Pro Gly Gln Pro
        195                 200                 205

Arg Glu Pro Gln Val Tyr Thr Leu Pro Pro Ser Arg Asp Glu Leu Thr
        210                 215                 220

Lys Asn Gln Val Ser Leu Thr Cys Leu Val Lys Gly Phe Tyr Pro Ser
225                 230                 235                 240

Asp Ile Ala Val Glu Trp Glu Ser Asn Gly Gln Pro Glu Asn Asn Tyr
                245                 250                 255

Lys Thr Thr Pro Pro Val Leu Asp Ser Asp Gly Ser Phe Phe Leu Tyr
                260                 265                 270

Ser Lys Leu Thr Val Asp Lys Ser Arg Trp Gln Gln Gly Asn Val Phe
        275                 280                 285

Ser Cys Ser Val Met His Glu Ala Leu His Asn His Tyr Thr Gln Lys
        290                 295                 300

Ser Leu Ser Leu Ser Pro Gly Lys Lys Asp Pro Lys Phe Trp Val Leu
305                 310                 315                 320

Val Val Val Gly Gly Val Leu Ala Cys Tyr Ser Leu Leu Val Thr Val
                325                 330                 335

Ala Phe Ile Ile Phe Trp Val Arg Ser Arg Val Lys Phe Ser Arg Ser
                340                 345                 350

Ala Asp Ala Pro Ala Tyr Gln Gln Gly Gln Asn Gln Leu Tyr Asn Glu
        355                 360                 365

Leu Asn Leu Gly Arg Arg Glu Glu Tyr Asp Val Leu Asp Lys Arg Arg
        370                 375                 380

Gly Arg Asp Pro Glu Met Gly Gly Lys Pro Arg Arg Lys Asn Pro Gln
385                 390                 395                 400

Glu Gly Leu Tyr Asn Glu Leu Gln Lys Asp Lys Met Ala Glu Ala Tyr
                405                 410                 415

Ser Glu Ile Gly Met Lys Gly Glu Arg Arg Arg Gly Lys Gly His Asp
```

-continued

```
               420               425               430

Gly Leu Tyr Gln Gly Leu Ser Thr Ala Thr Lys Asp Thr Tyr Asp Ala
        435               440               445

Leu His Met Gln Ala Leu Pro Pro Arg Thr Ser Ala Ala Ala Gly Gly
    450               455               460

Gly Gly Ser Gly Gly Gly Gly Ser Gly Gly Gly Gly Ser Met Val Ser
465               470               475               480

Lys Gly Glu Glu Leu Phe Thr Gly Val Val Pro Ile Leu Val Glu Leu
            485               490               495

Asp Gly Asp Val Asn Gly His Lys Phe Ser Val Ser Gly Glu Gly Glu
            500               505               510

Gly Asp Ala Thr Tyr Gly Lys Leu Thr Leu Lys Phe Ile Cys Thr Thr
        515               520               525

Gly Lys Leu Pro Val Pro Trp Pro Thr Leu Val Thr Thr Phe Thr Tyr
        530               535               540

Gly Val Gln Cys Phe Ala Arg Tyr Pro Asp His Met Lys Gln His Asp
545               550               555               560

Phe Phe Lys Ser Ala Met Pro Glu Gly Tyr Val Gln Glu Arg Thr Ile
            565               570               575

Phe Phe Lys Asp Asp Gly Asn Tyr Lys Thr Arg Ala Glu Val Lys Phe
            580               585               590

Glu Gly Asp Thr Leu Val Asn Arg Ile Glu Leu Lys Gly Ile Asp Phe
            595               600               605

Lys Glu Asp Gly Asn Ile Leu Gly His Lys Leu Glu Tyr Asn Tyr Asn
    610               615               620

Ser His Lys Val Tyr Ile Thr Ala Asp Lys Gln Lys Asn Gly Ile Lys
625               630               635               640

Val Asn Phe Lys Thr Arg His Asn Ile Glu Asp Gly Ser Val Gln Leu
            645               650               655

Ala Asp His Tyr Gln Gln Asn Thr Pro Ile Gly Asp Gly Pro Val Leu
            660               665               670

Leu Pro Asp Asn His Tyr Leu Ser Thr Gln Ser Lys Leu Ser Lys Asp
        675               680               685

Pro Asn Glu Lys Arg Asp His Met Val Leu Leu Glu Phe Val Thr Ala
    690               695               700

Ala Gly Ile Thr Leu Gly Met Asp Glu Leu Tyr Lys
705               710               715
```

AUTO/ALLO-IMMUNE DEFENSE RECEPTORS FOR THE SELECTIVE TARGETING OF ACTIVATED PATHOGENIC T CELLS AND NK CELLS

This application is a national phase application under 35 U.S.C. § 371 that claims priority to International Application No. PCT/US2019/029163 filed Apr. 25, 2019, which claims priority to U.S. Provisional Patent Application 62/662,817, filed Apr. 26, 2018, both of which are incorporated by reference herein in their entirety.

STATEMENT REGARDING FEDERALLY SPONSORED RESEARCH OR DEVELOPMENT

This invention was made with government support under P50 CA126752 awarded by National Institutes of Health and the National Cancer Institute. The government has certain rights in the invention.

SEQUENCE LISTING

The instant application contains a Sequence Listing which has been submitted electronically in ASCII format and is hereby incorporated by reference in its entirety. Said ASCII copy, created on Oct. 21, 2020, is named Sequence_Listing.txt and is 18,752 bytes in size.

TECHNICAL FIELD

Embodiments of the disclosure include at least the fields of immunology, cell biology, molecular biology, and medicine.

BACKGROUND

Unwanted activation of T- and NK-cells often promotes life-threatening allo-immune reactions in patients receiving transplants or third party-derived therapeutic cells, leading to rejection of a transplanted organ/tissue or development of graft-versus-host disease (GvHD). Likewise, unwanted activation of autoreactive T-cells can lead to devastating auto-immune conditions, such as diabetes mellitus, autoimmune colitis, and multiple sclerosis. Currently, most of these diseases are not curable because of the inability to selectively eliminate pathogenic T cells. Instead, the patients are often treated with immunosuppressive drugs that render them immunodeficient and therefore susceptible to infections and malignant transformations.

The present disclosure provides solutions for a long felt need in the art of safe and effective tissue transplantation and adoptive cell transfer, including utilizing off-the-shelf cells, by enhancing their ability of the transferred cells to control pathogenic conditions because of unwanted activation of the immune system.

BRIEF SUMMARY

The present disclosure is directed to compositions and methods related to cells utilized for adoptive transfer to control pathogenic conditions due to immune activation. The composition and methods apply to autologous and allogeneic cells. Although some steps may be taken to reduce the reactivity of allogeneic cells in the recipient individual, such cells would still be targeted by the immune system of the recipient (primarily T- and NK-cells), which would recognize them as foreign leading to rejection and limiting therapeutic benefit.

The present disclosure overcomes this problem by modifying adoptive therapy cells to target activated pathogenic T, NK-T, and NK cells to prevent or treat medical conditions associated with their presence. In particular embodiments, the compositions and methods utilize adoptive T-cell transfer with cells that express receptors that selectively target pathogenic T cells while sparing resting T cells. In specific embodiments, the adoptive T-cells for transfer are engineered to express chimeric molecules that target pathogenic T cells that express certain target molecules whose presence on T cells is indicative of pathogenic T cells. In particular embodiments the disclosure concerns auto/allo-immune defense receptors (ADRs) for the selective targeting of pathogenic T-cells.

Particular embodiments of the disclosure include methods of protecting engineered allogeneic T cells from elimination in a host individual by providing to the individual cells armed with ADRs. Embodiments also include methods that avoid allo-immune reactions in individuals receiving tissue or organ transplants, for example.

In particular embodiments, cells encompassed by the disclosure have been modified or can be modified to allow them to survive in a recipient, including an allogeneic recipient. In specific cases, cells for adoptive cell therapy (including T cells, NKT cells, and so forth) are suitable for being utilized "Off-the-shelf", which herein refers to cells kept in a repository, or bank, that may be provided (with or without further modification) to an individual in need thereof for a specific purpose. The individual in many cases is not the individual from which the cells were originally derived. The cells utilized in such a manner may be pre-manufactured to express an ADR, although in some cases the cells are obtained from a bank and afterwards are modified to express an ADR. The banked cells may or may not also express a CAR or recombinant TCR, or the cells obtained from the bank may afterwards be modified to express a CAR or recombinant TCR. Such practices allow for ease of use of third party-derived therapeutic cells without immune rejection by a host and without having to manufacture a patient-specific produce every time one is needed.

In particular embodiments, there is an isolated polynucleotide, comprising sequence encoding: (1) one or more of an OX40-specific ligand, a 4-1BB-specific ligand, CD40L-specific ligand, or functional derivatives thereof; that is operably linked to (2) a signaling domain promoting T-cell activation. The polynucleotide may comprise an OX40-specific ligand, a 4-1BB-specific ligand, or a CD40L-specific ligand. The OX40-specific ligand may be OX40L, an antibody that targets OX40, an OX40L-Fc fusion, or a combination thereof, or any other engineered protein capable of specific binding to OX40. The 4-1BB-specific ligand may be 4-1BBL, an antibody that targets 4-1BB, a 4-1BBL-Fc fusion, or a combination thereof, or any other engineered protein capable of specific binding to 4-1BB. The CD40L-specific ligand may be CD40, an antibody that targets CD40L, a CD40-Fc fusion, or any other engineered protein capable of specific binding to CD40L or combination thereof. In at least certain cases, the polynucleotide further comprises sequence that encodes a spacer between (1) and (2), such as between 10 and 220 amino acids in length, for example. The spacer may have sequence that facilitates surface detection with an antibody, such as the spacer being detectable with an anti-Fc Ab. The spacer may comprise an IgG Fc portion.

In particular embodiments, polynucleotides of the disclosure may further encode a chimeric antigen receptor, a T-cell receptor, or both. The polynucleotide may be in any form including present on a vector, such as a viral vector (retroviral vector, lentiviral vector, adenoviral vector, or adeno-associated viral vector) or non-viral vector (plasmid, transposon, etc.). In particular cases, the polynucleotide is present in a cell, including a eukaryotic cell or a bacterial cell. The cell may be an immune cell, such as a T cell. The cell may be engineered. The cell may comprise one or more chimeric antigen receptors (CARs) and/or one or more engineered T cell receptors (TCRs).

Polypeptides expressed by any polynucleotide encompassed by the disclosure are included as part of the disclosure. In particular embodiments there is a polypeptide, comprising: (1) one or more of an OX40-specific ligand, a 4-1BB-specific ligand, and CD40; that is operably linked to (2) a signaling domain promoting T-cell activation. The signaling domain promoting T-cell activation may be from CD3 zeta subunit, DAP12, an Fc receptor, or a combination thereof.

Any cell encompassed by the disclosure is part of the disclosure. In specific embodiments, any chimeric receptor-expressing cell is part of the disclosure, including cells, comprising any polynucleotide contemplated herein and/or any polypeptides contemplated herein. The cell may be an engineered cell. The cell may be an immune cell, such as a T cell, including a CAR-transduced T cell and/or a T cell receptor (TCR)-transduced T cell. In specific embodiments, the cell is engineered to lack endogenous expression of one or more genes, such as lack one or more of 4-1BB, OX40 and/or CD40L. The cell may be engineered using CRISPR/Cas9, zinc finger nucleases, TALE nucleases, or meganucleases. Alternatively, the cell may be engineered to prevent surface expression of ADR ligands, for example, by trapping the ADR ligand with a specific antibody or a receptor anchored in the endoplasmic reticulum or another intracellular compartment.

In one embodiment there is a method of avoiding rejection of allogeneic cells, tissue, or organs in an individual, comprising the step of delivering to the individual an effective amount of allogeneic immune cells expressing an engineered chimeric receptor that comprises an extracellular domain that targets compounds that are selectively present on activated T cells and that comprises CD3 zeta, wherein the delivering step results in the following in the individual: (1) inhibition of endogenous alloreactive T cells in the individual; and/or (2) suppression of NK cell activation in the individual. In specific embodiments, the allogeneic cells are the allogeneic immune cells expressing the chimeric receptor. The allogeneic cells may express a chimeric antigen receptor and/or an engineered T cell receptor. The allogeneic immune cells may be delivered to the individual before, during, and/or after tissue and/or organ transplantation in the individual. In specific cases, the activated T cells are pathogenic T cells.

In one embodiment, there is a method of selectively targeting activated T cells in an individual, comprising the step of providing to the individual an effective amount of cells expressing an engineered chimeric receptor, said chimeric receptor comprising: (1) an extracellular domain that targets compounds that are selectively present on activated T cells; and (2) a signaling domain promoting T-cell activation. The signaling domain promoting T-cell activation may be derived from CD3 zeta subunit, DAP12, an Fc receptor, any ITAM-comprising sequence, or a combination thereof. In specific cases, the activated T cells are pathogenic T cells.

In a certain embodiment, there is a method of preventing or treating a medical condition related to activated T cells in an individual, comprising the step of delivering to the individual an effective amount of immune cells expressing an engineered chimeric receptor that selectively targets said activated T cells, said chimeric receptor comprising: (1) an extracellular domain that targets compounds that are selectively present on activated T cells; and (2) a signaling domain promoting T-cell activation. The medical condition may be an autoimmune disorder, such as graft rejection, graft-versus-host disease, type I diabetes, multiple sclerosis, autoimmune colitis, or a combination thereof, for example.

In one embodiment, there is a method of avoiding NK cell-mediated host rejection of allogeneic T cells, tissues, or organs in an individual, comprising the step of providing to the individual an effective amount of immune cells expressing an engineered chimeric receptor that comprises an extracellular domain that targets compounds that are selectively present on activated T cells and that also comprises a signaling domain promoting T-cell activation. The immune cells expressing the engineered chimeric receptor are the allogeneic T cells, in certain cases. The immune cells may express a chimeric antigen receptor and/or an engineered T cell receptor. The amount of immune cells expressing the engineered chimeric receptor that are provided to the individual may be in a range of $10^2$-$10^{12}$ per $m^2$. The cells expressing the chimeric receptor may be provided to the individual systemically or locally. The immune cells may be T cells. The immune cells may be delivered to the individual once or more than once.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawing, in which:

(FIG. 1A) Schematic of ADR. GFP is optional (FIG. 1B) Expression of ADR on the cell surface (FIG. 1C) Expansion of ADR T cells after transduction (FIG. 1D)

Cytotoxicity of ADR T cells against target cells expressing ADR ligands (FIG. 1E) Expansion of wild-type vs 4-1BB KO T cells expressing 4-1BB ADR and their cytotoxicity against 4-1BB+ targets showing that knocking out ADR ligand on T cells can further enhance expansion and cytotoxicity and demonstrating co-expression of ADR and its ligand on T cells is not required for ADR-T cell expansion or function FIGS. 2A-2E. Selective expression of ADR ligands on activated T cells enables their selective elimination by ADR T cells.

FIGS. 3A-3F. Expression of 4-1BB ADR protects T cells from immune rejection in an MLR model (FIG. 3A) Representative dot plots showing TCRKO T cells xo-expressing ADR are protected from rejection after coculture with allogeneic PBMC at a 1:10 ADR T:PBMC ratio. (FIG. 3B-FIG. 3C) Absolute counts of donor T cells and allogeneic T cells in the PBMC during coculture (FIG. 3D-FIG. 3F) same for virus-specific ADR T cells.

FIGS. 6A-6H. Activated NK cells upregulate ADR ligands and can be selectively targeted by ADR T cells (FIG. 6A-FIG. 6B) Expression of 4-1BB on resting vs activated NK cells (FIG. 6C) Residual counts of resting vs activated NK cells after 24 hr coculture with of 4-1BB ADR T cells (FIG. 6D) ADR T cells lacking MHC are protected from immune rejection by allogeneic PBMC by controlling the expansion of NK cells (FIG. 6E) Absolute counts of donor T cells and allogeneic NK cells during coculture. (FIG. 6F) ADR T cells lacking MHC resist immune rejection by NK cells upon 48 h coculture at a 1:1 E:T ratio. (FIG. 6G-FIG. 6H) ADR T cells control the expansion of alloreactive NK cells during MLR with PBMC, with absolute counts of NK cells plotted in H.

FIGS. 7A-7E. ADR expression protects allogeneic T cells from immune rejection in vivo (FIG. 7A) Schematic of the mouse model of immune rejection where mice were given T cells from an HLA-A2+ donor after a sublethal irradiation, followed by administration of allogeneic HLA-A2− T cells 4 days later. (FIG. 7B-FIG. 7C) Control T cells from the HLA-A2-donor were rejected by Day 18 while ADR-expressing cells were protected (FIG. 7C) Absolute counts of T cells from HLA-A2+ and HLA-A2− donors at various time points. (FIG. 7D) Modified in vivo model where instead of allogeneic T cells mice received whole PBMC (containing both T- and NK-cells) from donor 1. (FIG. 7E) Representative flow plots showing ADR T cells were protected from immune rejection and also protected mice from rapid onset of fatal GvHD.

FIGS. 8A-8E. Coexpression of CAR and ADR preserves functions of both receptors (FIG. 8A) Schematic representation of an immune cell co-expressing ADR and a CAR (FIG. 8B) Coexpression of CAR and ADR on the cell surface (FIG. 8C) Cytotoxicity of CAR-ADR T cells against NALM-6 (CD19+ CAR target) (FIG. 8D) Cytotoxicity of CAR-ADR T cells against activated T cells (ADR target) (FIG. 8E) Cytotoxic activity of CAR-ADR T cells against both targets upon simultaneous co-culture with both cell targets.

(FIG. 9B) Kinetics of T cells from Donor 2 in peripheral blood (FIG. 9C) Kinetics of Donor 1 T cells in the experimental groups (FIG. 9D) Leukemia burden in mice (FIG. 9E) overall survival of mice.

FIGS. 10A-10C. CAR-ADR T cells are protected from immune rejection and exert potent anti-tumor activity in a solid tumor model. (FIG. 10A) Schematic of the mouse model. Mice received allogeneic T cells from Donor 1 and b2mKO neuroblastoma cell line CHLA255 24 hr apart, followed by a single dose of CAR-ADR T cells from Donor 2. (FIG. 10B) Donor 2 GD2 CAR T cells were rejected by D18, whereas CAR-ADR T cells resisted allogeneic rejection and persisted in peripheral blood. (FIG. 10C) Tumor burden in mice, * indicates xenogeneic-GvHD associated deaths in ATC+GD2 CAR T group.

FIGS. 11A-11E. TCR-knockout CAR-ADR T cells are protected from immune rejection and exert potent anti-tumor activity (FIG. 11A) Schematic of the mouse model. Mice received allogeneic T cells from Donor 1 and b2mKO NALM6 24 hr apart, followed by a single dose of TCR-edited CAR-ADR T cells from Donor 2. (FIG. 11B) Kinetics of T cells from Donor 2 in peripheral blood (FIG. 11C) Kinetics of Donor 1 T cells in the experimental groups (FIG. 11D) Leukemia burden in mice (FIG. 11E) overall survival of mice.

(FIG. 13A) Structure of ADR.28zeta. (FIG. 13B-FIG. 13C) in vitro cytotoxicity of ADR.28zeta against target-expressing cell lines. (FIG. 13D-FIG. 13G) ADR.28zeta protected mice from xeno-GvHD. (FIG. 13D) Schematic of the model (FIG. 13E) Expansion of FFLuc-labeled ADR.28zeta T cells in vivo (FIG. 13F) Kinetics of weight gain/loss in mice (FIG. 13G) Overall survival of mice.

FIG. 14. Cytotoxicity of ADR-expressing cells in cancer. (left) Cytotoxicity of 4-1BB ADR-expressing T cells against HDLM-2 Hodgkin's lymphoma cells (right) Cytotoxicity of 4-1BB ADR-expressing T cells against K562 chronic myeloid leukemia (CML) cells. Absolute counts of tumor cells upon a 48 h coculture at a 1:1 effector-to-target ratio is shown.

DETAILED DESCRIPTION

Figures 1A, 1B, 1C:
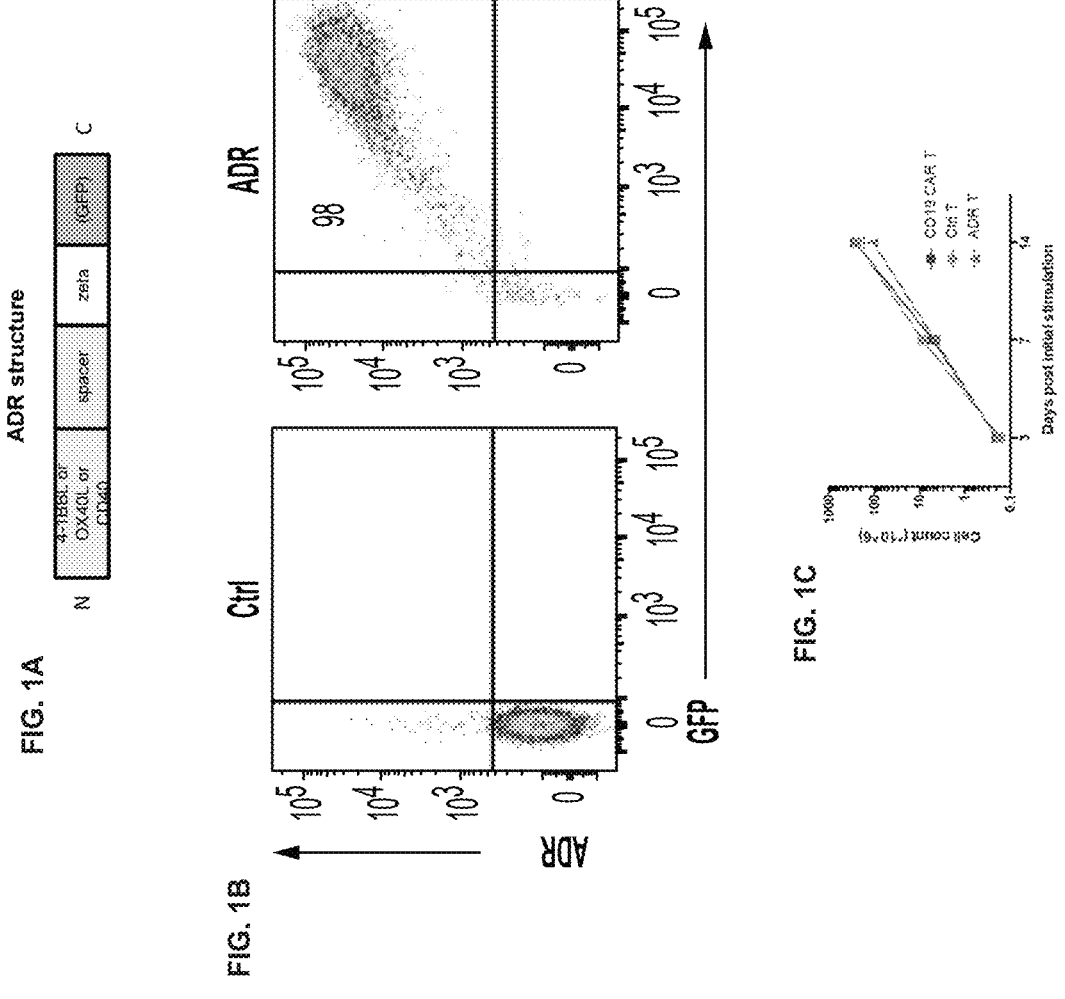
FIGS. 1A-1E. ADRs can be expressed on cell surface of immune cells and promote cytotoxicity against respective targets.

As used herein, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The term "subject," as used herein, generally refers to an individual in need of a therapy for a medical condition of any kind. A subject can be an animal of any kind. The subject can be any organism or animal subject that is an object of a method or material, including mammals, e.g., humans, laboratory animals (e.g., primates, rats, mice, rabbits), livestock (e.g., cows, sheep, goats, pigs, turkeys, and chickens), household pets (e.g., dogs, cats, and rodents), horses, and transgenic non-human animals. The subject can be a patient, e.g., have or be suspected of having a disease (that may be referred to as a medical condition), such as one or more infectious diseases, one or more genetic disorders, one or more cancers, or any combination thereof. The disease may be pathogenic. The subject may being undergoing or having undergone antibiotic treatment. The subject may be asymptomatic. The subject may be healthy individuals. The term "individual" may be used interchangeably, in at least some cases. The "subject" or "individual", as used herein, may or may not be housed in a medical facility and may be treated as an outpatient of a medical facility. The individual may be receiving one or more medical compositions via the internet. An individual may comprise any age of a human or non-human animal and therefore includes both adult and juveniles (i.e., children) and infants and includes in utero individuals. The individual may be of any race and gender. It is not intended that the term connote a need for medical treatment, therefore, an individual may voluntarily or involuntarily be part of experimentation whether clinical or in support of basic science studies.

The term "engineered" as used herein refers to a molecule that is not present in nature and has been generated by the hand of man, such as by genetic recombination techniques standard in the art.

In the context of the present disclosure, an "effective amount" or a "therapeutically effective amount" refers to the amount of cells that, when administered to an individual, allows for targeting of activated T cells and/or alleviates the signs and or symptoms of a medical condition or prevents a medical condition. The actual amount to be administered can be determined based on studies done either in vitro or in vivo where the functional immune cells exhibit pharmacological activity against a medical condition.

I. Auto/Allo-Immune Defense Receptors and Compositions and Uses Thereof

The present disclosure encompasses synthetic chimeric receptor molecules that provide for selective targeting of activated T cells, including pathogenic T cells. The engineered molecules are synthetic and may be produced by recombinant technology. The molecules may be referred to as auto/allo-immune defense receptors that target activated T cells, including activated pathogenic T cells, including with high specificity.

In particular embodiments, auto/allo-immune defense receptors (ADRs) comprise an entity that targets one or more compounds that are upregulated on activated T cells. Although the compound that is upregulated on activated T cells may be any one or combination thereof, in specific embodiments OX40, 4-1BB, and CD40L are upregulated on activated T cells and are the subjects of which the ADRs are targeting. The ADRs are present on allogeneic immune cells that are allogeneic with respect to the individual receiving the cells, in particular embodiments. In other instances, the ADRs are expressed on autologous T cells, xenogeneic cells, and/or synthetic cells.

A. Auto/Allo-Immune Defense Receptor (ADR) Molecules

ADR molecules are synthetic, non-natural, and produced by the hand of man and comprise at least (1) an extracellular domain that targets compounds that are selectively present on activated T cells (and in specific embodiments, the extracellular domain is a protein or functional fragment or derivative thereof that targets one or more compounds that are upregulated on activated T cells); that is operably linked to (2) a signaling domain promoting T-cell activation, including those derived from CD3 zeta subunit, DAP12, and Fc receptors, or another ITAM-comprising sequence, for example. The ADR molecule may comprise or consist of or consist essentially of elements (1) and (2). In at least certain cases, the ADR comprises one or more components of a Type I transmembrane protein and/or one or more components of a Type II transmembrane protein.

In specific embodiments, in the ADR molecule the extracellular domain comprises a protein that selectively binds an associated protein on an activated T cell. For example, the ADR extracellular domain may comprise a ligand for a receptor on an activated T cell, or the ADR extracellular domain may comprise a receptor for a ligand on an activated T cell.

In specific embodiments, in the ADR molecule the extracellular domain comprises a ligand for OX40, a ligand for 4-1BB, and/or CD40. These particular examples have associated proteins on activated T cells that are OX40, 4-1BB, and CD40L, respectively. In alternative embodiments, other particular compositions on the activated T cells are targeted. For example, one may target other activation markers that are upregulated on the cell surface of T cells (like CD69, CD25, CD71, etc.) can be targeted using a similar approach. In such cases, the corresponding ADR molecule would have a respective CD69, CD25, or CD71 ligand, or an antibody-derived targeting moiety, instead of 4-1BB/OX40-specific ligands.

In some cases, activated T cells are targeted that have upregulation of expression of OX40, in contrast to T cells that are not activated. To target these activated T cells, a ligand of OX40 could be utilized in the ADR to be able to target the activated T cells. In cases wherein a ligand for OX40 is utilized in the ADR, the ligand for OX40 may be any suitable ligand for OX40 including at least OX40L, an antibody (or functional fragment thereof) that binds to OX40, a fusion of Fc with OX40L, or functional derivatives or fragments thereof. OX40L may also be referred to as tumor necrosis factor (ligand) superfamily, member 4 (tax-transcriptionally activated glycoprotein 1, 34 kDa), OX40L, CD252, TNFSF4, TXGP1, OX-40L, or gp34.

In some cases, activated T cells are targeted that have upregulation of expression of 4-1BB, in contrast to T cells that are not activated. To target these activated T cells, a ligand of 4-1BB could be utilized in the ADR to be able to target the activated T cells. In cases wherein a ligand for 4-1BB is utilized in the ADR, the ligand for 4-1BB may be any suitable ligand for 4-1BB including 4-1BBL, an anti-body (or functional fragment thereof) that targets 4-1BB, a fusion of Fc with 4-1BBL, or functional derivatives or fragments thereof.

In certain cases, activated T cells are targeted that have upregulation of expression of CD40L, in contrast to T cells that are not activated. To target these activated T cells, a receptor for CD40L could be utilized in the ADR to be able to target the activated T cells. In cases wherein a receptor for CD40L is utilized in the ADR, the ADR may comprise CD40 (that may also be referred to as Bp50, CDW40, TNFRSF5, or p50), an antibody (or functional fragment thereof) that targets CD40L, or functional derivatives or fragments thereof.

In some cases, the ADR molecule comprises two or more extracellular domains to facilitate targeting of the activated T cells. Such combinations may enhance targeting of activated T cells generally or may allow for specific targeting of certain subsets of activated T cells. For example, the ADR may comprise both OX40L and 4-1BBL as extracellular domains in the same ADR molecule to allow for targeting of activated T cells that express either OX40 or 4-1BB. Such an example of a combination would selectively target activated T cells that express either OX40 or 4-1BB regardless of whether or not those activated T cells also express CD40L. Analogously, ADRs may comprise both CD40 and OX40L to target activated T cells that express either CD40L or OX40 regardless of whether or not those activated T cells also express 4-1BB.

In the ADR molecule, the extracellular domain may be operably linked to one or more components, including components that are part of the ADR molecule. One such component may be a protein that mediates downstream signaling during T cell activation. In particular embodiments the ADR comprises CD3zeta (also referred to as CD247, CD3-ZETA, CD3H, CD3Q, CD3Z, IMD25, T3Z, or TCRZ) or a functional fragment or derivative thereof. CD3zeta mediates downstream ITAM-derived signaling during T cell activation. Other ITAM-containing signaling domains may include those derived from DAP12, Fc receptors, other CD3 subunits, etc. The signaling domains may be non-covalently linked to the ADR via another domain.

In particular embodiments, the ADR comprises a spacer between the CD3 zeta and the extracellular protein that targets one or more compounds that are upregulated on activated T cells. In other cases, a spacer is not utilized. The spacer may comprise sequence that is inert or contributes substantially little or nothing with respect to any function the ADR may have, whereas in other cases the spacer comprises sequence that enhances a function of the ADR and/or allows it to be detectable and/or able to be targeted for inhibition, as examples. In specific embodiments, the spacer comprises encoded protein sequence that facilitates detection of cells that express the ADR. For example, the spacer may encode Fc region or fragments thereof that would allow for surface detection of the cells, such as using anti-Fc Abs. In particular embodiments, the spacer provides separation between the ligand binding domain and the membrane to avoid potential steric hindrances, such as those caused by the splicing of Type II transmembrane proteins (4-1BBL, OX40L) with the Type I ADR backbone (TM, signaling domains). The spacer may be of any suitable length, including about 10-220 amino acids as an example. The spacer length may be in a range of 10-220, 10-200, 10-150, 10-100, 10-50, 25-200, 25-150, 25-100, 25-75, 25-50, 50-200, 50-150, 50-125, 50-100, 50-75, 75-200, 75-150, 75-100, 100-200, 100-175, 100-150, 100-125, 125-200, 125-175, 125-150, 150-200, 150-175, 175-200, and so forth. The spacer may be about 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 130, 140, 150, 160, 170, 180, 190, 200, 210, or 220 amino acids in length. In other cases, the spacer is less than 10 amino acids or more than 200 amino acids.

In some cases, ADRs comprise one, two, three, or more costimulatory domains that enhance cytokine production from the cells that express the ADR. The costimulatory domains may be derived from the intracellular signaling domains of costimulatory proteins including CD28, CD27, 4-1BB, OX40, ICOS, CD30, HVEM, CD40, and so forth. As an example only, when the ADR comprises 4-1BBL, the costimulatory domain of the ADR may or may not be from 4-1BB.

In some embodiments, the ADRs will comprise a trans-membrane domain that may be of any kind so long as it allows the CD3 zeta component of the ADR to be located intracellularly and the extracellular domain that targets one or more compounds that are upregulated on activated T cells to be located extracellularly. In other instances, ADRs are soluble proteins that can bind to the respective ligand on activated T cells and promote cytotoxicity by crosslinking TCR (e.g., ADR-CD3 T-cell engager protein). In a case wherein the extracellular domain is from a surface protein having a transmembrane domain, (CD40, for example), the ADR may comprise the transmembrane domain from that corresponding endogenous molecule. In some cases in which the ADR molecule comprises one or more costimulatory domains, the transmembrane domain (TM) may be from the same endogenous molecule that has the costimulatory domain. Examples of TMs include those from CD3, CD8a, CD27, CD28, 4-1BB, OX40, CD4, etc.

In an example of a ADR polypeptide, the components may be in a particular N-terminal (N) to C-terminal (C) order. For a general ADR, the receptor may comprise one of the following (as examples only) and wherein the extracellular domain comprises the protein that selectively binds an associated protein on an activated T cell:

N-extracellular domain-signaling domain-C

N-extracellular domain-CD3zeta-C

N-extracellular domain-spacer-CD3zeta-C

N-extracellular domain-spacer-costimulatory domain-CD3zeta-C

N-extracellular domain-spacer-two costimulatory domains-CD3zeta-C

N-two extracellular domains-spacer-costimulatory domain-CD3zeta-C

N-two extracellular domains-spacer-two costimulatory domains-CD3zeta-C

In any case, the transmembrane domain may be C-terminal with respect to the spacer. A signal peptide at the N-terminus may be utilized to facilitate expression of Type II ligands (such as OX40L and 4-1BBL) on a Type I transmembrane protein backbone (such as the transmembrane domain, signaling domains, CD3 zeta).

In some cases, the ADR comprises one or more detectable markers, such as markers that are colorimetric, fluorescent, and/or radioactive, and so forth. Examples include green fluorescent protein, blue fluorescent protein, and so forth.

The ADR may be in the form of a polynucleotide or polypeptide expressed by a polynucleotide, although the ADR may be synthetically generated as a protein. Recombinant technology to produce ADR polynucleotides and polypeptides are known in the art.

In certain cases, a ADR polynucleotide is in an expression construct or is part of an expression construct present on a vector that may be a viral vector or a non-viral vector. Examples of non-viral vectors include plasmids. Examples of viral vectors include lentiviral, retroviral, adenoviral, and adeno-associated viral vectors. Any vector expressing the ADR will have appropriate element(s) to allow expression in an eukaryotic cell, including an immune cell, such as a T cell, NK cell, or NKT cell, for example. Such appropriate elements include promoters and so forth.

4-1BB ADR (SEQ ID NO: 1)

```
MEFGLSWLFLVAILKGVQCGLLDLRQGMFAQLVAQNVLLIDGPLSWYSDP

GLAGVSLTGGLSYKEDTKELVVAKAGVYYVFFQLELRRVVAGEGSGSVSL

ALHLQPLRSAAGAAALALTVDLPPASSEARNSAFGFQGRLLHLSAGQRLG

VHLHTEARARHAWQLTQGATVLGLFRVTPEIPAGLPSPRSEESKYGPPCP

PCPGQPREPQVYTLPPSRDELTKNQVSLTCLVKGFYPSDIAVEWESNGQP

ENNYKTTPPVLDSDGSFFLYSKLTVDKSRWQQGNVFSCSVMHEALHNHYT

QKSLSLSPGKKDPKFWVLVVVGGVLACYSLLVTVAFIIFWVRSRVKFSRS

ADAPAYQQGQNQLYNELNLGRREEYDVLDKRRGRDPEMGGKPRRKNPQEG

LYNELQKDKMAEAYSEIGMKGERRRGKGHDGLYQGLSTATKDTYDALHMQ

ALPPRTSAAAGGGGSGGGGSGGGGSMVSKGEELFTGVVPILVELDGDVNG

HKFSVSGEGEGDATYGKLTLKFICTTGKLPVPWPTLVTTFTYGVQCFARY

PDHMKQHDFFKSAMPEGYVQERTIFFKDDGNYKTRAEVKFEGDTLVNRIE

LKGIDFKEDGNILGHKLEYNYNSHKVYITADKQKNGIKVNFKTRHNIEDG

SVQLADHYQQNTPIGDGPVLLPDNHYLSTQSKLSKDPNEKRDHMVLLEFV

TAAGITLGMDELYK
```

OX40 ADR (SEQ ID NO: 2)

```
MEFGLSWLFLVAILKGVQCQVSHRYPRIQSIKVQFTEYKKEKGFILTSQK

EDEIMKVQNNSVIINCDGFYLISLKGYFSQEVNISLHYQKDEEPLFQLKK

VRSVNSLMVASLTYKDKVYLNVTTDNTSLDDFHVNGGELILIHQNPGEFC

VLESKYGPPCPPCPGQPREPQVYTLPPSRDELTKNQVSLTCLVKGFYPSD

IAVEWESNGQPENNYKTTPPVLDSDGSFFLYSKLTVDKSRWQQGNVFSCS

VMHEALHNHYTQKSLSLSPGKKDPKFWVLVVVGGVLACYSLLVTVAFIIF
```

-continued

```
WVRSRVKFSRSADAPAYQQGQNQLYNELNLGRREEYDVLDKRRGRDPEMG

GKPRRKNPQEGLYNELQKDKMAEAYSEIGMKGERRRGKGHDGLYQGLSTA

TKDTYDALHMQALPPRTSAAAGGGGSGGGGSGGGGSMVSKGEELFTGVVP

ILVELDGDVNGHKFSVSGEGEGDATYGKLTLKFICTTGKLPVPWPTLVTT

FTYGVQCFARYPDHMKQHDFFKSAMPEGYVQERTIFFKDDGNYKTRAEVK

FEGDTLVNRIELKGIDFKEDGNILGHKLEYNYNSHKVYITADKQKNGIKV

NFKTRHNIEDGSVQLADHYQQNTPIGDGPVLLPDNHYLSTQSKLSKDPNE

KRDHMVLLEFVTAAGITLGMDELYK
```

CD40L ADR (SEQ ID NO: 3)

```
MVRLPLQCVLWGCLLTAVHPEPPTACREKQYLINSQCCSLCQPGQKLVSD

CTEFTETECLPCGESEFLDTWNRETHCHQHKYCDPNLGLRVQQKGTSETD

TICTCEEGWHCTSEACESCVLHRSCSPGFGVKQIATGVSDTICEPCPVGF

FSNVSSAFEKCHPWTSCETKDLVVQQAGTNKTDVVCGPQDRLRESKYGPP

CPPCPGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNH

YTQKSLSLSPGKKDPKFWVLVVVGGVLACYSLLVTVAFIIFWVRSRVKFS

RSADAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDALH

MQALPPRTSAAAGGGGSGGGGSGGGGSMVSKGEELFTGVVPILVELDGDV

NGHKFSVSGEGEGDATYGKLTLKFICTTGKLPVPWPTLVTTFTYGVQCFA

RYPDHMKQHDFFKSAMPEGYVQERTIFFKDDGNYKTRAEVKFEGDTLVNR

IELKGIDFKEDGNILGHKLEYNYNSHKVYITADKQKNGIKVNFKTRHNIE

DGSVQLADHYQQNTPIGDGPVLLPDNHYLSTQSKLSKDPNEKRDHMVLLE

FVTAAGITLGMDELYK
```

In certain embodiments, the extracellular domain that targets activated T cells comprises an antibody or functional fragment or derivative thereof. The term "antibody," as used herein, refers to an immunoglobulin molecule that specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

In some cases, the extracellular domain of the ADR comprises an antibody fragment. The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

Synthetic antibodies may be used in the ADR. By the term "synthetic antibody" as used herein, is meant an antibody which is generated using recombinant DNA technology, such as, for example, an antibody expressed by a bacteriophage as described herein. The term should also be construed to mean an antibody that has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology that is available and well known in the art.

B. Cells Expressing ADRs

Allogeneic cells used for adoptive transfer are prone to having limited efficacy because of the immune reaction by the recipient individual. Although in some cases, the cells may be modified to remove endogenous TCR (such as with CRISPR), for example to prevent graft-versus-host disease, alternatively one can utilize virus-specific T cells (intact or CAR/TCR-modified) to retain anti-viral activity, which is useful in certain pathologic conditions. Although such VSTs have very limited graft-versus-host activity because their TCRs are more restricted to viral antigens, they are still susceptible to deleterious reaction by the recipient.

Encompassed in the disclosure are cells that are improved for allogeneic use by being modified to express a synthetic ADR molecule. Thus, the disclosure includes cells harboring the ADR as a polynucleotide and as an expressed ADR polypeptide on the surface of the cells. In particular cases, the ADR-expressing cells are produced for the purpose of being maintained in a repository for off-the-shelf use. The cells may be housed in a repository already being configured to express an ADR, or they may be housed in a bank and configured to express an ADR following retrieval from the repository. Certain cells, such as bacterial cells, may be utilized to generate the ADR molecules, whereas other cells, such as eukaryotic cells, harboring the ADR may be used for methods of the disclosure including targeting activated T cells. As shown herein, ADR-expressing immune cells selectively eliminate activated T cells and ADR-expressing immune cells are protected against cytolysis by alloreactive T cells.

Cells that express the ADR molecule may be of any kind, but in specific embodiments they are immune cells, for example immune effector cells, such as T cells, NK cells, NKT cells, or cell lines derived from the said lineages or engineered to have cytotoxic activity that have been modified to express the ADR and are therefore not found in nature. Populations of the non-natural ADR-expressing cells are contemplated, including populations that are at least 70, 75, 80, 85, 90, 91, 92, 93, 94, 95, 96, 97, 98, 99, or 100% of the population being ADR-expressing cells. The cells may be generated by standard methods of transfection or transduction of synthetic ADR polynucleotides, as an example.

In some cases, the ADR molecules that modified to express the ADR molecule may already be engineered or subsequently are engineered to have another engineered, non-natural molecule other than the ADR. For example, cells that express chimeric antigen receptors (CAR) or engineered T cell receptors (TCR) and in doing so can protect such cells against host rejection and therefore increase their therapeutic potency. Cells expressing one or more CARs and/or one or more TCRs may be engineered to express one or more ADRs, or cells that express one or more ADRs may be engineered to express one or more CARs and/or one or more TCRs. Thus, in some cases a ADR is expressed on a different vector than a CAR and/or TCR, yet in other cases a ADR molecule is expressed on the same vector as a CAR and/or TCR. In cases wherein a ADR is expressed on the same vector as a CAR (as an example), the ADR and CAR expression may be directed from the same or different regulatory elements. In any case, the ADR and CAR may be expressed as a single polypeptide with a cleavable element between them, such as 2A.

In cases wherein ADR-expressing cells also express a CAR or TCR, the CAR or TCR may target any particular antigen. In cases wherein CARs are employed, the CARs may be first generation, second generation, third generation and so on. The CAR may be bispecific, in specific cases.

In some cases, cells expressing the ADR molecules are engineered, such as engineered to lack expression of one or more endogenous molecules. In specific cases the cells are engineered to lack expression of one or more endogenous genes that would facilitate fratricide of the cells otherwise. In specific cases the cells expressing the ADR molecules are engineered to lack expression of 4-1BB or OX40, for example. Engineering of the cells may occur by CRISPR/Cas9, merely as an example.

II. Methods of Using Auto/Allo-Immune Defense Receptors

Embodiments of the disclosure include methods of providing an effective amount of ADR-expressing cells to an individual for any purpose. Methods include providing selectively targeting activated T cells in an individual for any purpose. The activated T cells are targeted by exposing activated T cells to an effective amount of ADR-expressing immune cells, such as ADR-expressing T cells. Such exposure may have one or more resultant applications, for example.

In some embodiments, the ADRs are used to selectively target activated immune cells other than activated T cells, such as B cells (that would be useful for controlling unwanted B-cell responses such as with lupus, rheumatoid arthritis, etc.), as well as targeting activation of innate immunity (such as macrophage activation syndrome, and so on). In other embodiments, the ADRs are utilized to specifically target malignant cells expressing their corresponding target, including 4-1BB or OX40 or CD40L, for example.

The regimen for providing to an individual an effective amount of ADR-expressing cells may be known or determined by an individual or individuals delivering the cells for therapy or prevention, or regardless of the method of use. In preventative cases, for example, the cells may be delivered prior to detection of one or more symptoms, or the cells may be delivered following detection of one or more symptoms but before further symptom(s) develop and/or worsen. For treatment cases, the individual may be provided the effective amount of cells after one, two, or more symptoms develop and may be after clinical diagnosis.

In specific aspects of the methods, the individual may be given a single dose of a therapeutically effective amount of cells, or the individual may be given multiple deliveries of the therapeutically effective amount of the cells, such as multiple deliveries separated by 1, 2, 3, 4, 5, 6, 7 days, or 1, 2, 3, or 4 weeks, or 1, 2, 3, 4, 5, 6, 7, 8, 9, 10, 11, or 12 months, or 1, 2, 3, 4, 5, or more years, or any range there between, for example. The time between doses may vary in a single regimen.

The administration of the ADR-expressing cells may be via any suitable route to the individual, including locally or systemically. In specific embodiments the ADR-expressing cells are delivered intravenously, orally, rectally, topically, intramuscularly, by infusion, enterically, nasally, by inhalation, sublingually, bucally, transdermally, subcutaneously, and so forth. The cells may or may not be delivered as a bolus. With multiple administrations, the cells may or may not be provided to the individual in different delivery routes. When the cells are delivered to an individual, they may be delivered in a pharmaceutically acceptable carrier or excipient. Particular examples of doses for ADR-expressing cells include $10^4$ cells/m², $10^5$ cells/m², $10^6$ cells/m², $10^7$ cells/m², $10^8$ cells/m², $10^9$ cells/m², $10^{10}$ cells/m², $10^{11}$ cells/m², or $10^{12}$ cells/m² and ranges there between.

A. Use for Off-the-Shelf Embodiments

The disclosure encompasses cells for adoptive transfer that are able to be utilized off-the-shelf, including able to be obtained from a repository for the purpose of use in an individual other than the individual from which the cells were originally obtained. The cells may already express the ADR prior to being deposited in the repository, or the cells may be modified afterwards to express the ADR. The cells may be any kind of immune effector cells for adoptive transfer. The cells prior to deposit in the repository or after obtaining them from the repository may be modified to express a tumor-specific receptor, for example (e.g., a CAR or a TCR).

As shown elsewhere herein, cells expressing ADRs selectively target activated T- and NK-cells while sparing resting subsets. The ADRs protect allogeneic T cells from immune rejection mediated by T- and/or NK-cells in vitro in addition to protecting T-cells from immune rejection in vivo. The ADRs in doing so do not interfere with the function of an engineered anti-tumor receptor (CAR, as an example) as T-cells co-expressing ADR and CAR can efficiently eliminate both tumor and activated T cells in vitro. The disclosure further provides anti-cancer activity in vivo in a mouse model using "off-the-shelf" T cells co-expressing CAR and ADR while retaining resistance to immune rejection from allogeneic T-cells present in the same mice. As an example, in FIG. 14 it is shown that 4-1BB ADR is effective against 4-1BB+ tumor cells such that ADR can be used as a therapeutic modality against 4-1BB-expressing malignancies.

In particular embodiments, "off-the-shelf" therapeutic cells express ADR to resist immune rejection and either retain endogenous TCR specificity (e.g., to viral or tumor antigens) or have endogenous TCRs replaced with engineered anti-tumor receptors, such as one or more CARs and/or one or more recombinant TCRs.

In specific embodiments, off-the-shelf cells are housed in a repository and may be modified for a specific purpose either before or after deposit in the repository. For example, ADR-expressing T cells may be housed in a repository and ready for use, such as after a tissue or organ transplant, to prevent graft rejection. ADR-expressing T cells may be housed in a repository and may be selected or engineered with a native or transgenic TCR, for example against viral infection or cancer. ADR-expressing T cells may be housed in a repository and may be transduced with a CAR directed to cancer or pathogenic infection. ADR-expressing cells may be housed in a repository and may be transduced with one or more CARs and/or one or more TCRs directed to specific cancer-associated antigens or neoantigens expressed by the patient's specific tumor.

In some cases, banked allogeneic cells are utilized for prevention of rejection of solid organ grafts by destroying rejecting host immune cells, particularly in cases when the ADR-expressing cells were not themselves alloreactive.

Although the cells that are housed in the repository may be allogeneic with respect to a recipient individual, in alternative embodiments the cells housed in the repository are autologous with respect to a recipient individual. For example, an individual with cancer may have ADR-expressing T cells deposited in a repository for subsequent use, such as in the event that the cancer comes out of remission. In other cases, autologous ADR-expressing cells are housed in a repository for treatment of autoimmune disorders.

B. Use in Autoimmune Disorders

Unwanted activation of endogenous autoreactive T cells in an individual can lead to devastating autoimmune diseases for the individual, such as diabetes mellitus, autoimmune colitis, and multiple sclerosis. In particular embodiments, one or more autoimmune disorders are prevented or treated using ADR-expressing immune cells in the individual that impacts the autoimmune disorder (or its potential development) by inhibiting endogenous autoreactive T cells in the individual. In specific embodiments, such use of the ADR-expressing cells spares resting non-pathogenic naïve and memory T cells in the individual. Thus, certain methods of the disclosure utilize particular cells modified to express ADRs that are provided to an individual in a sufficient amount to target activated T cells, including pathogenic T cells, thereby initiating destruction of the activated T cells.

In vivo activation of T cells with unwanted specificity may cause pathogenicity, and in particular embodiments cells expressing one or more ADRs target the activated T cells. In some cases, ADR-expressing cells target pathogenic cells that are a subset of activated T cells.

In particular cases, ADR-expressing T cells can be used to prevent or reverse life-threatening and debilitating conditions driven by activated T cells (organ rejection, graft-versus-host disease, type I diabetes, multiple sclerosis, autoimmune colitis, lupus, rheumatoid arthritis, as examples) using adoptive T-cell transfer with the ADR-expressing T cells.

In some cases, the ADR-expressing T cells also comprise one or more compositions other than the ADR that facilitate treatment or prevention of one or more autoimmune disorders.

In some cases, an individual being provided the ADR-expressing T cells is given one or more additional therapies to prevent or treat one or more autoimmune disorders. The individual may or may not be given one or more immunosuppressive drugs, for example, such as glucocorticoids, cytostatics, antibodies, and/or drugs acting on immunophilins. In addition or alternatively, the individual may be given one or more appropriate vaccines.

In some cases, an individual is at risk for an autoimmune disorder and is provided an effective amount of ADR-expressing cells to prevent onset of the autoimmune disorder or to delay onset and/or lessen one or more symptoms, including in severity and/or duration, for example. An individual at risk for an autoimmune disorder, for example, is one having a personal or family history, being a female of certain ethnicity, and so forth. The individual may have one autoimmune disorder and desires to prevent or reduce the severity and/or duration or delay the onset of another autoimmune disorder(s), in some cases.

Examples of autoimmune disorders that may be prevented or treated with ADR-expressing cells include at least the following: Achalasia; Addison's disease; Adult Still's disease; Agammaglobulinemia; Alopecia areata; Amyloidosis; Ankylosing spondylitis; Anti-GBM/Anti-TBM nephritis; Antiphospholipid syndrome; Autoimmune angioedema; Autoimmune dysautonomia; Autoimmune encephalomyelitis; Autoimmune hepatitis; Autoimmune inner ear disease (AIED); Autoimmune myocarditis; Autoimmune oophoritis; Autoimmune orchitis; Autoimmune pancreatitis; Autoimmune retinopathy; Autoimmune urticarial; Axonal & neuronal neuropathy (AMAN); Baló disease; Behcet's disease;

Benign mucosal pemphigoid; Bullous pemphigoid; Castleman disease (CD); Celiac disease; Chagas disease; Chronic inflammatory demyelinating polyneuropathy (CIDP); Chronic recurrent multifocal osteomyelitis (CRMO); Churg-Strauss Syndrome (CSS) or Eosinophilic Granulomatosis (EGPA); Cicatricial pemphigoid; Cogan's syndrome; Cold agglutinin disease; Congenital heart block; Coxsackie myocarditis; CREST syndrome; Crohn's disease; Dermatitis herpetiformis; Dermatomyositis; Devic's disease (neuromyelitis optica); Discoid lupus; Dressler's syndrome; Endometriosis; Eosinophilic esophagitis (EoE); Eosinophilic fasciitis; Erythema nodosum; Essential mixed cryoglobulinemia; Evans syndrome; Fibromyalgia; Fibrosing alveolitis; Giant cell arteritis (temporal arteritis); Giant cell myocarditis; Glomerulonephritis; Goodpasture's syndrome; Granulomatosis with Polyangiitis; Graves' disease; Guillain-Barre syndrome; Hashimoto's thyroiditis; Hemolytic anemia; Henoch-Schonlein purpura (HSP); Herpes gestationis or pemphigoid gestationis (PG); Hidradenitis Suppurativa (HS) (Acne Inversa); Hypogammalglobulinemia; IgA Nephropathy; IgG4-related sclerosing disease; Immune thrombocytopenic purpura (ITP); Inclusion body myositis (IBM); Interstitial cystitis (IC); Juvenile arthritis; Juvenile diabetes (Type 1 diabetes); Juvenile myositis (JM); Kawasaki disease; Lambert-Eaton syndrome; Leukocytoclastic vasculitis; Lichen planus; Lichen sclerosus; Ligneous conjunctivitis; Linear IgA disease (LAD); Lupus; Lyme disease chronic; Meniere's disease; Microscopic polyangiitis (MPA); Mixed connective tissue disease (MCTD); Mooren's ulcer; Mucha-Habermann disease; Multifocal Motor Neuropathy (MMN) or MMNCB; Multiple sclerosis; Myasthenia gravis; Myositis; Narcolepsy; Neonatal Lupus; Neuromyelitis optica; Neutropenia; Ocular cicatricial pemphigoid; Optic neuritis; Palindromic rheumatism (PR); PANDAS; Paraneoplastic cerebellar degeneration (PCD); Paroxysmal nocturnal hemoglobinuria (PNH); Parry Romberg syndrome; Pars planitis (peripheral uveitis); Parsonage-Turner syndrome; Pemphigus; Peripheral neuropathy; Perivenous encephalomyelitis; Pernicious anemia (PA); POEMS syndrome; Polyarteritis nodosa; Polyglandular syndromes type I, II, III; Polymyalgia rheumatic; Polymyositis; Postmyocardial infarction syndrome; Postpericardiotomy syndrome; Primary biliary cirrhosis; Primary sclerosing cholangitis; Progesterone dermatitis; Psoriasis; Psoriatic arthritis; Pure red cell aplasia (PRCA); Pyoderma gangrenosum; Raynaud's phenomenon; Reactive Arthritis; Reflex sympathetic dystrophy; Relapsing polychondritis; Restless legs syndrome (RLS); Retroperitoneal fibrosis; Rheumatic fever; Rheumatoid arthritis; Sarcoidosis; Schmidt syndrome; Scleritis; Scleroderma; Sjögren's syndrome; Sperm & testicular autoimmunity; Stiff person syndrome (SPS); Subacute bacterial endocarditis (SBE); Susac's syndrome; Sympathetic ophthalmia (SO); Takayasu's arteritis; Temporal arteritis/Giant cell arteritis; Thrombocytopenic purpura (TTP); Tolosa-Hunt syndrome (THS); Transverse myelitis; Type 1 diabetes; Ulcerative colitis (UC); Undifferentiated connective tissue disease (UCTD); Uveitis; Vasculitis; Vitiligo; Vogt-Koyanagi-Harada Disease; and Wegener's granulomatosis (or Granulomatosis with Polyangiitis (GPA)).

C. Use to Eliminate NK cells

ADR-expressing immune cells may be utilized to eliminate NK cells in cases wherein it is desirable to do so. As demonstrated herein, the presence of ADRs on certain immune cells provides a specific cytotoxic activity against NK cells that are involved with mediating rapid rejection of HLA$^{low}$ or HLA-mismatched cells. Thus, in situations where it is desirable to maintain HLA$^{low}$ or HLA-mismatched cells, for example to be able to utilize adoptive transfer of allogeneic cells into certain individuals, use of ADR-expressing cells avoids NK cell activation and rejection of the HLA-mismatched cells. Specifically, as shown herein, co-culture of T cells expressing ADRs leads to elimination of NK cells and thus offsets the NK cell-mediated host rejection of ADR-expressing allogeneic T cells.

D. Use to Facilitate the Engraftment of Allogeneic Cell/Tissue/Organ Transplant

In a specific aspect of avoiding activation of alloreactive T cells, one may avoid rejection of allogeneic cells, tissues, or organs in individuals receiving transplants, which is mainly mediated by a population of alloreactive T cells from the recipient. Activation of recipient's alloreactive T cells would lead to graft failure, for example, if steps were not taken to avoid such rejection. Therefore, in particular embodiments, methods of transplanting cells, tissue, or organs into an individual utilize delivery of an effective amount of ADR-expressing cells before, during, and/or after the respective transplants of cells, tissue(s), or organ(s). In some cases, the ADR-expressing cells are not themselves part of the cells, tissue(s), or organ(s) that are the subject of the transplant, whereas in other cases the ADR-expressing cells are part of the respective cells, tissue(s), or organ(s).

Tissue for transplantation may be of any kind including at least skin, cornea, bone, tendons, heart valves, veins, or arteries, for example. Organ for transplantation may be of any kind, including heart, kidneys, liver, lungs, pancreas, intestine, and thymus, for example.

In particular embodiments, ADR-expressing cells enhance allogeneic cell use in an individual as a two-pronged approach: (1) they inhibit the endogenous alloreactive T-cells in the individual; and (2) they suppress NK cell-mediated rejection in the individual. As such, the ADR molecules can enhance the persistence and activity of any type of third party-derived therapeutic cells in the individual including, for example, allogeneic therapeutic cells, including T-cells, NK cells, NK-T cells, mucosal associated invariant T cells (MAIT) and other cytotoxic cells, including those expressing engineered constructs such as chimeric antigen receptor (CAR), transgenic TCR, etc.

E. Use in Prophylaxis or Treatment of Graft-Versus-Host Disease (GvHD) During Allogeneic Cell/Tissue/Organ Transplant In another specific aspect of avoiding activation of alloreactive T cells, one may avoid life-threatening allo-immune reactions in individuals receiving transplants of allogeneic cells, tissues, or organs. Such transplants would contain donor alloreactive T cells that would elicit development of graft-versus-host disease (GvHD), for example, if steps were not taken to avoid their activation. Therefore, in particular embodiments, methods of transplanting cells, tissue, or organs into an individual utilize delivery of an effective amount of ADR-expressing cells before, during, and/or after the respective transplants of cells, tissue(s), or organ(s). In some cases, the ADR-expressing cells are not themselves part of the cells, tissue(s), or organ(s) that are the subject of the transplant, whereas in other cases the ADR-expressing cells are part of the respective cells, tissue(s), or organ(s).

Tissue for transplantation may be of any kind including at least skin, cornea, bone, tendons, heart valves, veins, or arteries, for example. Organ for transplantation may be of any kind, including heart, kidneys, liver, lungs, pancreas, intestine, and thymus, for example.

III. Production of ADR-Expressing Cells

Cells expressing the ADR molecules may be produced in a variety of ways, all of which may be routine in the art. The production methods may include obtaining the cells to be modified to express the ADR molecule and also include generation of the ADR molecules.

A. Sources of T Cells

Prior to expansion and genetic modification of the ADR-expressing T cells of the disclosure, a source of T cells may be obtained from a subject. Such a step of obtaining may or may not be part of the method. In some cases, obtaining T cells to be modified and their manipulation may be performed by a party other than the party that provides the ADR expressing-T cells to an individual. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present disclosure, any number of T cell lines available in the art may be used. In certain embodiments, T cells can be obtained from a unit of blood collected from a subject using any number of techniques known to the skilled artisan, such as Ficoll™ separation. In one embodiment, cells from the circulating blood of an individual are obtained by apheresis. The apheresis product typically contains lymphocytes, including T cells, monocytes, granulocytes, B cells, other nucleated white blood cells, red blood cells, and platelets, for example. In one embodiment, the cells collected by apheresis may be washed to remove the plasma fraction and to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly re-suspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. In another embodiment, it may be desirable to use lower concentrations of cells. By significantly diluting the mixture of T cells and surface (e.g., particles such as beads), interactions between the particles and cells is minimized.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. Many freezing solutions and parameters are known in the art. In certain embodiments, cryopreserved cells are thawed and washed as described herein and allowed to rest for one hour at room temperature prior to activation using the methods of the present invention.

Also contemplated in the context of the disclosure is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAM-PATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin)

(Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

B. Activation and Expansion of T Cells

Whether prior to or after genetic modification of the T cells to express the ADR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. Generally, the T cells of the disclosure are expanded by contact with a surface having attached thereto an agent that stimulates a CD3/TCR complex associated signal and a ligand that stimulates a co-stimulatory molecule on the surface of the T cells. Such processes are known in the art. In other instances, T cells can be modified to express ADR without prior activation.

C. Generation of ADR Molecules

Turning generally to polynucleotides that encode the ADR, the nucleic acid sequences coding for the ADR molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the ADR polynucleotide of interest can be produced synthetically, rather than cloned.

In brief summary, the expression of synthetic polynucleotides encoding ADRs is typically achieved by operably linking a nucleic acid encoding the ADR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The ADR polynucleotide can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral-based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1alpha (EF-1 alpha). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of an ADR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing ADR polynucleotides into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a ADR polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). One method for the introduction of a polynucleotide into a host cell is calcium phosphate transfection.

Biological methods for introducing a ADR polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about –20.degree. C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

In some instances, the ADR molecules may be integrated into an endogenous nucleic acid of the cells. One may have a target site for homologous recombination, where it is desired that a construct be integrated at a particular locus. For example) can knock-out an endogenous gene and replace it (at the same locus or elsewhere) with the gene encoded for by the construct using materials and methods as are known in the art for homologous recombination. For homologous recombination, one may use either OMEGA or 0-vectors. CRISPR/Cas9, zinc finger nucleases, TALE nucleases, meganucleases, and other site directed nucleases may be used to target and cleave a specific site in the genome to promote homologous recombination.

The exemplary T cells that have been engineered to include the ADR-expressing construct(s) may be grown in culture under selective conditions and cells that are selected as having the construct may then be expanded and further analyzed, using, for example; the polymerase chain reaction for determining the presence of the construct in the host cells. Once the engineered host cells have been identified, they may then be used as planned, e.g. expanded in culture or introduced into a host organism.

Depending upon the nature of the cells, the cells may be introduced into a host organism, e.g. a mammal, in a wide variety of ways. The cells may be introduced at the site of the tumor, in specific embodiments, although in alternative embodiments the cells home to the cancer or are modified to home to the infected tissue. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium.

The DNA introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

EXAMPLES

The following examples are presented in order to more fully illustrate particular embodiments of the disclosure. They should in no way, however, be construed as limiting the broad scope of the disclosure.

Example 1

Auto/Allo-Immune Defense Receptors for the Selective Targeting of Pathogenic T Cells Disclosed herein is a novel approach to specifically target pathogenic T cells using auto/allo-immune defense receptors (ADRs) expressed on normal T cells. ADR-expressing T cells find and eliminate only activated T cells and spare resting non-pathogenic naïve and memory T cells, which constitute the majority of circulating lymphocytes The concept of the ADR-mediated targeting is based on the observation that within 24 h of activation, T cells transiently upregulate costimulatory genes 4-1BB, OX40, and/or CD40L on their cell surface. The expression of 4-1BB, OX40, and/or CD40L is only maintained when the T-cells are actively cytotoxic and is gradually downregulated within 4-5 days, when TCR signaling has stopped. Notably, activated CD8$^+$ T cells showed higher magnitude of 4-1BB expression whereas CD4$^+$ T cells preferentially expressed OX40 and/or CD40L. Apart from activated T cells, ADR ligands may only be expressed on activated NK cells and on some other non-critical and replenishable subsets of cells. The pattern of expression of 4-1BB, OX40, and CD40L makes these genes attractive targets to target activated cells with high specificity while avoiding permanently damaging critical immune and non-immune tissues.

To explore the feasibility of targeting these activated T cells, auto/allo-immune defense receptors (ADRs) were designed to comprise of a 4-1BB- or OX40-specific ligand, or a CD40L-specific receptor directly connected via a spacer to a CD3 chain encoded in a gammaretroviral vector SFG. The spacer region was incorporated a) to enable integration of type II proteins 4-1BBL and OX40L into the Type I backbone of the ADR and b) to facilitate detection of ADR on the cell surface by FACS staining. Transduction of T cells with this construct efficiently forced ADR expression on the cell surface. These ADR T cells had potent and robust cytotoxicity against 4-1BB-, OX40-, and CD40L-expressing cells, eliminating 90-99% of the target cells within 48 h. These results demonstrate the feasibility of generating functional 4-1BB-, OX40-, and CD40L-specific ADR T cells.

Because ADR signaling in T cells in turn upregulates 4-1BB, OX40, and CD40L, thus promoting fratricide and impeding effector cell expansion, the effects of CRISPR/Cas9 genomic disruption of ADR target genes in the effector T cells were explored. The inventors had previously shown that this CRISPR/Cas9 approach can prevent fratricide of primary human T cells expressing a CD7-specific CAR. In this context, with CRISPR/Cas9 the inventors were able to knock out 4-1BB expression in ~70% of ADR T cells that consistently increased ADR T cell expansion >2-fold at 48 h following coculture with 4-1BB$^+$ target cells without affecting the cytotoxicity.

Next, the ability of ADR T cells was tested to selectively eliminate activated T cells. 4-1BB, OX40, and CD40L ADR T cells were co-cultured with fluorescently labeled resting or CD3/CD28 activated T cells. Residual live CD4+ and CD8$^+$ T cells were quantified by flow cytometry with counting beads. There was no reactivity against resting autologous T cells after 72 h of co-culture with T cells expressing 4-1BB-, OX40-, or CD40L-specific ADR$^+$ (FIG. 2B). In contrast, co-culture of 4-1BB ADR T cells with CD3/CD28-activated T cells eliminated most CD8$^+$ and some CD4$^+$ T cells within 48 h. Incubation with OX40 ADR T cells resulted in a reciprocal high-level depletion of activated CD4$^+$ T cells and modest depletion of activated CD8$^+$ T cells. CD40L ADR T cells produced moderate cytotoxic effect on activated CD4$^+$ T cells yet no effect was seen on CD8$^+$ T cells. The differential targeting profiles of OX40, CD40L and 4-1BB ADR T cells against activated CD4$^+$ and CD8$^+$ T cells correlates with observed differences in the magnitude and kinetics of OX40, CD40L and 4-1BB expression on each T cell subset. This property of ADRs can be utilized to preferentially target either or both subsets of allo- or auto-reactive T cells according to need. Therefore, ADR expression enables T cells to specifically target activated (pathogenic) T cells but spare resting cells, suggesting their clinical use.

It was assessed whether virus-specific T cells (VST) expressing ADRs can resist allogeneic rejection in an in vitro mixed lymphocyte reaction (MLR) assay. CMV-specific T cells were generated from an HLA-A2-negative donor and mixed control non-transduced or ADR-transduced VST with alloreactive HLA-A2$^+$ PBMC at a 1:2 cell-to-cell ratio. The inventors then cultured the cells for 12 days. At the end of co-culture, control VSTs were almost completely eliminated by HLA-A2$^+$ PBMC whereas VSTs expressing either 4-1BB ADR or OX40 ADR resisted rejection. Taken together, these results demonstrate the feasibility and selectivity of targeting activated T cells using the newly developed ADR platform embodiment.

Example 2

Auto/Allo-Immune Defense Receptors for the Selective Targeting of Nk Cells

The ADRs demonstrate a specific cytotoxic activity against NK cells, a key cell population mediating rapid rejection of HLA$^{low}$ or HLA-mismatched cells.

NK cells are capable of recognizing HLA-mismatched cells or cells with low HLA expression, as a part of the anti-tumor and anti-viral immune surveillance. Adoptive transfer of allogeneic cells into immunoreplete patients would thus result in NK-cell activation and rejection of the HLA-mismatched cells. Here, it is shown that co-culture of T cells expressing 4-1BB- and OX40-specific auto/allo-immune defense receptors (ADRs) leads to elimination of NK cells and thus would offset the NK cell-mediated host rejection of ADR-armed allogeneic T cells. Therefore, ADRs do not only inhibit the alloreactive T-cell response but also suppress NK cell mediated rejection, further supporting the application of ADRs to enhance the persistence and activity of "off-the-shelf" therapeutic T cells.

Example 3

ADR-Expressing T Cells Eliminate Target Cells

Figure 1D:
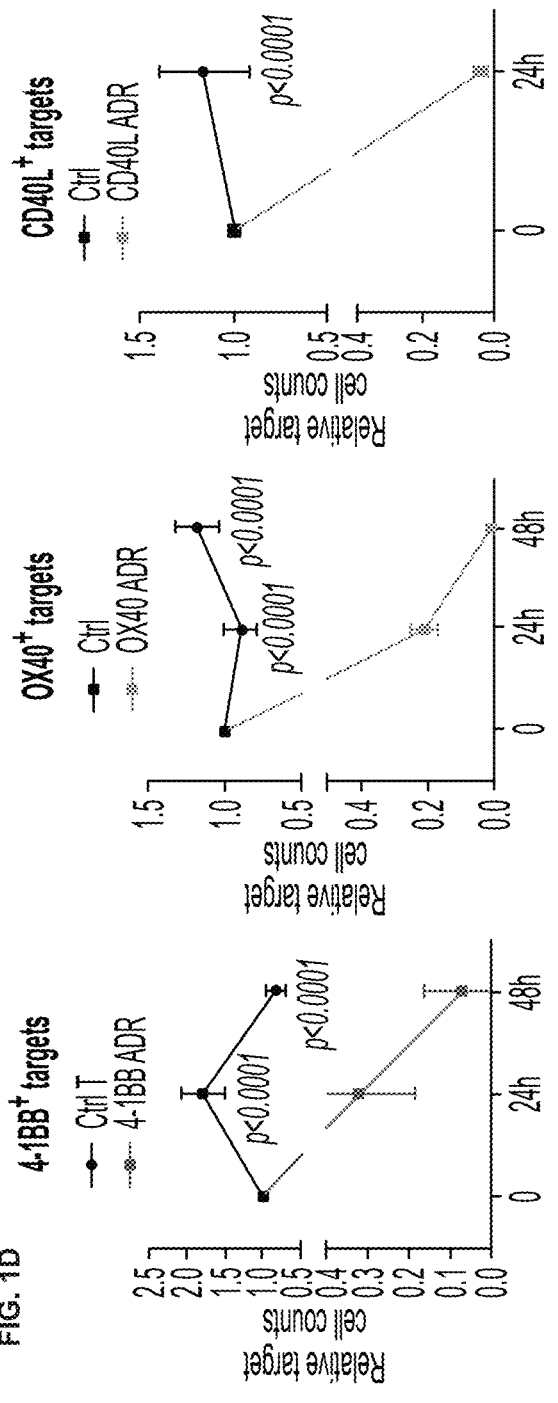
Figure 1E:
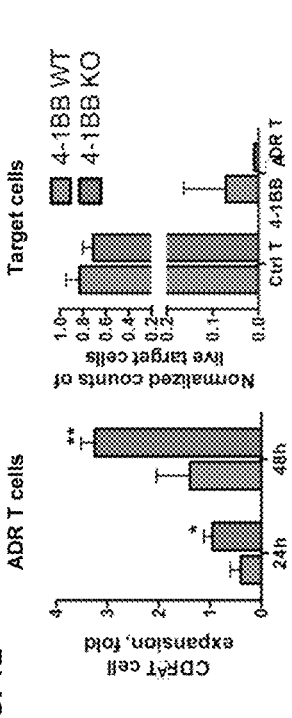

ADRs can be expressed on cell surface of immune cells and promote cytotoxicity against respective targets. FIG. 1A illustrates one example of a schematic of ADR (a label such as GFP is optional). The expression of ADR on the surface of T cells was confirmed (FIG. 1B) and the cells were expanded commensurate with controls (FIG. 1C). (FIG. 1D) The ADR-expressing T cells were cytotoxicity against target cells expressing corresponding ADR ligands (FIG. 1D). FIG. 1E demonstrates expansion of wild-type vs 4-1BB KO T cells expressing 4-1BB ADR and their cytotoxicity against 4-1BB+ targets. Knocking out the ADR ligand on T cells can further enhance expansion and cytotoxicity, and co-expression of ADR and its ligand on T cells is not required for ADR-T cell expansion or function (FIG. 1E).

Figure 2A:
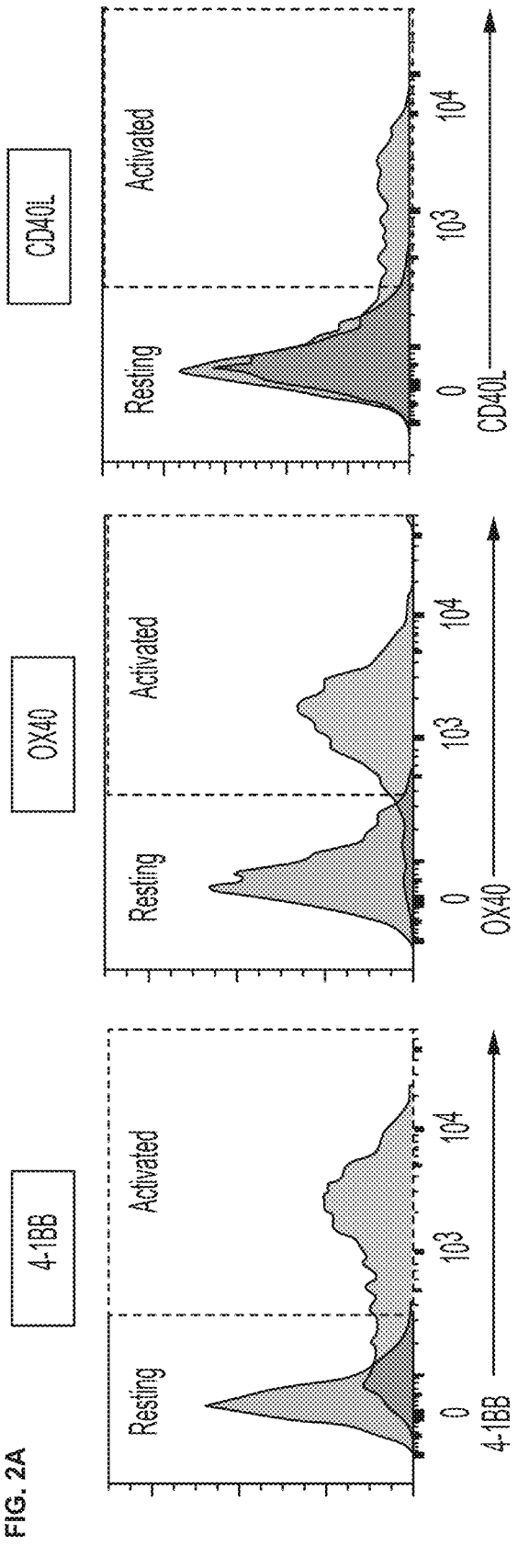
(FIG. 2A-FIG. 2C) Expression of ADR ligands on resting vs activated T cells after TCR stimulation.
Figure 2D:
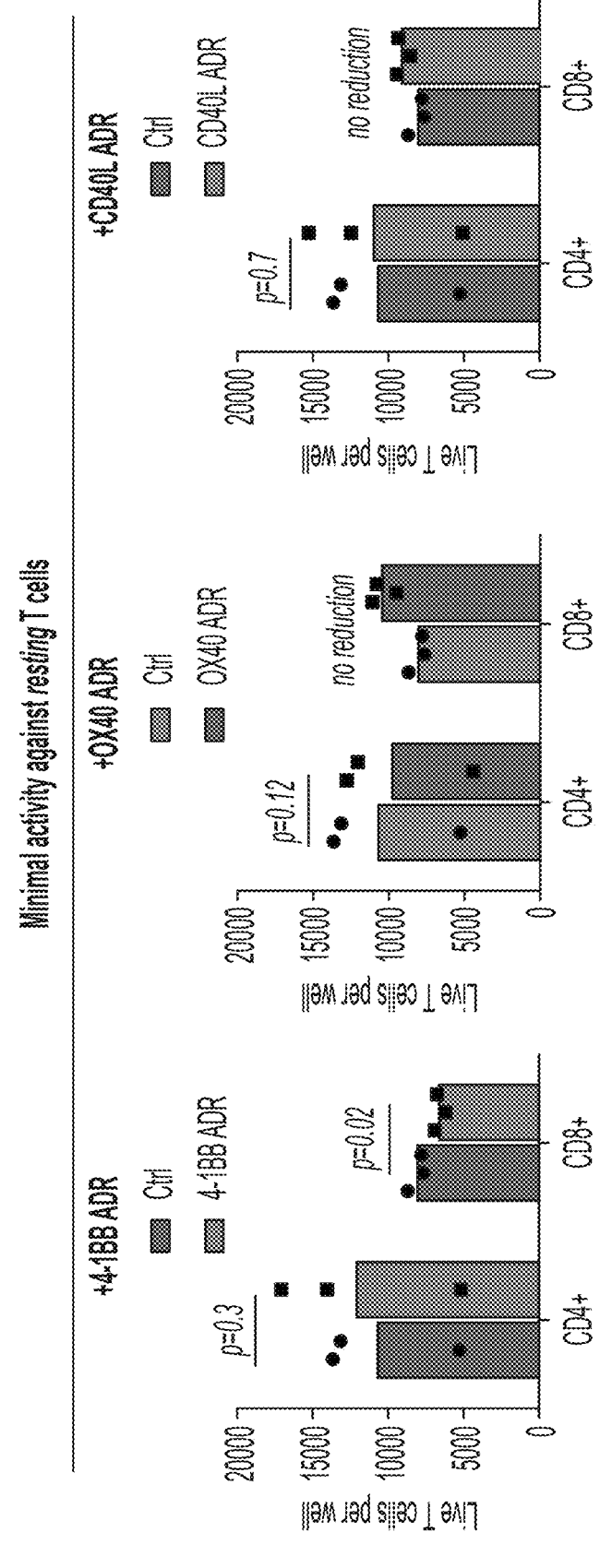
(FIG. 2D) Absence of cytotoxicity of ADR T cells against resting CD4+ and CD8+ T cells (FIG. 2E) Elimination of activated CD4+ and CD8+ T cells by ADR T cells after a 48 h coculture.
Figure 2E:
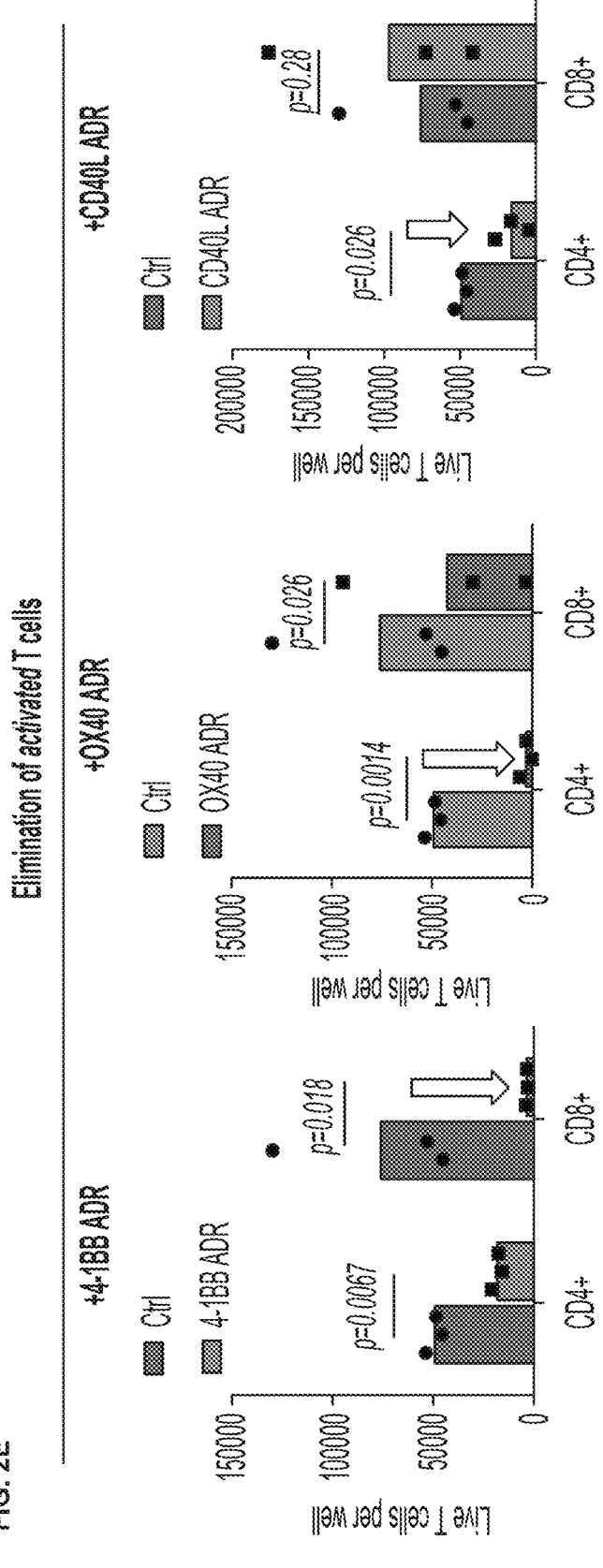

Selective expression of ADR ligands on activated T cells enables their selective elimination by ADR T cells. Expression of ADR ligands on resting vs activated T cells after TCR stimulation is determined (FIG. 2A-FIG. 2C). There was no cytotoxicity of ADR T cells against resting CD4+ and CD8+ T cells (FIG. 2D), yet there was elimination of activated CD4+ and CD8+ T cells by ADR T cells after a 48 h co-culture (FIG. 2E).

Figure 3B:
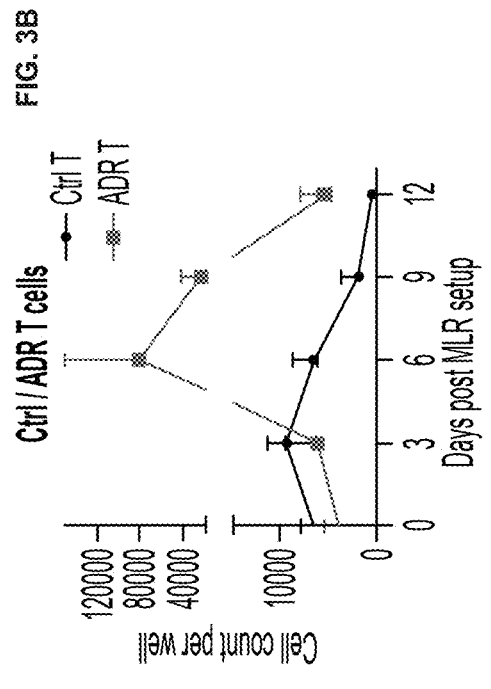
Figure 3C:
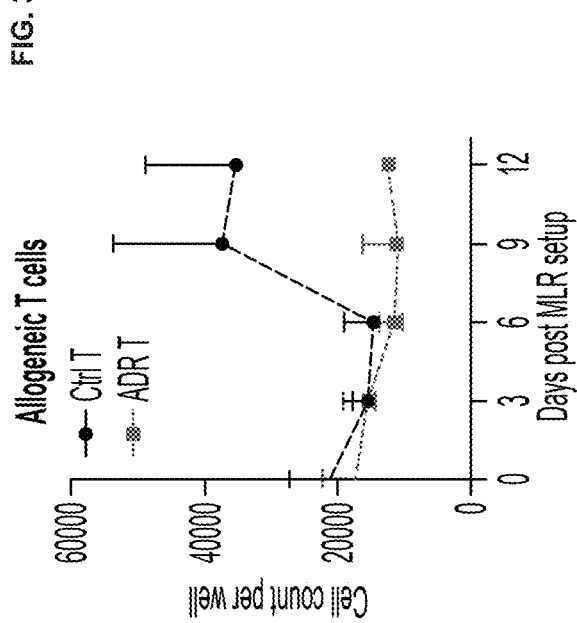
Figure 3A:
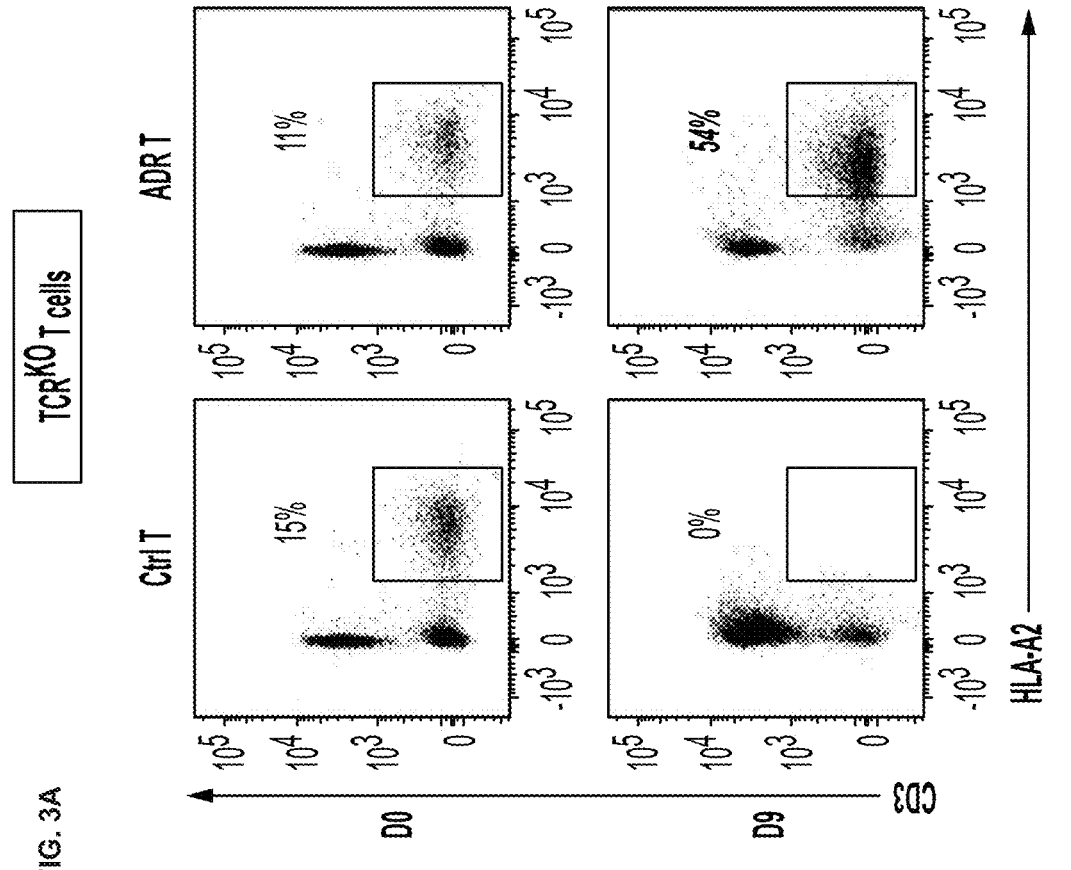

As one example, expression of 4-1BB ADR protects T cells from immune rejection in an MLR model. Representative dot plots showing TCRKO T cells co-expressing ADR are protected from rejection after co-culture with allogeneic PBMC at a 1:10 ADR T:PBMC ratio (FIG. 3A). Absolute counts of donor T cells and allogeneic T cells in the PBMC during co-culture (FIG. 3B-FIG. 3C) are the same for virus-specific ADR T cells (FIG. 3D-FIG. 3F).

Figure 4A:
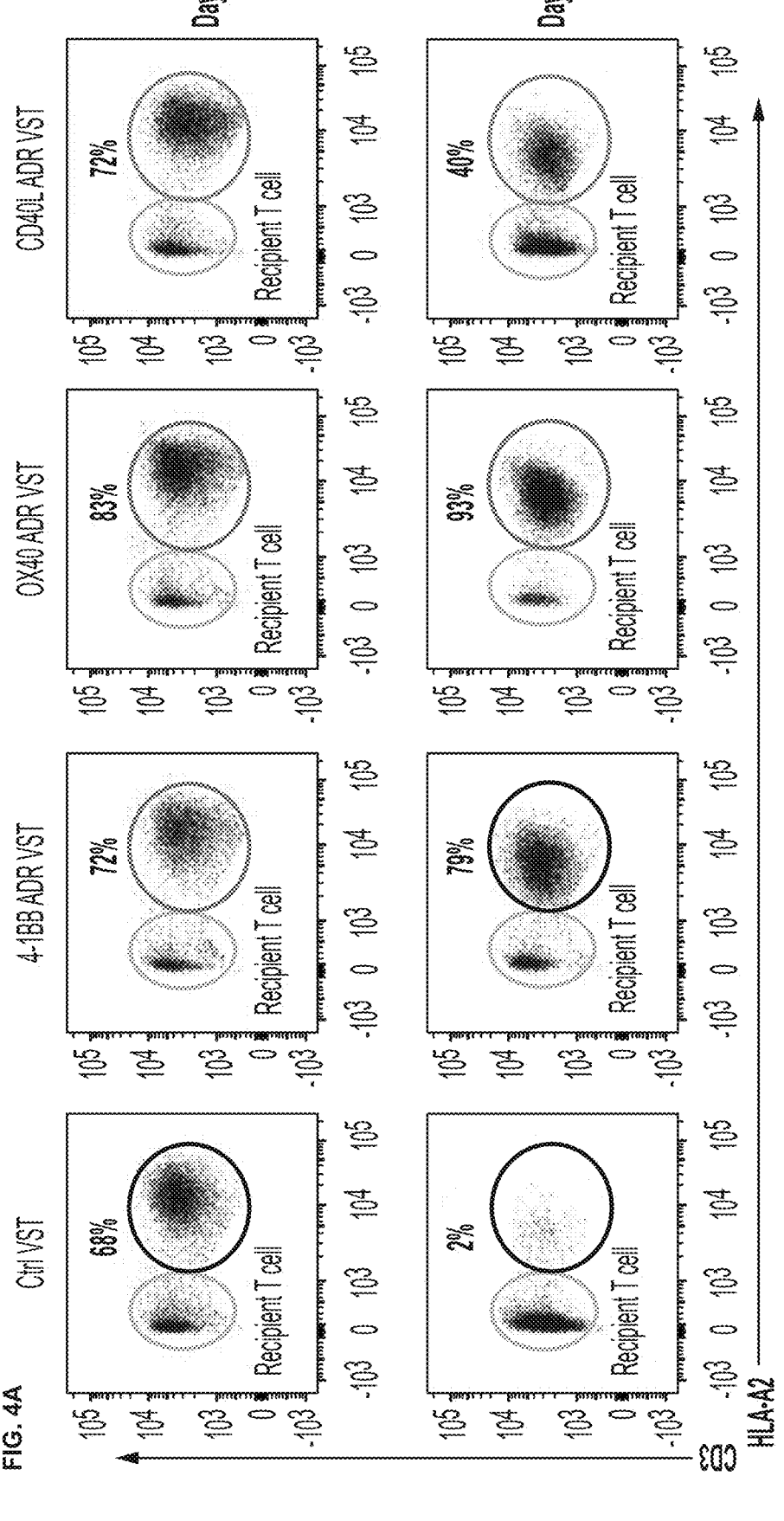
FIGS. 4A-4C. Expression of ADR protects allogeneic virus-specific T cells from immune rejection in a mixed lymphocyte reaction in vitro (FIG. 4A) Representative dot plots showing ADR VST are protected from immune rejection by recipient allogeneic PBMC (FIG. 4B-FIG. 4C) Absolute counts of recipient T cells and donor VST at various time points during MLR.
Figure 4B:
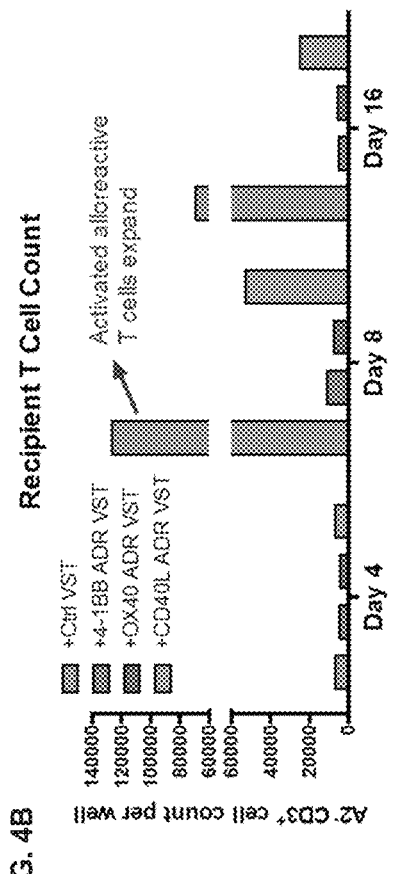
Figure 4C:
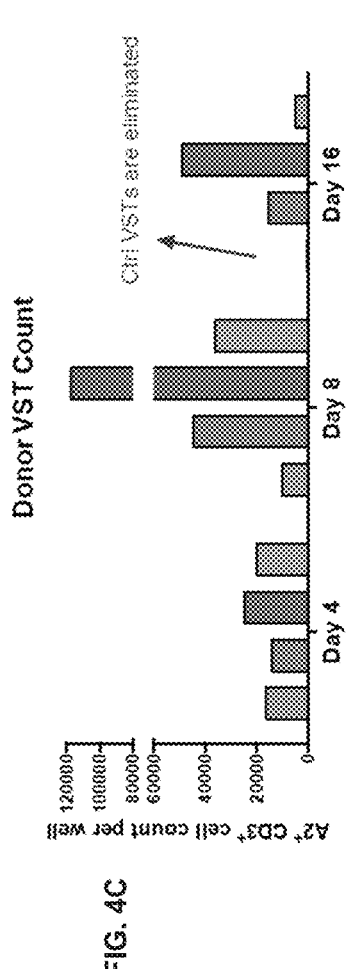

Expression of ADR protects allogeneic virus-specific T cells from immune rejection in a mixed lymphocyte reaction in vitro. Representative dot plots showing ADR VST are protected from immune rejection by recipient allogeneic PBMC (FIG. 4A). The absolute counts of recipient T cells and donor VST at various time points during MLR are provided in FIG. 4B and FIG. 4C.

Figure 5:
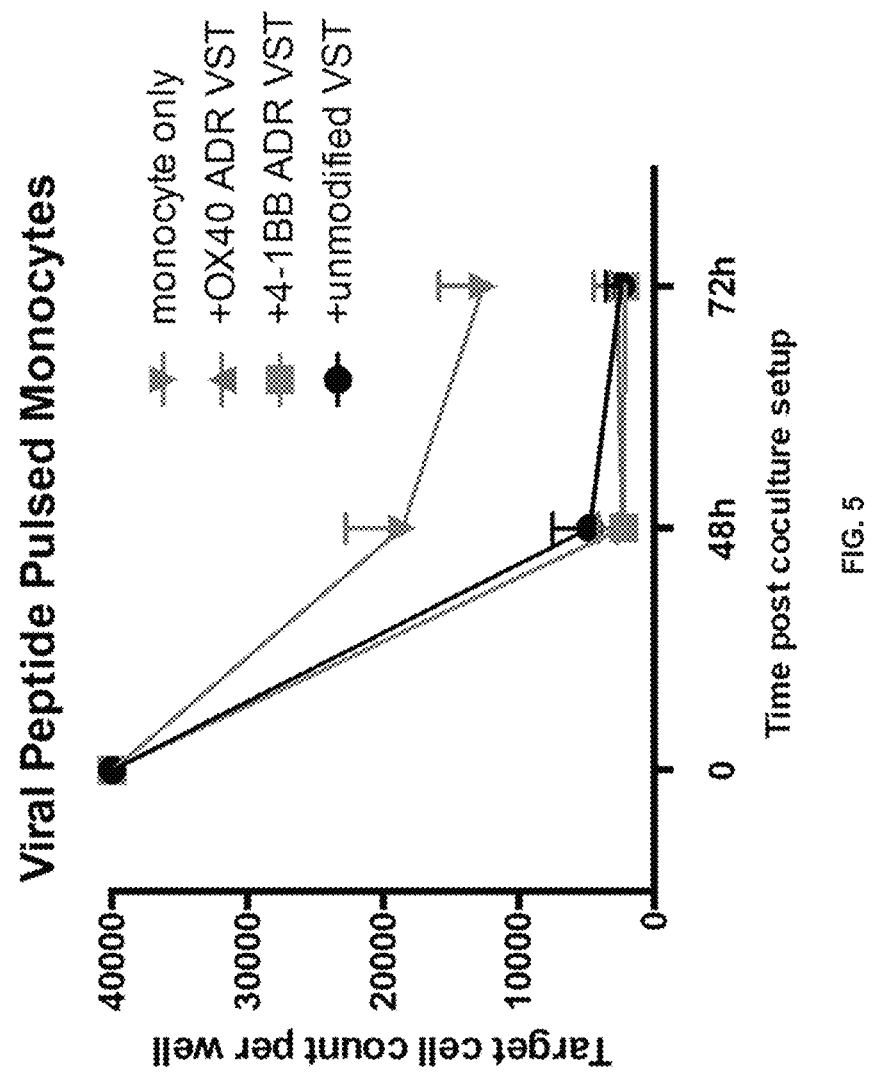
FIG. 5. ADR VSTs retain anti-viral function. ADR VSTs were cocultured with viral pepmix-pulsed monocytes, and monocyte counts indicated that they eliminated viral infected cells equally well compared to unmodified VSTs.

In FIG. 5, ADR VSTs retain anti-viral function. ADR VSTs were co-cultured with viral pepmix-pulsed monocytes, and monocyte counts indicated that they eliminated viral infected cells equally well compared to unmodified VSTs.

Figures 6B, 6C:
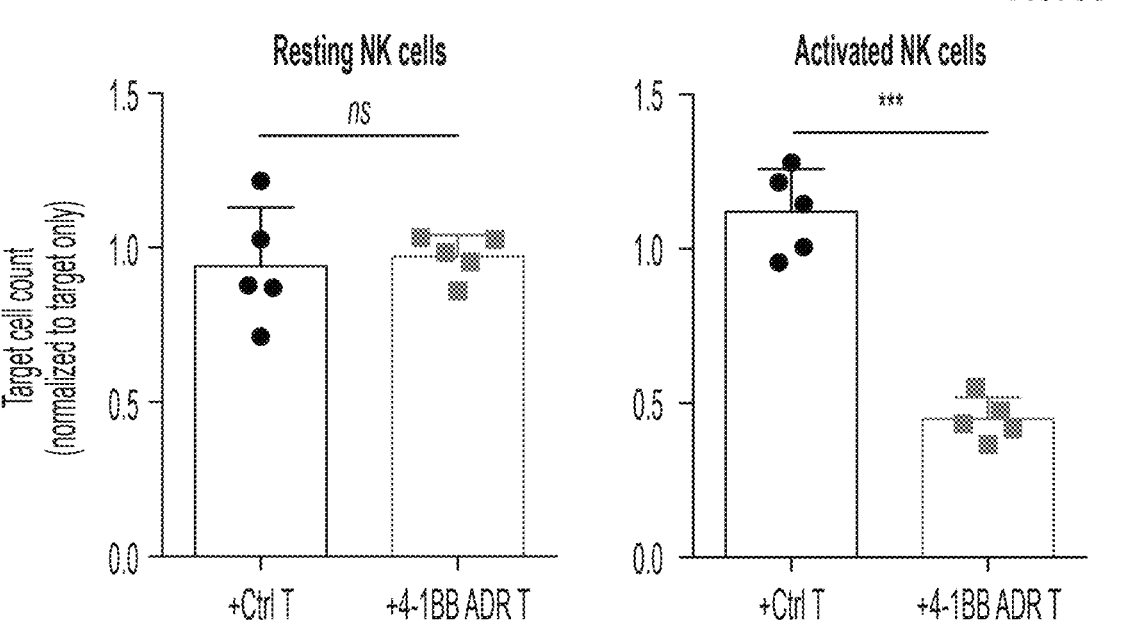
Figure 6D:
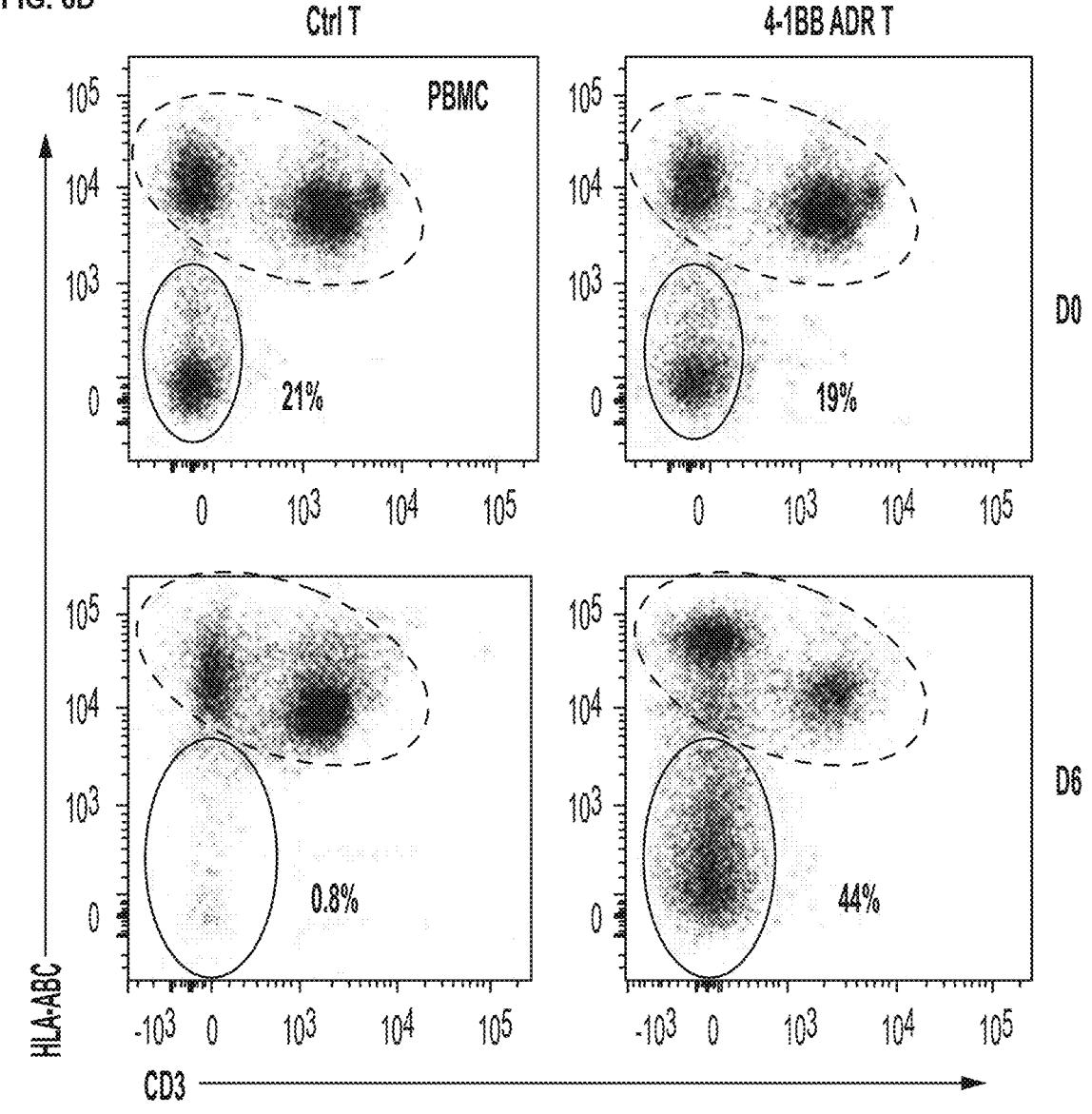
Figure 6E:
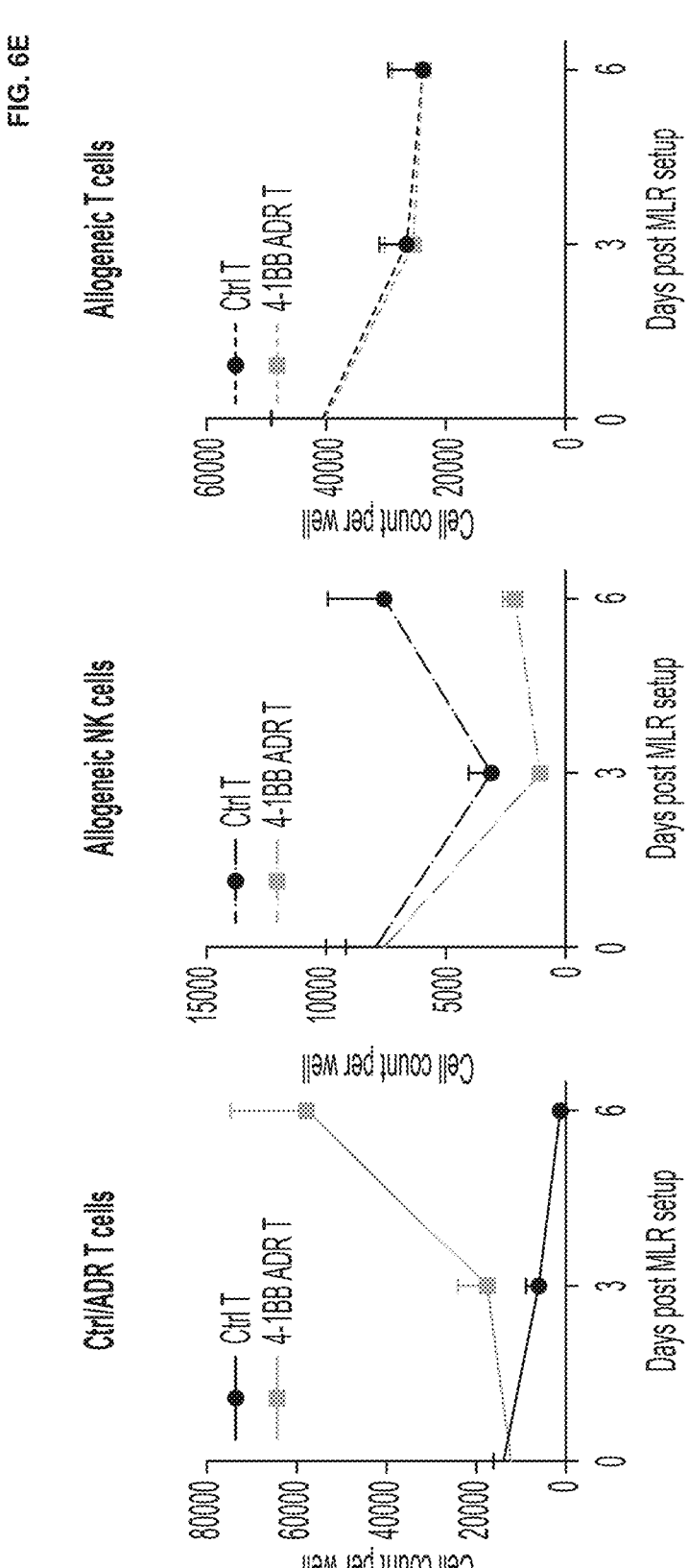
Figure 6F:
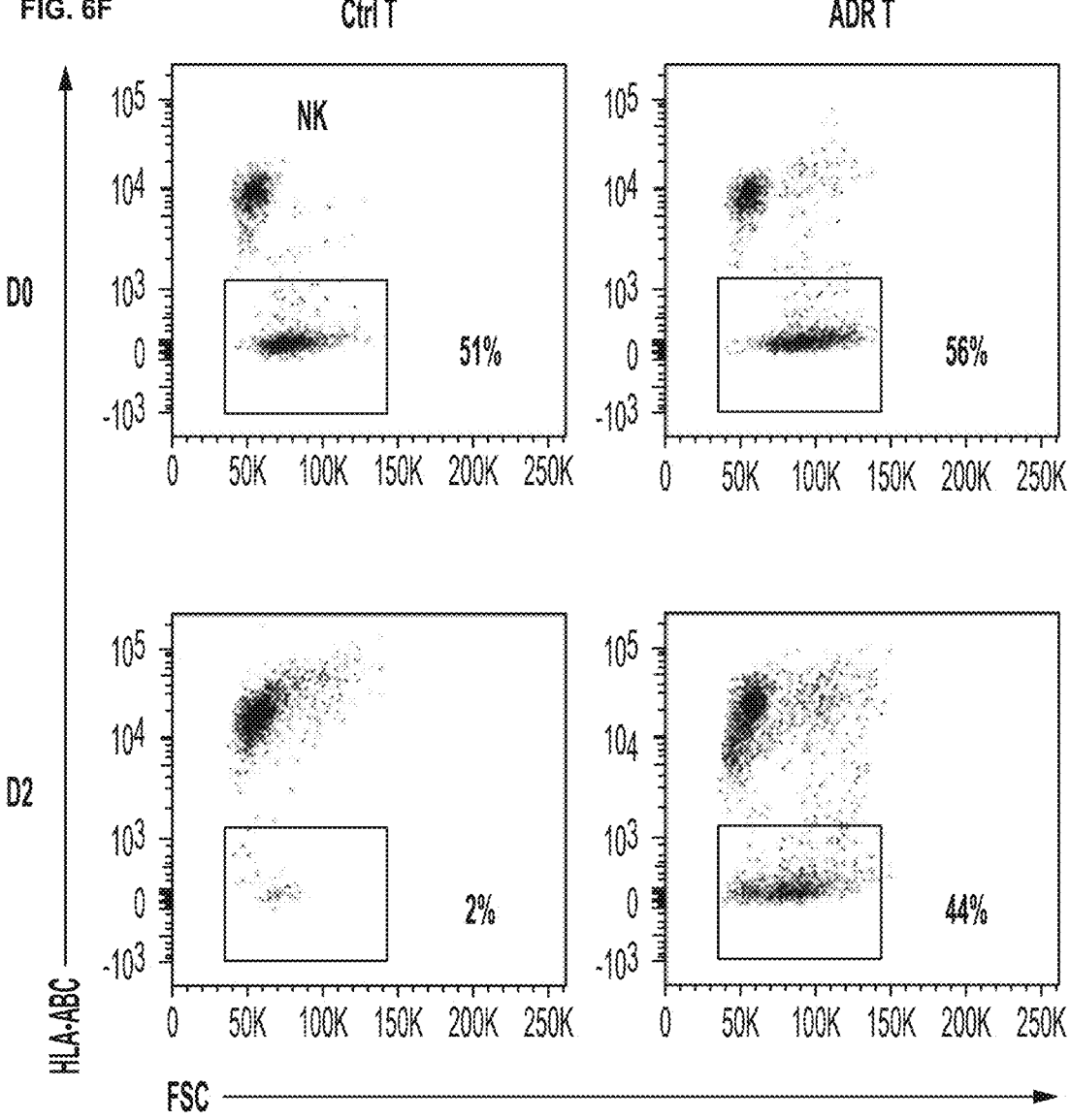
Figures 6G, 6H:
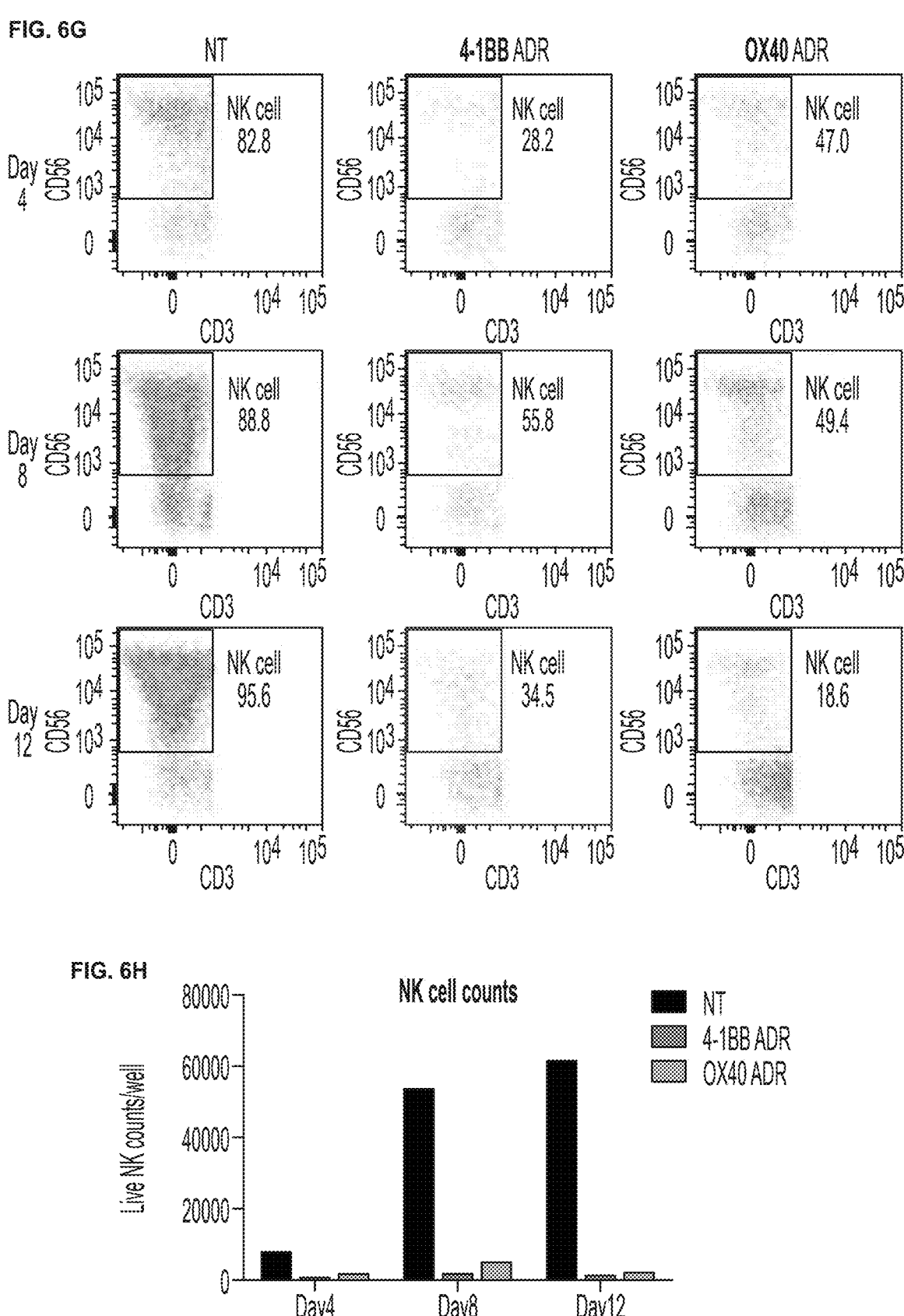

Activated NK cells upregulate ADR ligands and can be selectively targeted by ADR T cells. Expression of 4-1BB on resting vs activated NK cells is confirmed (FIG. 6A-FIG. 6B). Residual counts of resting vs activated NK cells after 24 hr co-culture with 4-1BB ADR T cells are determined (FIG. 6C). In FIG. 6D, ADR T cells lacking MHC are protected from immune rejection by allogeneic PBMC by controlling the expansion of NK cells. Absolute counts of donor T cells and allogeneic NK cells during co-culture are determined in FIG. 6E. ADR T cells lacking MHC resist immune rejection by NK cells upon 48 h co-culture at a 1:1 E:T ratio (FIG. 6F). ADR T cells control the expansion of alloreactive NK cells during MLR with PBMC (FIG. 6G), with absolute counts of NK cells plotted in FIG. 6H.

Figure 7C:
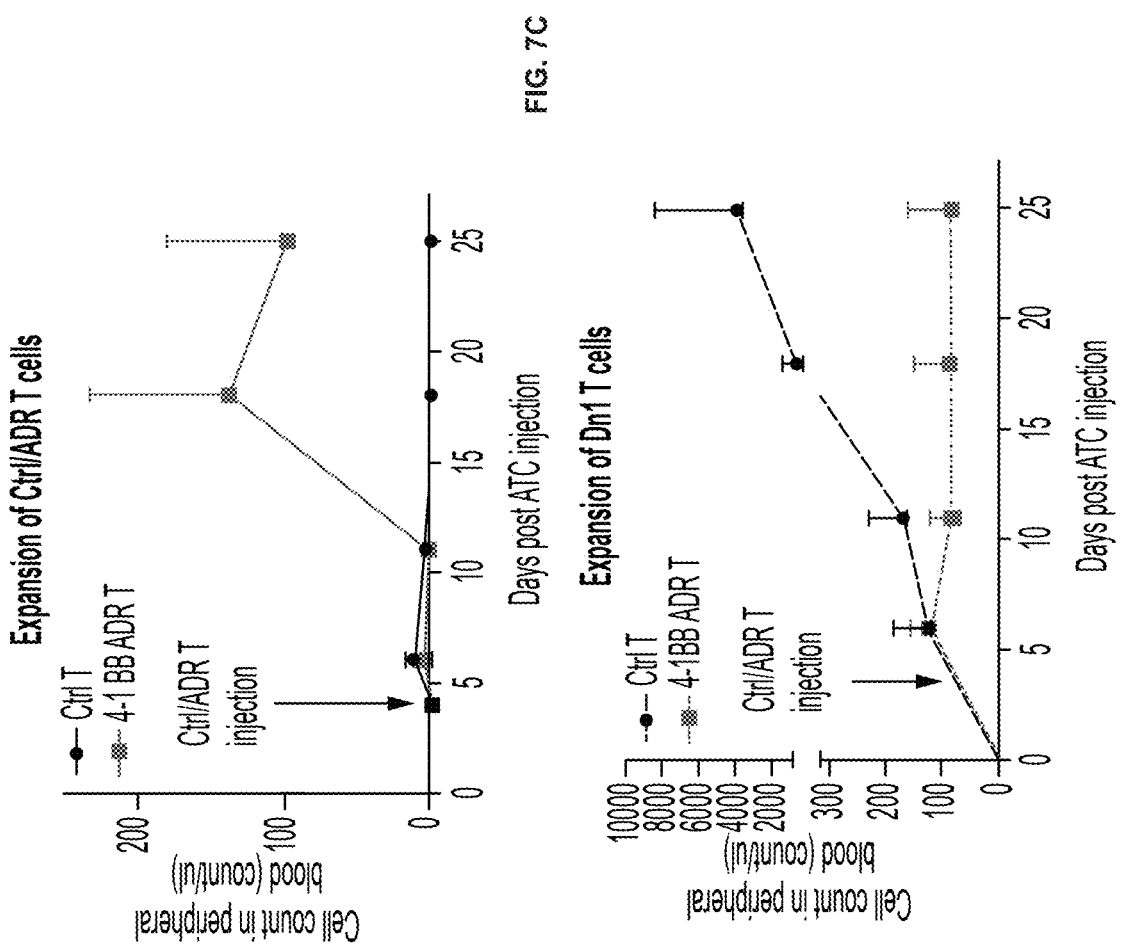

ADR expression protects allogeneic T cells from immune rejection in vivo. In FIG. 7A, one example is shown of a mouse model of immune rejection where mice were given T cells from an HLA-A2+ donor after a sublethal irradiation, followed by administration of allogeneic HLA-A2– T cells 4 days later. Control T cells from the HLA-A2– donor were rejected by Day 18 while ADR-expressing cells were protected (FIG. 7B). Absolute counts of T cells from HLA-A2+ and HLA-A2– donors at various time points were determined (FIG. 7C). A modified in vivo model in FIG. 7D depicts where, instead of allogeneic T cells mice, received whole PBMC (containing both T- and NK-cells) from donor 1. Representative flow plots in FIG. 7E show that ADR T cells were protected from immune rejection and also protected mice from rapid onset of fatal GvHD.

Figures 8A, 8B:
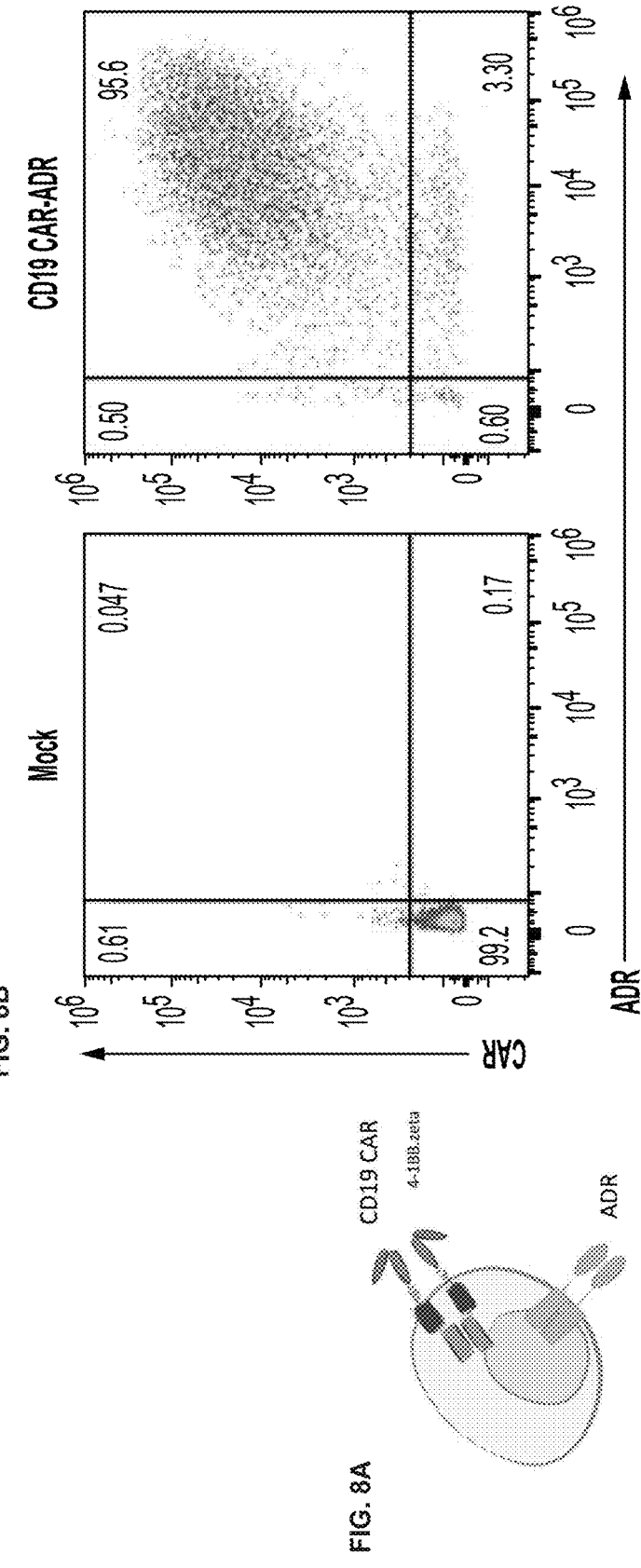

Coexpression of CAR and ADR preserves functions of both receptors. FIG. 8A illustrates an example of a representation of an immune cell co-expressing ADR and a CAR Coexpression of a CAR and an ADR on the cell surface were confirmed (FIG. 8B). In FIG. 8C, cytotoxicity is shown of CAR-ADR T cells against NALM-6 (A CD19+ CAR target), as one example of a target. Cytotoxicity of the CAR-ADR T cells against activated T cells (ADR target) were also determined in FIG. 8D. Cytotoxic activity of CAR-ADR T cells against both targets upon simultaneous co-culture with both cell targets is demonstrated in FIG. 8E.

Figures 1, 9A, 9B:
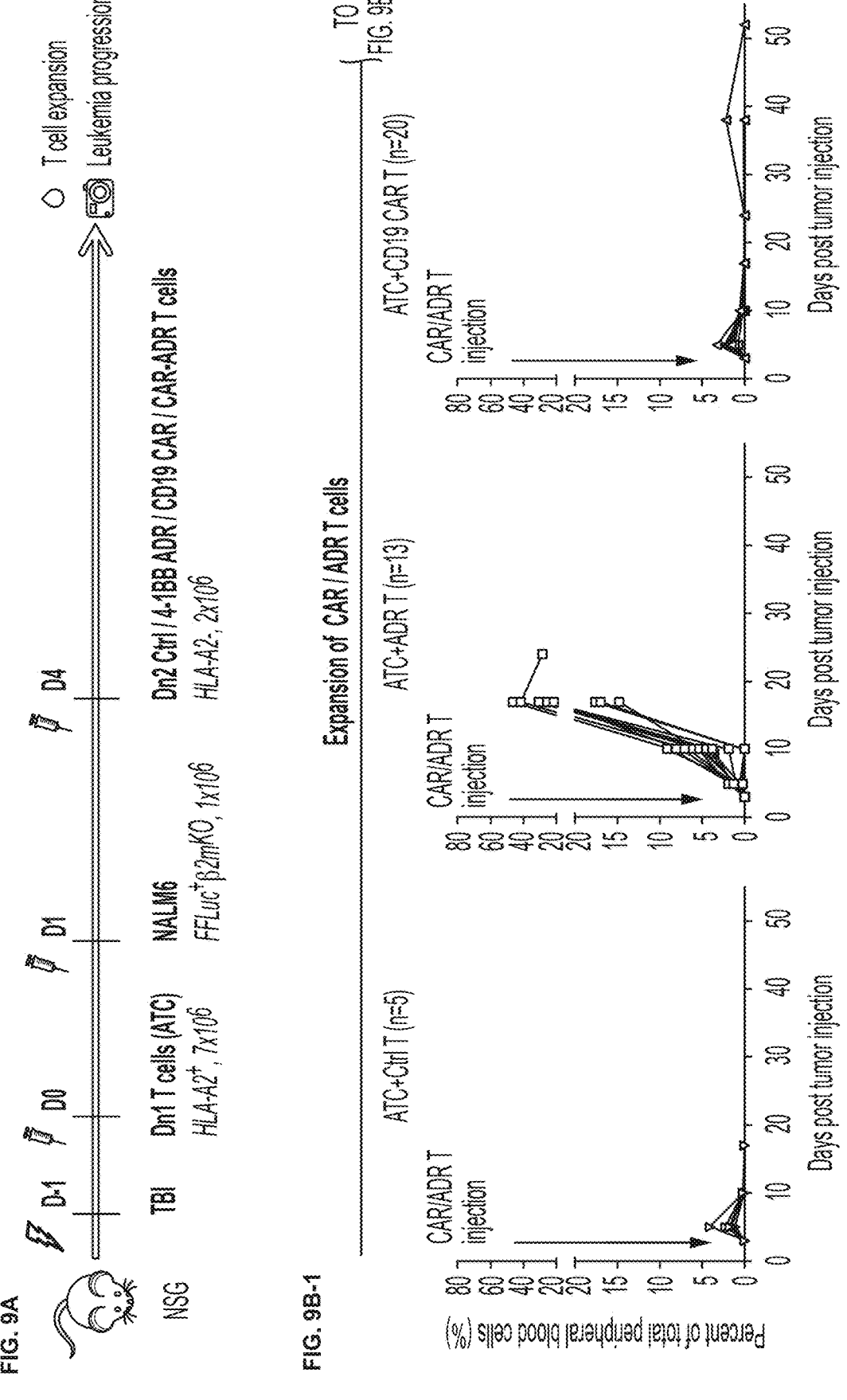
FIGS. 9A-9E. CAR-ADR T cells are protected from immune rejection and exert potent anti-tumor activity (FIG. 9A) Schematic of the mouse model. Mice received allogeneic T cells from Donor 1 and b2mKO NALM6 24 hr apart, followed by a single dose of CAR-ADR T cells from Donor 2.
Figures 1, 2, 9B:
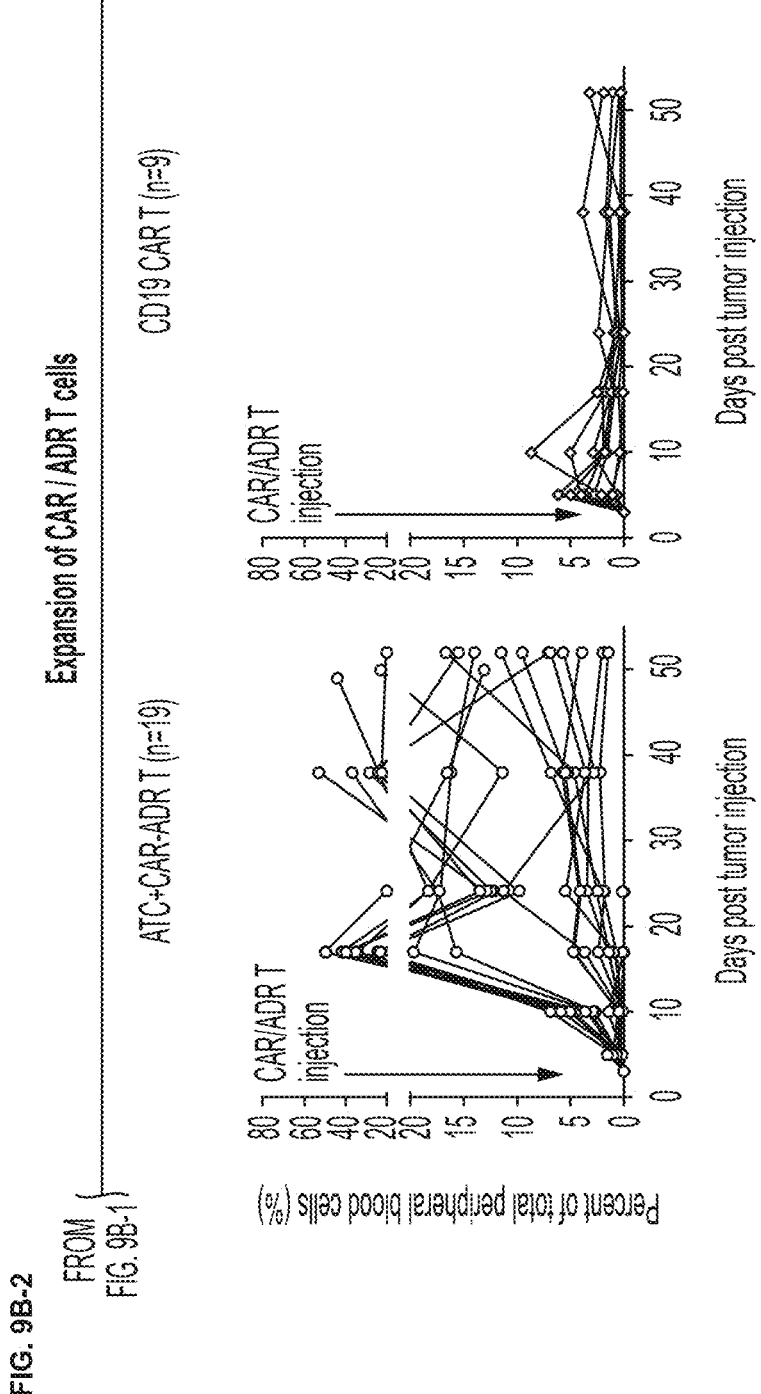
Figures 1, 9C, 9D:
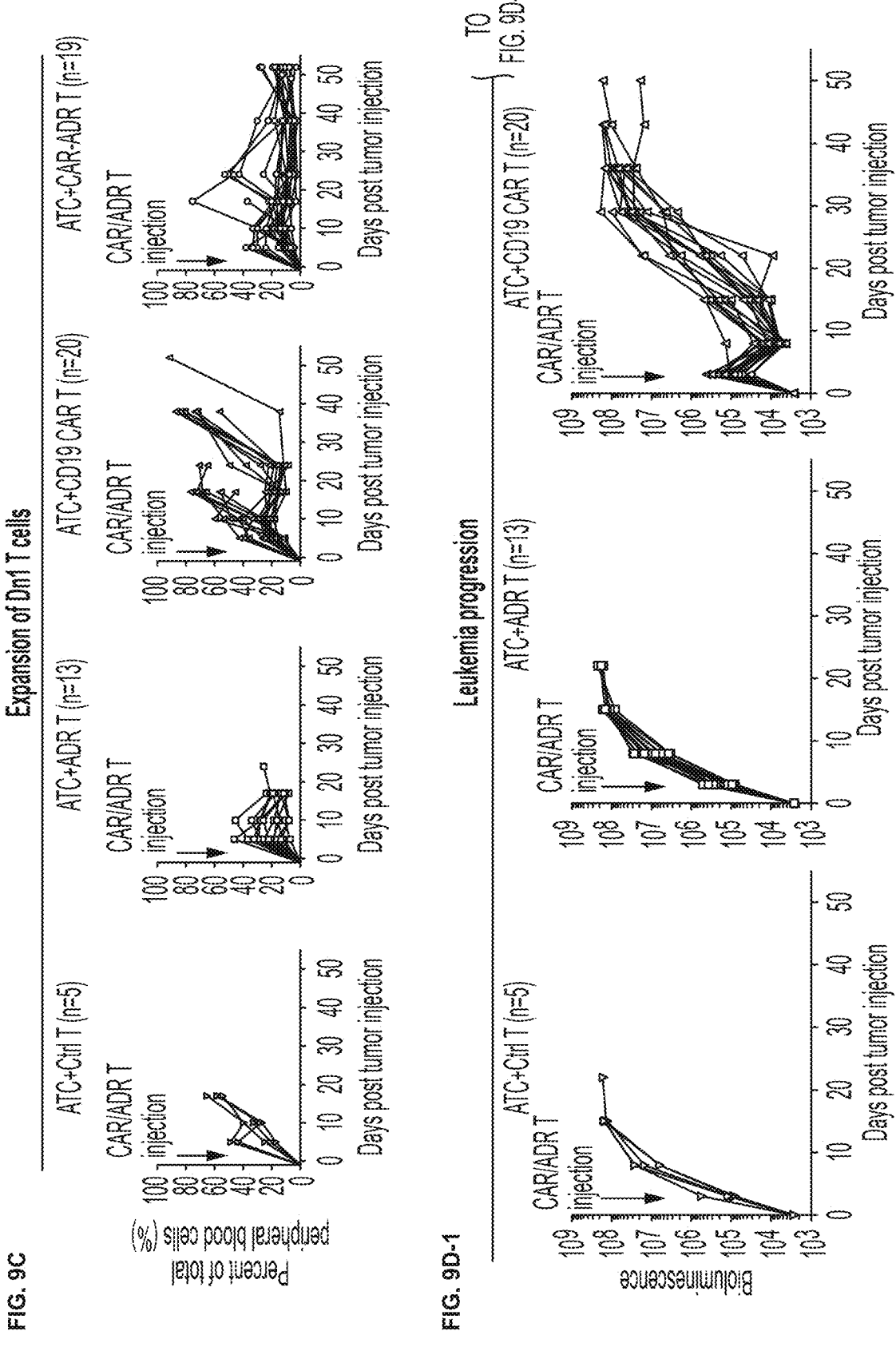
Figures 1, 2, 9D:
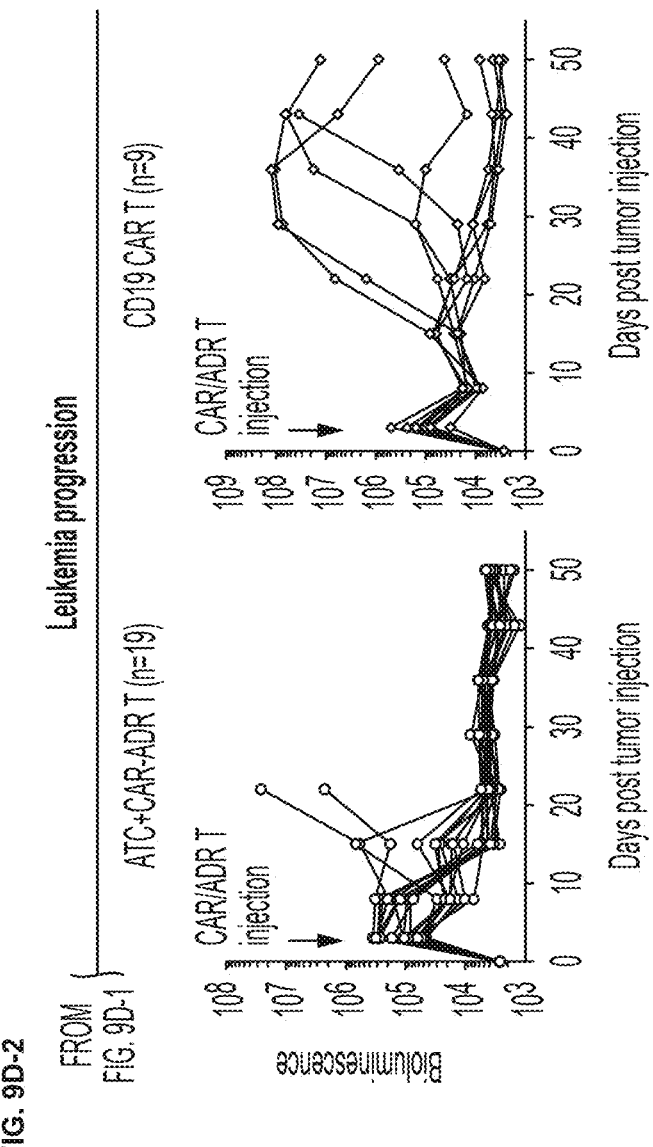
Figure 9E:
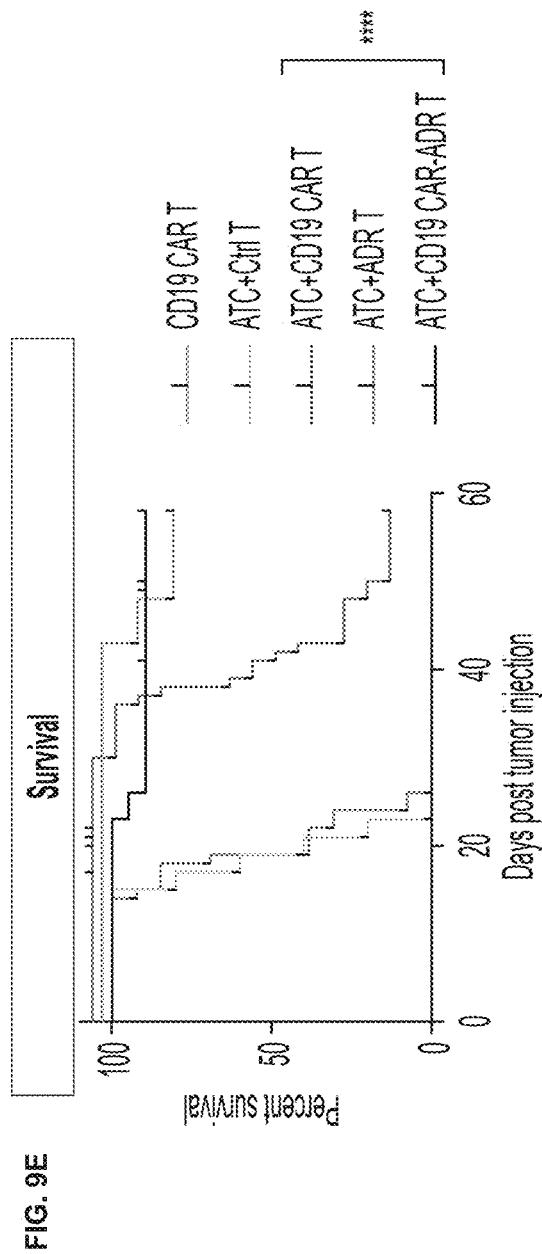

CAR-ADR T cells are protected from immune rejection and exert potent anti-tumor activity. An example of a mouse model and a regimen is depicted in FIG. 9A. Mice received allogeneic T cells from Donor 1 and b2mKO NALM6 24 hr apart, followed by a single dose of CAR-ADR T cells from Donor 2, as one example of a regimen. Kinetics of T cells from Donor 2 in peripheral blood are provided in FIG. 9B, and kinetics of Donor 1 T cells in the experimental groups are provided in FIG. 9C. FIG. 9D shows leukemia burden in the mice, with determination of overall survival of the mice (FIG. 9E).

Figures 13A, 13B, 13C, 13D:
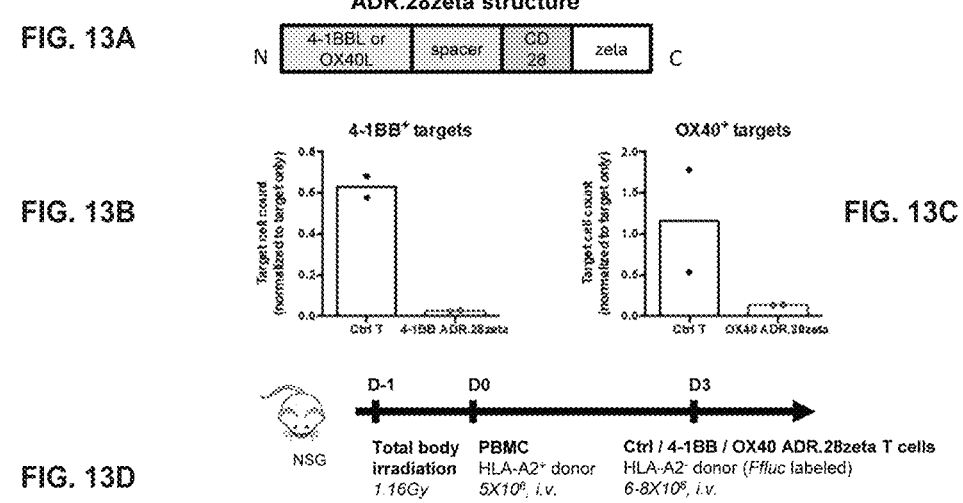
FIGS. 13A-13G. 2nd generation ADR with CD28 intracellular signaling domain (ADR.28zeta).

FIGS. 13A-13C. CAR-ADR T cells are protected from immune rejection and exert potent anti-tumor activity in a solid tumor model. Schematic of an example of a mouse model and treatment is shown in FIG. 10A, wherein mice received allogeneic T cells from Donor 1 and b2mKO neuroblastoma cell line CHLA255 24 hr apart, followed by a single dose of CAR-ADR T cells from Donor 2. Donor 2 GD2 CAR T cells were rejected by D18, whereas CAR-ADR T cells resisted allogeneic rejection and persisted in peripheral blood (FIG. 10B). Tumor burden in mice is shown in FIG. 13C, where * indicates xenogeneic-GvHD associated deaths in ATC+GD2 CAR T group.

Figures 2, 11B:
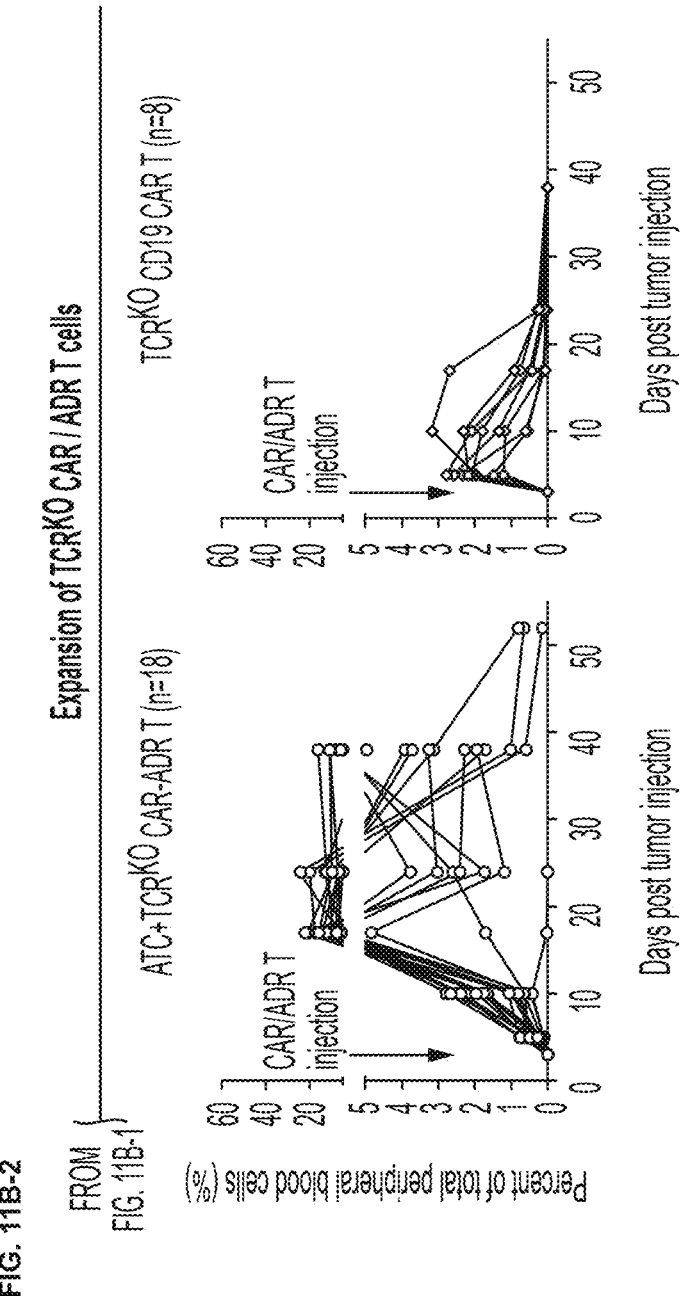
Figures 1, 11C, 11D:
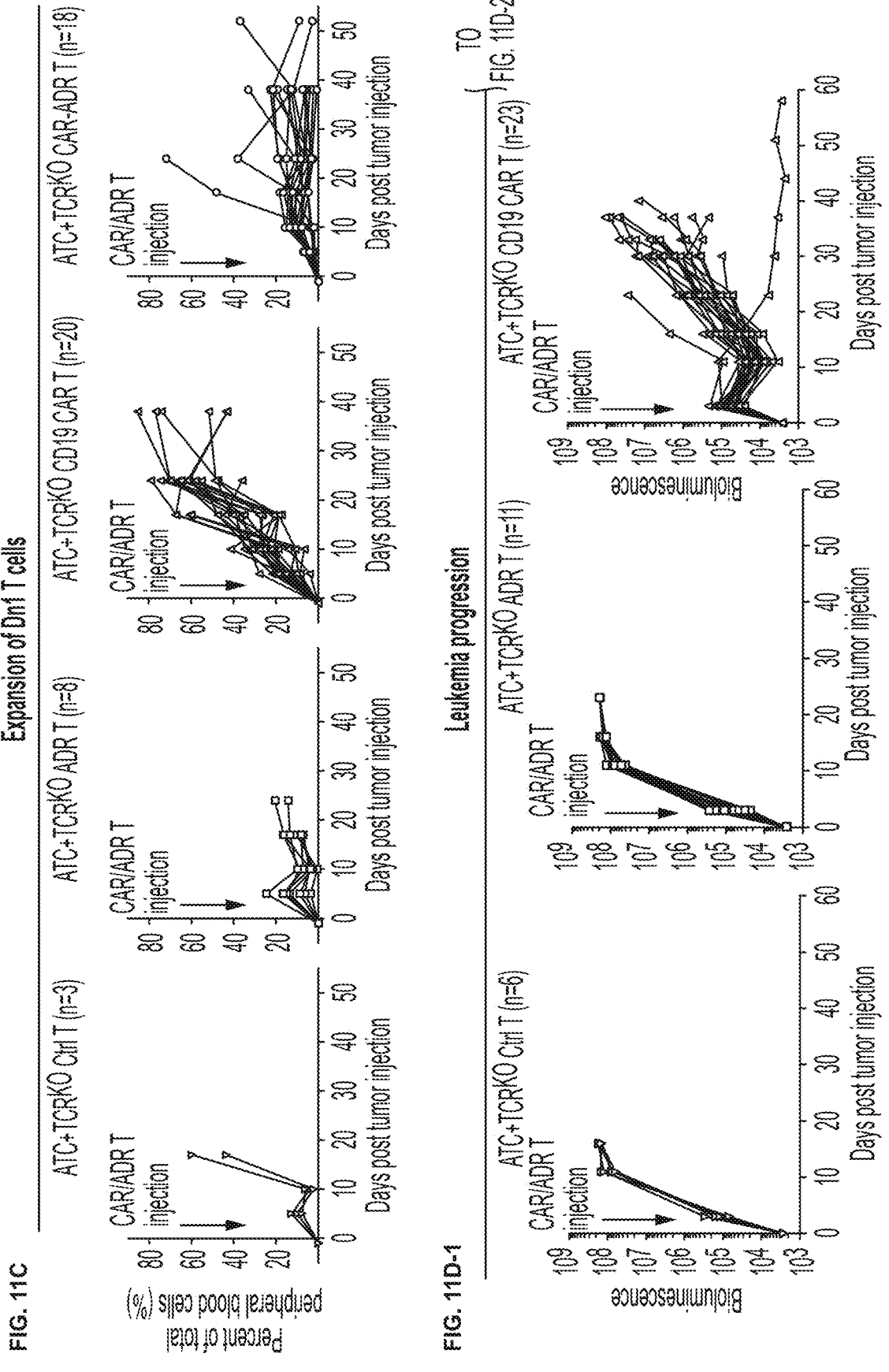
Figures 1, 2, 11D:
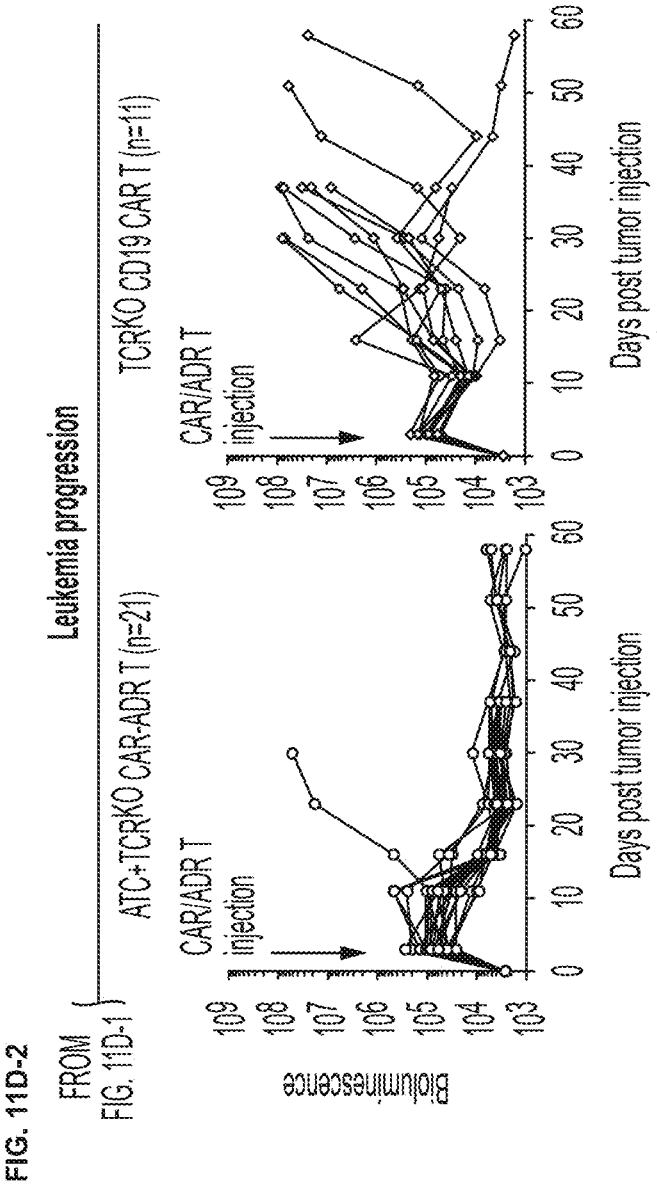
Figure 11E:
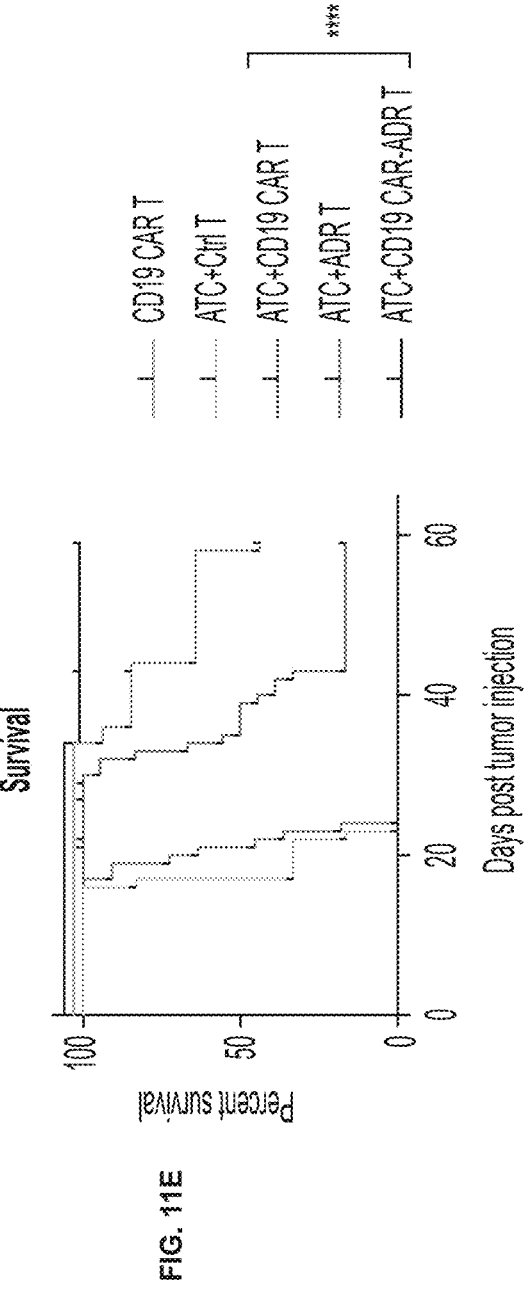

TCR-knockout CAR-ADR T cells are protected from immune rejection and exert potent anti-tumor activity. Schematic of the mouse model is provided in which mice received allogeneic T cells from Donor 1 and b2mKO NALM6 24 hr apart, followed by a single dose of TCR-edited CAR-ADR T cells from Donor 2 (FIG. 11A). Kinetics of T cells from Donor 2 in peripheral blood are provided (FIG. 11B). Kinetics of Donor 1 T cells in the experimental groups are shown (FIG. 11C). Leukemia burden in mice (FIG. 11D) and overall survival of mice are provided (FIG. 11E).

Figures 12A, 12B:
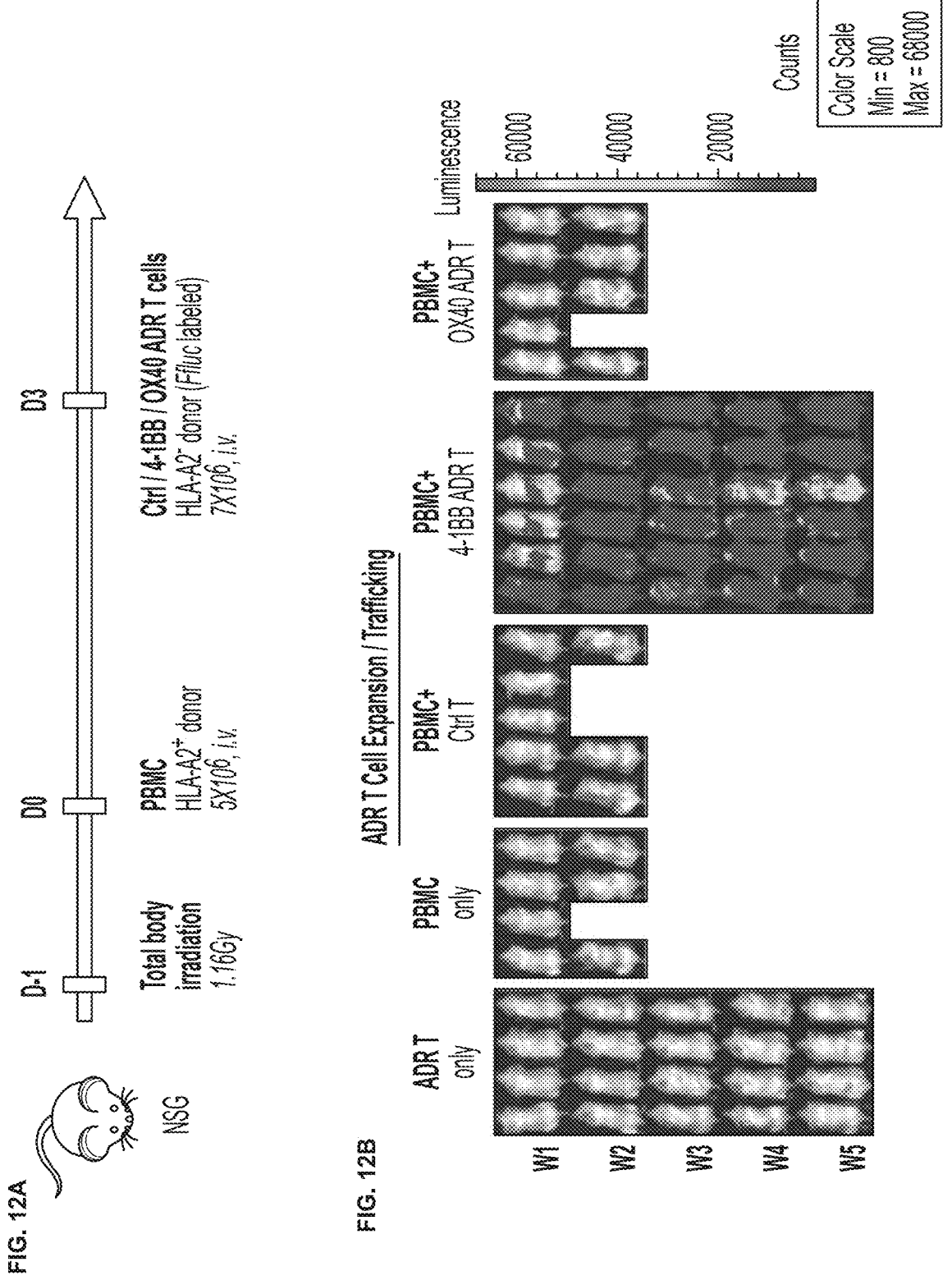
FIGS. 12A-12D. ADR T cells protect mice against fatal xenogeneic GvHD (FIG. 12A) Schematic of the model (FIG. 12B) Expansion of FFLuc-labeled ADR T cells in vivo (FIG. 12C) Kinetics of weight gain/loss in mice (FIG. 12D) Overall survival of mice.
Figure 12C:
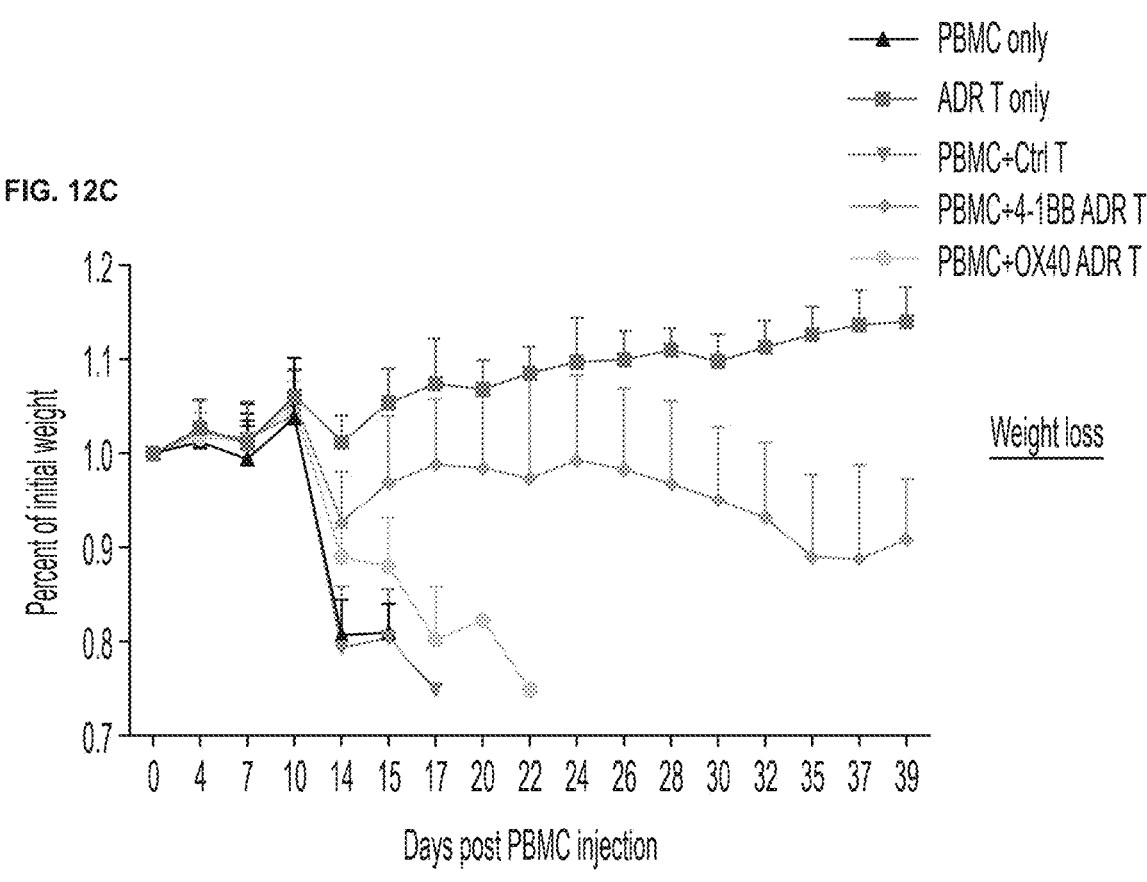
Figure 12D:
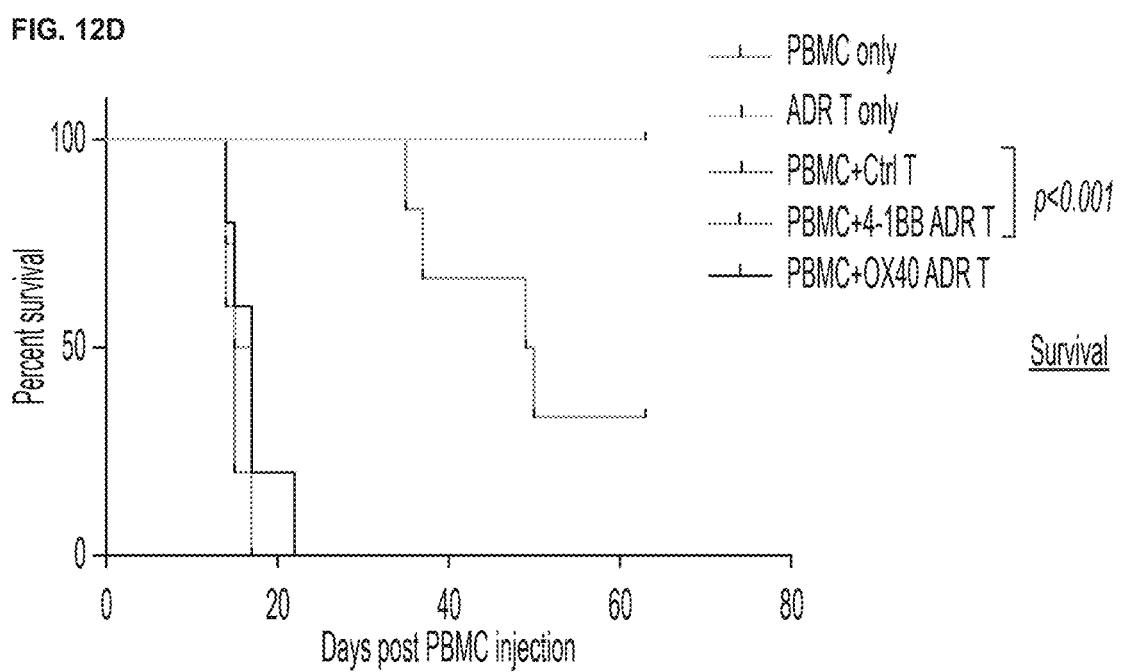

ADR T cells protect mice against fatal xenogeneic GvHD. Schematic of a model is provided in FIG. 12A, and expansion of FFLuc-labeled ADR T cells in vivo is demonstrated (FIG. 12B). Kinetics of weight gain/loss in mice were determined (FIG. 12C). Overall survival of mice is depicted (FIG. 12D).

Second generation ADR with CD28 intracellular signaling domain ("ADR.28zeta")(as one example) were utilized. One example of a structure of ADR.28zeta is depicted (FIG. 13A). In vitro cytotoxicity was determined of ADR.28zeta against target-expressing cells ((FIG. 13B and FIG. 13C).

29

30

Figure 13E:
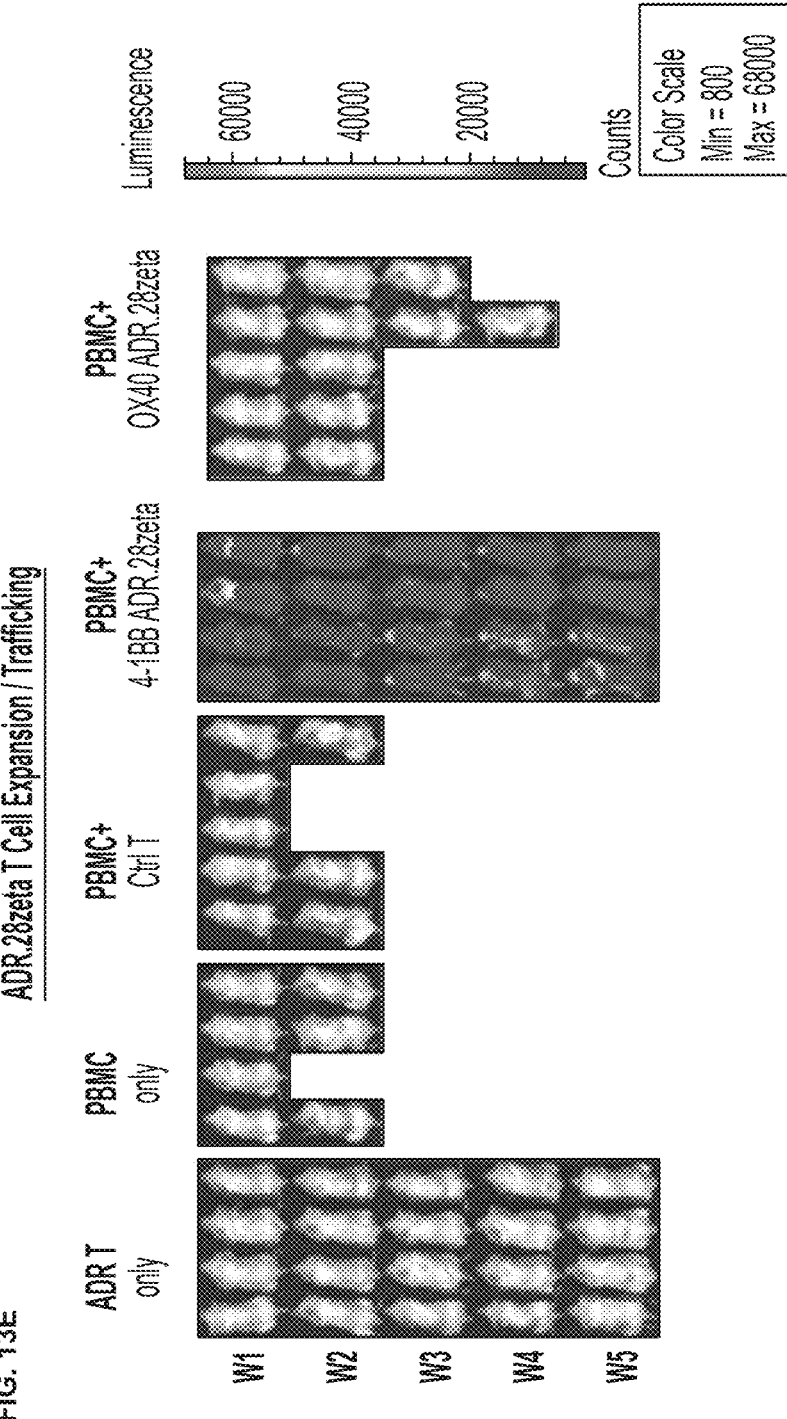
Figure 13F:
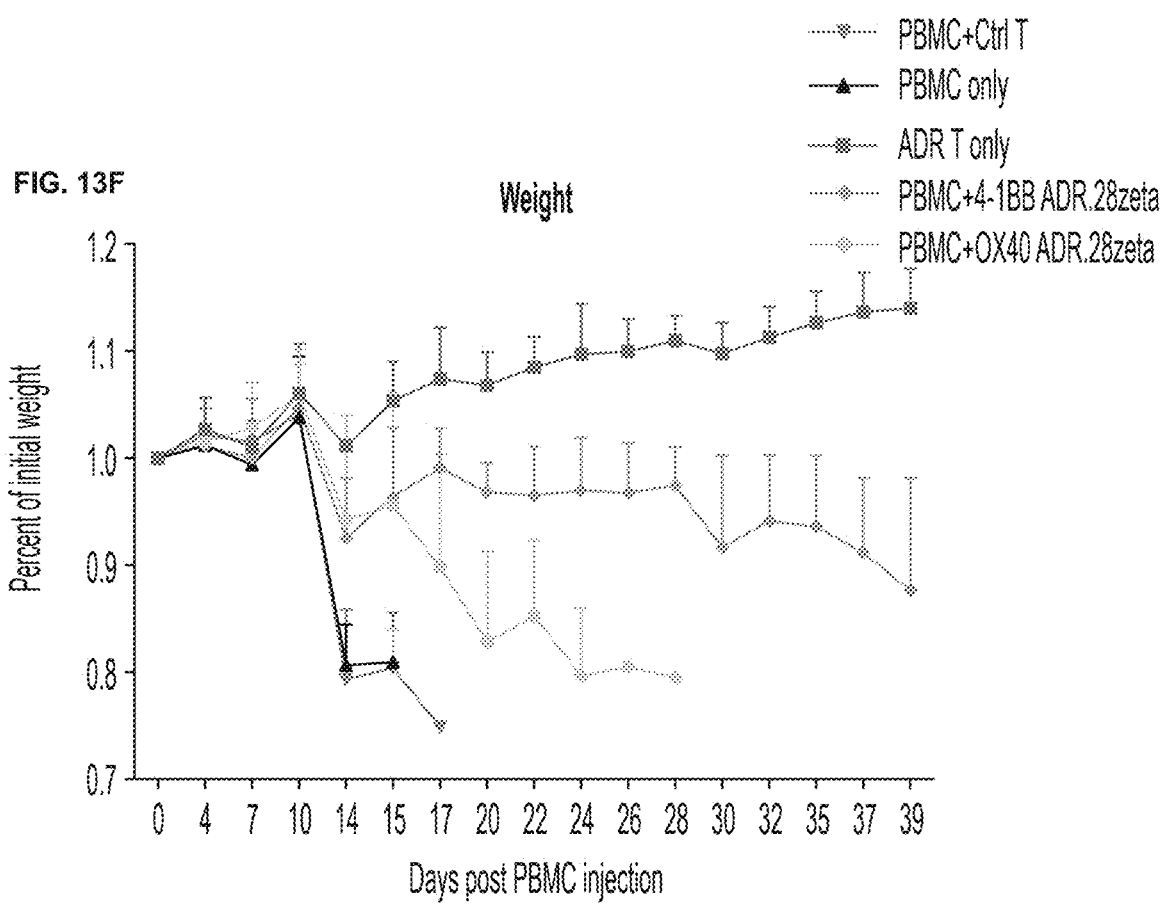
Figure 13G:
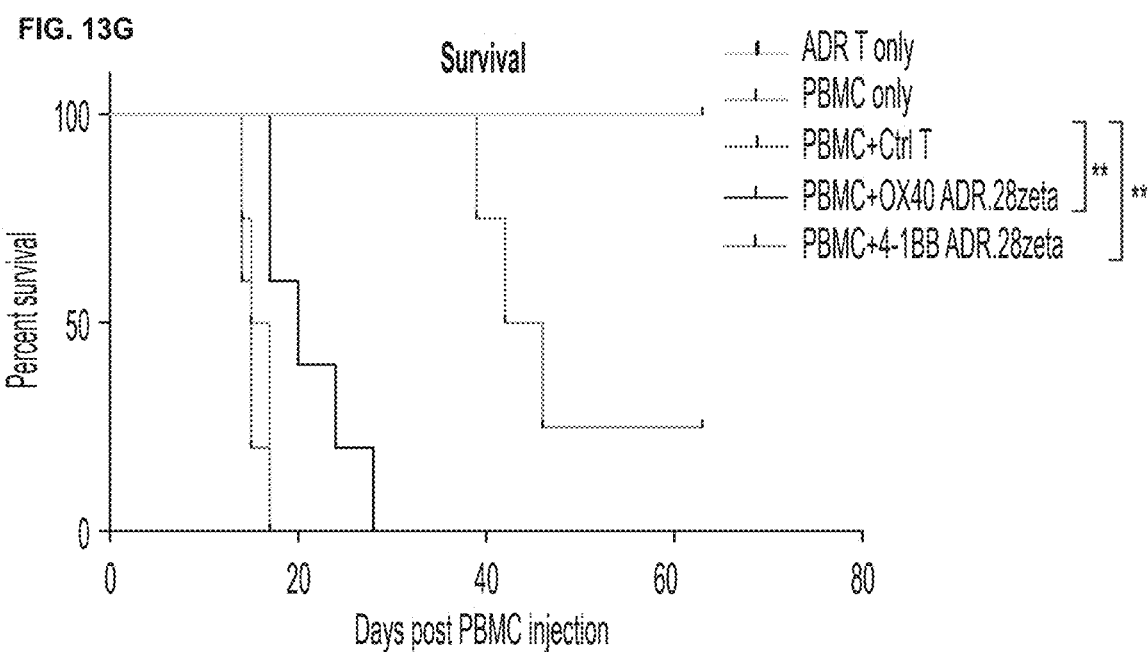

ADR.28zeta protected mice from xeno-GvHD lines (FIG. 13B). Schematic of the model (FIG. 13D) is shown. Expansion of FFLuc-labeled ADR.28zeta T cells in vivo was confirmed (FIG. 13E) Kinetics of weight gain/loss in mice (FIG. 13F), and the overall survival of mice was determined (FIG. 13G).

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

---

What is claimed is:

1. A polypeptide, comprising:

(1) an extracellular domain comprising one or more of an OX40-specific ligand, a 4-1BB-specific ligand, and CD40; that is operably linked to (2) an intracellular signaling domain promoting T-cell activation;

wherein: (i) the polypeptide is encoded by a polynucleotide; (ii) the polypeptide comprises both (1) and (2); and (iii) the polypeptide comprises a transmembrane domain between (1) and (2).

2. The polypeptide of claim 1, wherein:

(i) the intracellular signaling domain promoting T-cell activation is, from CD3 zeta subunit, DAP12, an Fc receptor, or a combination thereof; and/or (ii) the polypeptide further comprises 1, 2, or more costimulatory domains.

3. The polypeptide of claim 1, wherein:

(i) the polypeptide comprises the OX40-specific ligand; or (ii) the polypeptide comprises the 4-1BB-specific ligand.

4. The polypeptide of claim 3, wherein:

(i) the OX40-specific ligand is OX40L, an antibody that targets OX40, an OX40L-Fc fusion, or a combination thereof, or (ii) the 4-1BB-specific ligand is 4-1BBL, an antibody that targets 4-1BB, a 4-1BBL-Fc fusion, or a combination thereof.

5. The polypeptide of claim 1, wherein the polypeptide further comprises 1, 2, or more costimulatory domains.

6. The polypeptide of claim 1, wherein the polynucleotide further comprises sequence that encodes a spacer between (1) and (2).

7. The polypeptide of claim 6, wherein:

(i) the spacer is between 10 and 220 amino acids in length;

(ii) the spacer has sequence that facilitates surface detection with an antibody;

(iii) the spacer is detectable with an anti-Fc Ab; and/or (iv) the spacer comprises IgG Fc portion.

8. The polypeptide of claim 1, wherein the polynucleotide further comprises a sequence encoding a chimeric antigen receptor, a T-cell receptor, or both.

9. The polypeptide of claim 8, wherein the chimeric antigen receptor comprises one or more costimulatory domains.

10. The polypeptide of claim 1, wherein the polynucleotide:

(i) is present on a vector; or (ii) is present in a cell.

11. The polypeptide of claim 10, wherein the vector is a retroviral vector, lentiviral vector, adenoviral vector, or adeno-associated viral vector.

12. The polypeptide of claim 10, wherein the cell is:

(i) a eukaryotic cell or a bacterial cell; or (ii) an immune cell.

13. The polypeptide of claim 12, wherein the immune cell is a T cell.

14. The polypeptide of claim 13, wherein the T cell comprises:

(i) one or more chimeric antigen receptors; or (ii) one or more engineered T cell receptors (TCRs).

15. The polypeptide of claim 8, wherein the chimeric antigen receptor comprises 1, 2, or more costimulatory domains.

16. The polypeptide of claim 1, wherein the polynucleotide is comprised in an engineered cell.

17. The polypeptide of claim 16, wherein the engineered cell is an immune cell.

18. The polypeptide of claim 17, wherein the immune cell is a T cell.

19. The polypeptide of claim 18, wherein the T cell is a CAR-transduced T cell.

20. The polypeptide of claim 18, wherein the T cell is a T cell receptor (TCR)-transduced T cell.

21. The polypeptide of claim 16, wherein the engineered cell is engineered to lack endogenous expression of one or more genes.

22. The polypeptide of claim 21, wherein the engineered cell is engineered to lack endogenous expression of 4-1BB, OX40 and/or CD40L.

23. The polypeptide of claim 16, wherein the engineered cell is engineered using CRISPR/Cas9, zinc finger nucleases, TALE nucleases, or meganucleases.

24. The polypeptide of claim 16, wherein the engineered cell is housed in a cell repository.

* * * * *